US010441654B2

(12) United States Patent
Korneluk et al.

(10) Patent No.: US 10,441,654 B2
(45) Date of Patent: Oct. 15, 2019

(54) SMC COMBINATION THERAPY FOR THE TREATMENT OF CANCER

(71) Applicant: Children's Hospital of Eastern Ontario Research Institute Inc., Ottawa (CA)

(72) Inventors: Robert G. Korneluk, Ottawa (CA); Eric C. Lacasse, Ottawa (CA); Shawn T. Beug, Ottawa (CA); Vera A. Tang, Ottawa (CA)

(73) Assignee: Children's Hospital of Eastern Ontario Research Institute Inc., Ottawa, ON (CA)

( * ) Notice: Subject to any disclaimer, the term of this patent is extended or adjusted under 35 U.S.C. 154(b) by 0 days.

(21) Appl. No.: 15/113,634

(22) PCT Filed: Jan. 26, 2015

(86) PCT No.: PCT/CA2015/000043
§ 371 (c)(1),
(2) Date: Jul. 22, 2016

(87) PCT Pub. No.: WO2015/109391
PCT Pub. Date: Jul. 30, 2015

(65) Prior Publication Data
US 2017/0239347 A1    Aug. 24, 2017

Related U.S. Application Data

(60) Provisional application No. 61/931,321, filed on Jan. 24, 2014.

(51) Int. Cl.
*A61K 31/427*     (2006.01)
*A61K 39/12*      (2006.01)
*A61K 31/40*      (2006.01)
*A61K 39/39*      (2006.01)
*A61K 35/766*     (2015.01)
*A61K 45/06*      (2006.01)
*A61K 31/404*     (2006.01)
*A61K 31/4745*    (2006.01)
*A61K 35/765*     (2015.01)
*A61K 38/21*      (2006.01)
*A61K 35/761*     (2015.01)
*A61K 31/407*     (2006.01)
*A61K 31/409*     (2006.01)
*A61K 31/433*     (2006.01)
*A61K 31/55*      (2006.01)
*A61K 39/00*      (2006.01)
*A61K 39/205*     (2006.01)
*C12N 7/00*       (2006.01)

(52) U.S. Cl.
CPC ............ *A61K 39/39* (2013.01); *A61K 31/404* (2013.01); *A61K 31/407* (2013.01); *A61K 31/409* (2013.01); *A61K 31/427* (2013.01); *A61K 31/433* (2013.01); *A61K 31/4745* (2013.01); *A61K 31/55* (2013.01); *A61K 35/761* (2013.01); *A61K 35/765* (2013.01); *A61K 35/766* (2013.01); *A61K 38/21* (2013.01); *A61K 38/212* (2013.01); *A61K 39/0011* (2013.01); *A61K 39/205* (2013.01); *A61K 45/06* (2013.01); *C12N 7/00* (2013.01); *A61K 2039/5252* (2013.01); *A61K 2039/55511* (2013.01); *A61K 2039/55561* (2013.01); *A61K 2039/55588* (2013.01); *A61K 2039/55594* (2013.01); *A61K 2039/572* (2013.01); *A61K 2039/585* (2013.01); *C12N 2760/20134* (2013.01)

(58) Field of Classification Search
CPC .... A61K 31/40; A61K 31/395; A61K 31/427; A61K 39/12
See application file for complete search history.

(56) References Cited

U.S. PATENT DOCUMENTS

| | | |
|---|---|---|
| 2003/0224399 A1 | 12/2003 | Reed et al. |
| 2005/0250854 A1 | 11/2005 | Li et al. |
| 2006/0058229 A1 | 3/2006 | Steller et al. |
| 2006/0258581 A1 | 11/2006 | Reed et al. |
| 2007/0042428 A1 | 2/2007 | Springs et al. |
| 2007/0203749 A1 | 8/2007 | Chunduru et al. |
| 2008/0241155 A1 | 10/2008 | Ni et al. |
| 2008/0248046 A1 | 10/2008 | Ni et al. |
| 2009/0226429 A1 | 9/2009 | Salcedo et al. |
| 2010/0016218 A1 | 1/2010 | Lichter et al. |

(Continued)

FOREIGN PATENT DOCUMENTS

| | | |
|---|---|---|
| AU | 2011259844 B2 | 11/2012 |
| CN | 104634852 A | 5/2015 |

(Continued)

OTHER PUBLICATIONS

Houghton et al. Pediatr. Blood Cancer, 2012, vol. 58, pp. 636-639.*
Beug et al, "Interferon-mediated potentiation of SMAC mimetic compound cytotoxicity by oncolytic virotherapy," Cytokine 63:248, Abstract 21 (2013).
Brun et al., "Identification of genetically modified Maraba virus as an oncolytic rhabdovirus," Mol Ther. 18(8):1440-9 (2010).
Crawford et al., "SAHA overcomes FLIP-mediated inhibition of SMAC mimetic-induced apoptosis in mesothelioma," Cell Death Dis. 4:e733 (2013) (11 pages).
International Preliminary Report on Patentability for International Patent Application No. PCT/CA2015/000043, dated Jul. 26, 2016 (8 pages).

(Continued)

Primary Examiner — Samira J Jean-Louis
(74) Attorney, Agent, or Firm — Clark & Elbing LLP

(57) ABSTRACT

The present invention includes methods and compositions for enhancing the efficacy of SMCs in the treatment of cancer. In particular, the present invention includes methods and compositions for combination therapies that include an SMC and at least a second agent that stimulates one or more apoptotic or immune pathways. The second agent may be, e.g., an immunostimulatory compound or oncolytic virus.

6 Claims, 35 Drawing Sheets

(56) References Cited

U.S. PATENT DOCUMENTS

| | | |
|---|---|---|
| 2010/0074863 A1 | 3/2010 | Or et al. |
| 2010/0135951 A1 | 6/2010 | Zhou et al. |
| 2010/0179163 A1 | 7/2010 | Kung et al. |
| 2010/0256046 A1 | 10/2010 | Springs et al. |
| 2011/0104143 A1 | 5/2011 | Buchsbaum et al. |
| 2011/0183358 A1 | 7/2011 | Reed et al. |
| 2011/0305777 A1 | 12/2011 | Condon et al. |
| 2013/0196927 A1 | 8/2013 | Benetatos et al. |
| 2014/0057924 A1 | 2/2014 | Wang et al. |
| 2014/0127271 A1 | 5/2014 | Sill et al. |
| 2014/0271688 A1 | 9/2014 | Abrams et al. |
| 2014/0303090 A1 | 10/2014 | Condon et al. |
| 2014/0341920 A1 | 11/2014 | Noelle |
| 2015/0010613 A1 | 1/2015 | Dubensky, Jr. et al. |
| 2015/0110779 A1 | 4/2015 | Shahabi et al. |
| 2015/0119288 A1 | 4/2015 | Soper et al. |
| 2015/0125447 A1 | 5/2015 | Heider |
| 2015/0141273 A1 | 5/2015 | Bosch et al. |
| 2015/0202273 A1 | 7/2015 | Wang |
| 2015/0250853 A1 | 9/2015 | Mak |
| 2015/0284416 A1 | 10/2015 | Zhao |
| 2015/0322155 A1 | 11/2015 | Zhao |
| 2016/0051672 A1 | 2/2016 | Stewart et al. |
| 2016/0067337 A1 | 3/2016 | Barnhart et al. |
| 2016/0125127 A1 | 5/2016 | Sarkar et al. |
| 2016/0177276 A1 | 6/2016 | Lo et al. |
| 2016/0184383 A1 | 6/2016 | Lalaoui et al. |
| 2016/0312297 A1 | 10/2016 | Ayers et al. |
| 2016/0317605 A1 | 11/2016 | Seneci et al. |
| 2016/0346408 A1 | 12/2016 | Kelsen et al. |
| 2017/0042920 A1 | 2/2017 | Bantia |
| 2017/0095473 A1 | 4/2017 | Molineaux et al. |
| 2017/0106048 A1 | 4/2017 | Kunz et al. |
| 2017/0106067 A1 | 4/2017 | Jaffee et al. |
| 2017/0114137 A1 | 4/2017 | Li |
| 2017/0119807 A1 | 5/2017 | Lee et al. |
| 2017/0119877 A1 | 5/2017 | Green et al. |
| 2017/0121421 A1 | 5/2017 | Cortez et al. |
| 2017/0158776 A1 | 6/2017 | Feltquate et al. |
| 2017/0182001 A1 | 6/2017 | Shyur et al. |
| 2017/0196879 A1 | 7/2017 | Pache et al. |
| 2017/0209574 A1 | 7/2017 | Cao et al. |
| 2017/0224836 A1 | 8/2017 | Bialucha et al. |
| 2017/0239347 A1 | 8/2017 | Korneluk et al. |
| 2017/0240639 A1 | 8/2017 | Kumar et al. |
| 2017/0274073 A1 | 9/2017 | Grogan et al. |
| 2017/0283408 A1 | 10/2017 | Lu et al. |

FOREIGN PATENT DOCUMENTS

| | | |
|---|---|---|
| CN | 104975063 A | 10/2015 |
| CN | 105566447 A | 5/2016 |
| CN | 105585583 A | 5/2016 |
| CN | 105617400 A | 6/2016 |
| CN | 105777632 A | 7/2016 |
| CN | 106153939 A | 11/2016 |
| CN | 106265764 A | 1/2017 |
| CN | 106710510 A | 5/2017 |
| EP | 1633336 A2 | 3/2006 |
| EP | 2116602 A1 | 11/2009 |
| EP | 2438813 A1 | 4/2012 |
| EP | 3067062 A1 | 9/2016 |
| EP | 3150224 A1 | 4/2017 |
| JP | 4203144 B2 | 12/2008 |
| KR | 20120050728 A | 5/2012 |
| TW | 201347760 A | 12/2013 |
| UA | 71889 C2 | 1/2005 |
| WO | WO-98/22131 A2 | 5/1998 |
| WO | WO-98/35693 A2 | 8/1998 |
| WO | WO-98/53091 A1 | 11/1998 |
| WO | WO-00/05366 A2 | 2/2000 |
| WO | WO-02/16402 A2 | 2/2002 |
| WO | WO-02/26968 A2 | 4/2002 |
| WO | WO-03/106460 A1 | 12/2003 |
| WO | WO-2004/005248 A1 | 1/2004 |
| WO | WO-2004/017991 A1 | 3/2004 |
| WO | WO-2004/031144 A2 | 4/2004 |
| WO | WO-2004/050895 A2 | 6/2004 |
| WO | WO-2004/072105 A2 | 8/2004 |
| WO | WO-2004/085682 A2 | 10/2004 |
| WO | WO-2005/009287 A2 | 2/2005 |
| WO | WO-2005/040391 A1 | 5/2005 |
| WO | WO-2005/069894 A2 | 8/2005 |
| WO | WO-2005/074989 A2 | 8/2005 |
| WO | WO-2005/097791 A1 | 10/2005 |
| WO | WO-2006/010118 A2 | 1/2006 |
| WO | WO-2006/014361 A1 | 2/2006 |
| WO | WO-2006/017295 A2 | 2/2006 |
| WO | WO-2006/047250 A2 | 5/2006 |
| WO | WO-2006/060898 A1 | 6/2006 |
| WO | WO-2006/124477 A2 | 11/2006 |
| WO | WO-2006/128455 A2 | 12/2006 |
| WO | WO-2006/133147 A2 | 12/2006 |
| WO | WO-2007/075525 A2 | 7/2007 |
| WO | WO-2007/101347 A1 | 9/2007 |
| WO | WO-2007/130626 A2 | 11/2007 |
| WO | WO-2007/131366 A2 | 11/2007 |
| WO | WO-2008/014229 A2 | 1/2008 |
| WO | WO-2008/014236 A1 | 1/2008 |
| WO | WO-2008/014238 A2 | 1/2008 |
| WO | WO-2008/014240 A2 | 1/2008 |
| WO | WO-2008/017121 A1 | 2/2008 |
| WO | WO-2008/017123 A1 | 2/2008 |
| WO | WO-2008/045905 A1 | 4/2008 |
| WO | WO-2008/051243 A2 | 5/2008 |
| WO | WO-2008/057172 A2 | 5/2008 |
| WO | WO-2008/067280 A2 | 6/2008 |
| WO | WO-2008/109057 A1 | 9/2008 |
| WO | WO-2008/124129 A2 | 10/2008 |
| WO | WO-2008/128171 A2 | 10/2008 |
| WO | WO-2008/140794 A1 | 11/2008 |
| WO | WO-2009/044172 A1 | 4/2009 |
| WO | WO-2009/070689 A1 | 6/2009 |
| WO | WO-2009/089502 A1 | 7/2009 |
| WO | WO-2009/094287 A1 | 7/2009 |
| WO | WO-2009/098701 A1 | 8/2009 |
| WO | WO-2009/126947 A2 | 10/2009 |
| WO | WO-2009/140447 A1 | 11/2009 |
| WO | WO-2010/017035 A2 | 2/2010 |
| WO | WO-2010/033315 A1 | 3/2010 |
| WO | WO-2010/063011 A2 | 6/2010 |
| WO | WO-2010/077589 A2 | 7/2010 |
| WO | WO-2010/086722 A1 | 8/2010 |
| WO | WO-2010/142994 A1 | 12/2010 |
| WO | WO-2011/019782 A1 | 2/2011 |
| WO | WO-2011/035083 A1 | 3/2011 |
| WO | WO-2011/050068 A2 | 4/2011 |
| WO | WO-2011/082285 A1 | 7/2011 |
| WO | WO-2011/116344 A2 | 9/2011 |
| WO | WO-2011/153514 A2 | 12/2011 |
| WO | WO-2012/052758 A1 | 4/2012 |
| WO | WO-2013/043591 A1 | 3/2013 |
| WO | WO-2013/079174 A1 | 6/2013 |
| WO | WO-2014/043708 A1 | 3/2014 |
| WO | WO-2014/066834 A1 | 5/2014 |
| WO | WO-2014/071231 A1 | 5/2014 |
| WO | WO-2014/083178 A1 | 6/2014 |
| WO | WO-2014/085489 A1 | 6/2014 |
| WO | WO-2014/127917 A1 | 8/2014 |
| WO | WO-2014/145613 A2 | 9/2014 |
| WO | WO-2014/160160 A2 | 10/2014 |
| WO | WO-2014/163714 A2 | 10/2014 |
| WO | WO-2014/189805 A1 | 11/2014 |
| WO | WO-2014/193898 A1 | 12/2014 |
| WO | WO-2014/194312 A2 | 12/2014 |
| WO | WO-2014/205516 A1 | 12/2014 |
| WO | WO-2015/017520 A1 | 2/2015 |
| WO | WO-2015/017788 A1 | 2/2015 |
| WO | WO-2015/049280 A1 | 4/2015 |
| WO | WO-2015/054593 A1 | 4/2015 |
| WO | WO-2015/069697 A2 | 5/2015 |
| WO | WO-2015/069770 A1 | 5/2015 |
| WO | WO-2015/075557 A2 | 5/2015 |
| WO | WO-2015/077414 A1 | 5/2015 |

(56) References Cited

FOREIGN PATENT DOCUMENTS

| | | |
|---|---|---|
| WO | WO-2015/090572 A1 | 6/2015 |
| WO | WO-2015/092420 A1 | 6/2015 |
| WO | WO-2015/095410 A1 | 6/2015 |
| WO | WO-2015/095423 A2 | 6/2015 |
| WO | WO-2015/095811 A2 | 6/2015 |
| WO | WO-2015/103431 A1 | 7/2015 |
| WO | WO-2015/109391 A1 | 7/2015 |
| WO | WO-2015/127501 A1 | 9/2015 |
| WO | WO-2015/142675 A2 | 9/2015 |
| WO | WO-2015/151078 A2 | 10/2015 |
| WO | WO-2015/151079 A2 | 10/2015 |
| WO | WO-2015/151080 A2 | 10/2015 |
| WO | WO-2015/172128 A1 | 11/2015 |
| WO | WO-2015/175334 A2 | 11/2015 |
| WO | WO-2016/004218 A1 | 1/2016 |
| WO | WO-2016/011160 A1 | 1/2016 |
| WO | WO-2016/012615 A1 | 1/2016 |
| WO | WO-2016/020791 A1 | 2/2016 |
| WO | WO-2016/024228 A1 | 2/2016 |
| WO | WO-2016/024231 A1 | 2/2016 |
| WO | WO-2016/040892 A1 | 3/2016 |
| WO | WO-2016/044189 A1 | 3/2016 |
| WO | WO-2016/054555 A2 | 4/2016 |
| WO | WO-2016/061142 A1 | 4/2016 |
| WO | WO-2016/061231 A1 | 4/2016 |
| WO | WO-2016/063233 A1 | 4/2016 |
| WO | WO-2016/073759 A1 | 5/2016 |
| WO | WO-2016/079527 A1 | 5/2016 |
| WO | WO-2016/087680 A1 | 6/2016 |
| WO | WO-2016/097773 A1 | 6/2016 |
| WO | WO-2016/128912 A1 | 8/2016 |
| WO | WO-2016/130502 A1 | 8/2016 |
| WO | WO-2016/130839 A1 | 8/2016 |
| WO | WO-2016/132366 A1 | 8/2016 |
| WO | WO-2016/137730 A1 | 9/2016 |
| WO | WO-2016/137985 A1 | 9/2016 |
| WO | WO-2016/141209 A1 | 9/2016 |
| WO | WO-2016/146035 A1 | 9/2016 |
| WO | WO-2016/160966 A1 | 10/2016 |
| WO | WO-2016/160972 A1 | 10/2016 |
| WO | WO-2016/161347 A1 | 10/2016 |
| WO | WO-2016/162867 A1 | 10/2016 |
| WO | WO-2016/169989 A1 | 10/2016 |
| WO | WO-2016/172134 A2 | 10/2016 |
| WO | WO-2016/172583 A1 | 10/2016 |
| WO | WO-2016/189326 A1 | 12/2016 |
| WO | WO-2016/191397 A1 | 12/2016 |
| WO | WO-2016/203432 A1 | 12/2016 |
| WO | WO-2016/204193 A1 | 12/2016 |
| WO | WO-2016/205320 A1 | 12/2016 |
| WO | WO-2017/004165 A1 | 1/2017 |
| WO | WO-2017/011590 A1 | 1/2017 |
| WO | WO-2017/011623 A1 | 1/2017 |
| WO | WO-2017/011670 A1 | 1/2017 |
| WO | WO-2017/015442 A1 | 1/2017 |
| WO | WO-2017/019894 A1 | 2/2017 |
| WO | WO-2017/019897 A1 | 2/2017 |
| WO | WO-2017/023793 A2 | 2/2017 |
| WO | WO-2017/024296 A1 | 2/2017 |
| WO | WO-2017/025496 A1 | 2/2017 |
| WO | WO-2017/031367 A1 | 2/2017 |
| WO | WO-2017/040660 A1 | 3/2017 |
| WO | WO-2017/040666 A2 | 3/2017 |
| WO | WO-2017/042634 A2 | 3/2017 |
| WO | WO-2017/046747 A1 | 3/2017 |
| WO | WO-2017/053823 A1 | 3/2017 |
| WO | WO-2017/059224 A2 | 4/2017 |
| WO | WO-2017/060650 A1 | 4/2017 |
| WO | WO-2017/070110 A1 | 4/2017 |
| WO | WO-2017/070137 A1 | 4/2017 |
| WO | WO-2017/075052 A1 | 5/2017 |
| WO | WO-2017/079080 A1 | 5/2017 |
| WO | WO-2017/079283 A1 | 5/2017 |
| WO | WO-2017/079297 A1 | 5/2017 |
| WO | WO-2017/079431 A1 | 5/2017 |
| WO | WO-2017/082186 A1 | 5/2017 |
| WO | WO-2017/087857 A1 | 5/2017 |
| WO | WO-2017/106656 A1 | 6/2017 |
| WO | WO-2017/112940 A1 | 6/2017 |
| WO | WO-2017/112943 A1 | 6/2017 |
| WO | WO-2017/114497 A1 | 7/2017 |
| WO | WO-2017/120445 A1 | 7/2017 |
| WO | WO-2017/123981 A1 | 7/2017 |
| WO | WO-2017/125532 A1 | 7/2017 |
| WO | WO-2017/127282 A1 | 7/2017 |
| WO | WO-2017/129763 A1 | 8/2017 |
| WO | WO-2017/133175 A1 | 8/2017 |
| WO | WO-2017/133706 A1 | 8/2017 |
| WO | WO-2017/141049 A1 | 8/2017 |
| WO | WO-2017/141243 A1 | 8/2017 |
| WO | WO-2017/143071 A1 | 8/2017 |
| WO | WO-2017/143115 A2 | 8/2017 |
| WO | WO-2017/143237 A1 | 8/2017 |
| WO | WO-2017/143449 A1 | 8/2017 |
| WO | WO-2017/144877 A1 | 8/2017 |

OTHER PUBLICATIONS

International Search Report and Written Opinion for International Application No. PCT/CA2015/000043, dated Apr. 30, 2015 (12 pages).

Lemay et al., "Harnessing oncolytic virus-mediated antitumor immunity in an infected cell vaccine," Mol Ther. 20(9):1791-9 (2012).

Lu et al., "Therapeutic potential and molecular mechanism of a novel, potent, nonpeptide, Smac mimetic SM-164 in combination with Trail for cancer treatment," Mol Cancer Ther. 10(5):902-14 (2011).

Beug et al., "Combinatorial cancer immunotherapy strategies with proapoptotic small-molecule IAP antagonists," Int J Dev Biol. 59(1-3):141-7 (2015).

Beug et al., "Smac mimetics synergize with immune checkpoint inhibitors to promote tumour immunity against glioblastoma," Nat Commun. 8:14278 (2017) (29 pages).

Beug et al., "Smac mimetics combined with innate immune stimuli create the perfect cytokine storm to kill tumor cells," Oncoimmunology. 3:e28541 (2014) (3 pages).

Beug et al., "Smac mimetics and innate immune stimuli synergize to promote tumor death," Nat Biotechnol. 32(2):182-90 (2014) (11 pages).

Vanneman et al., "Combining immunotherapy and targeted therapies in cancer treatment," Nat Rev Cancer. 12(4):237-51 (2012).

Knights et al., "Inhibitor of apoptosis protein (IAP) antagonists demonstrate divergent immunomodulatory properties in human immune subsets with implications for combination therapy," Cancer Immunol Immunother. 62(2):321-35 (2013).

"Debiopharm International SA Announces Clinical Collaboration with the Merck-Pfizer Alliance in Cancer Immunotherapy," Debiopharm Group Press Release, <https://www.debiopharm.com/debiopharm-international/press-releases/debiopharm-international-sa-announces-clinical-collaboration-with-the-merck-pfizer-alliance-in-cancer-immunotherapy/>, dated Oct. 20, 2016 (2 pages).

Tao et al., "Smac mimetic Debio 1143 and radiotherapy synergize to enhance antitumor immunity in lung cancer by targeting immunosuppressive cells," 106th Annual Meeting of the American Association for Cancer Research, Apr. 18-22, Philadelphia, Pennsylvania. Abstract 283 (2015) (1 page).

Barkhouse et al., "The SMAC mimetic Debio 1143 synergizes with radiotherapy and immune checkpoint inhibitors to enhance antitumor immunity," AACR-NCI-EORTC International Conference on Molecular Targets and Cancer Therapeutics, Nov. 5-9, Boston, Massachusetts. Abstract A93 (2015) (1 page).

LaCasse et al., "Abstract B034: Smac mimetics synergistically improve the efficacy of cancer immunotherapies including immune checkpoint blockade in preclinical models," Cancer Immunol Res. 4(11 Suppl.): Abstract B034 (2016) (2 pages).

LaCasse et al., "The inhibitors of apoptosis (IAPs): Over 20 years of research into life and death," Semin Cell Dev Biol. 39:70-1 (2015).

(56) References Cited

OTHER PUBLICATIONS

Fulda, "Targeting extrinsic apoptosis in cancer: Challenges and opportunities," Semin Cell Dev Biol. 39:20-5 (2015).

* cited by examiner

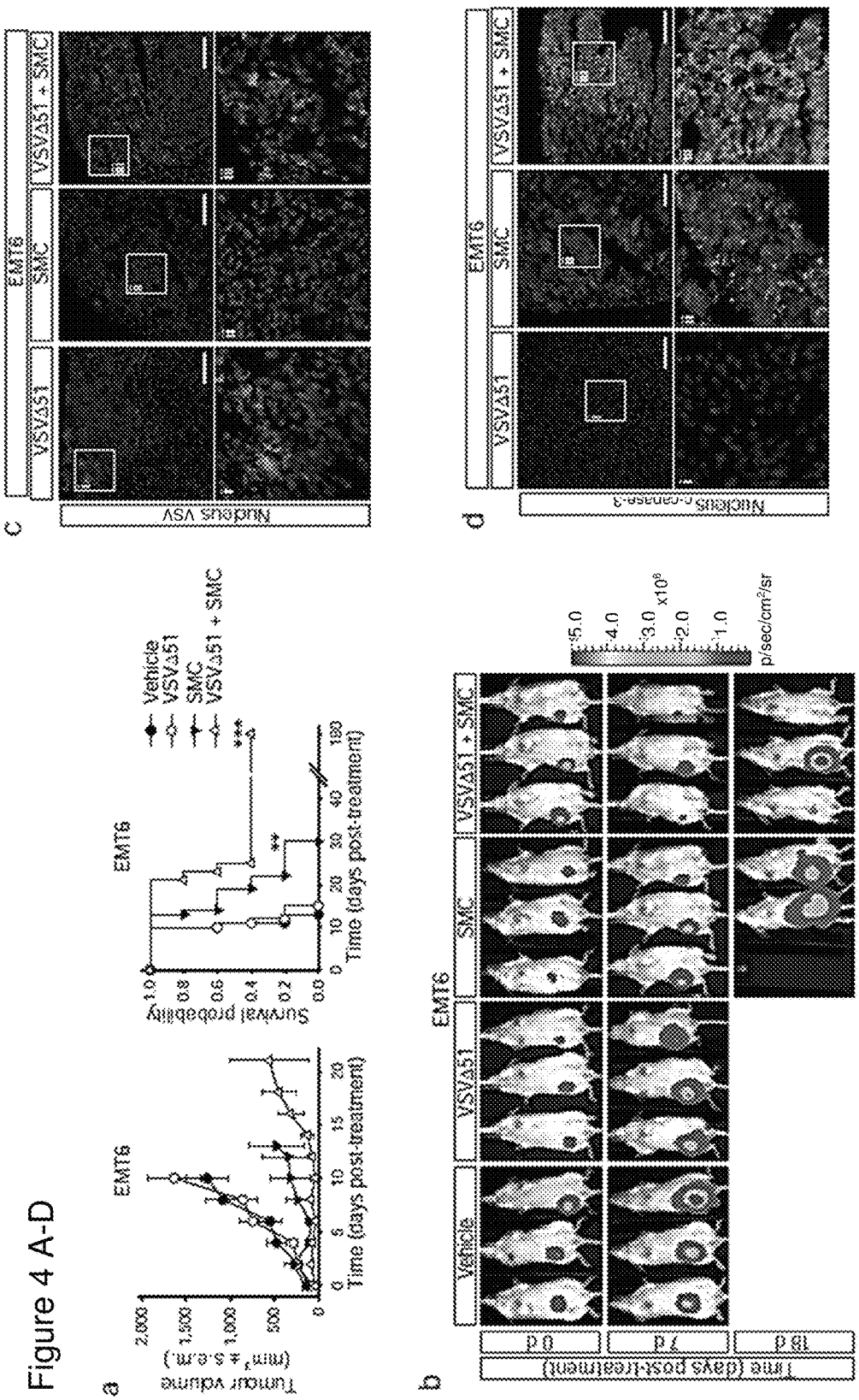
Figure 4 A-D

Figure 4 E-G
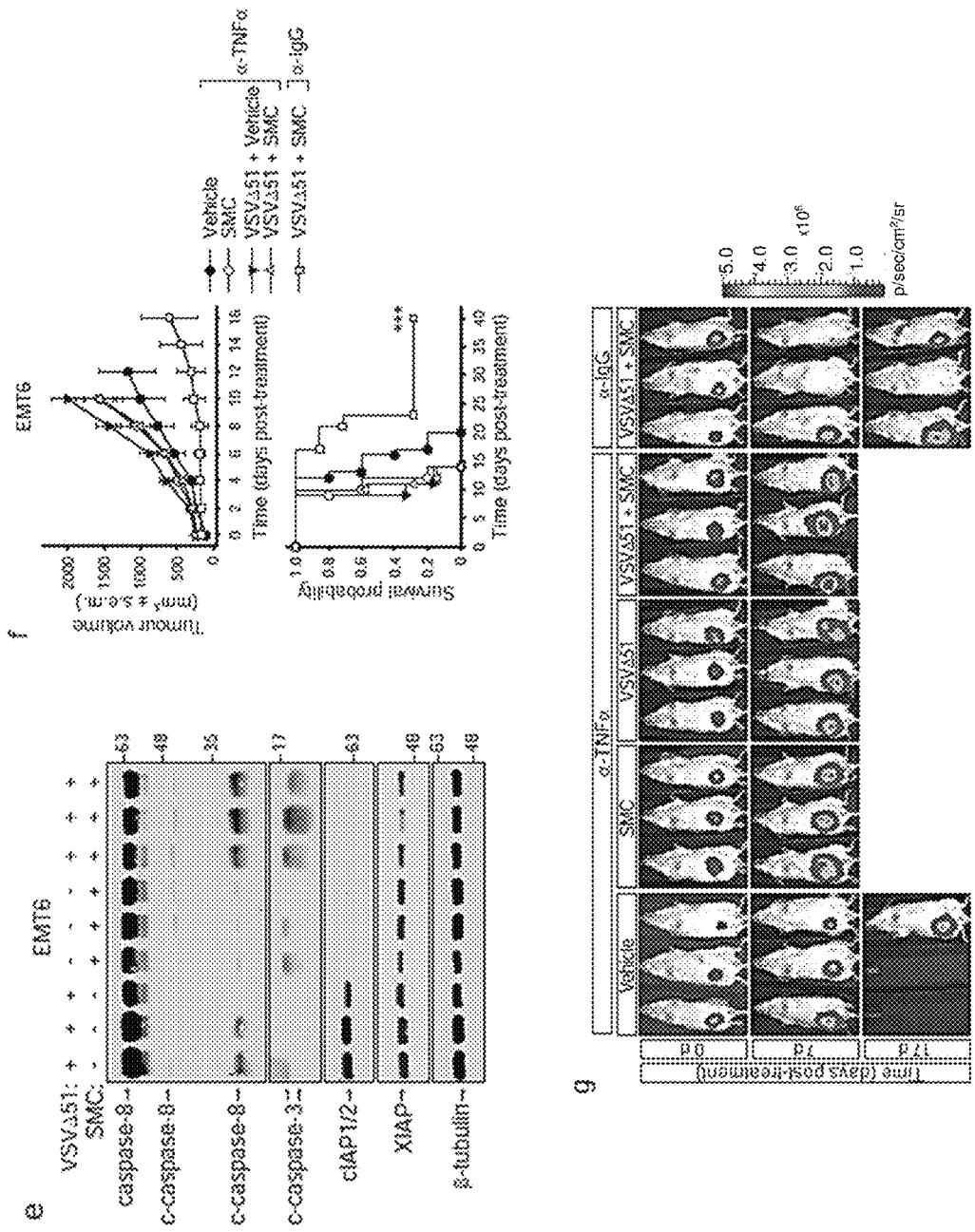

Figure 5
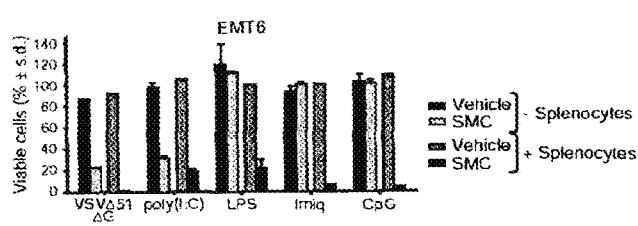
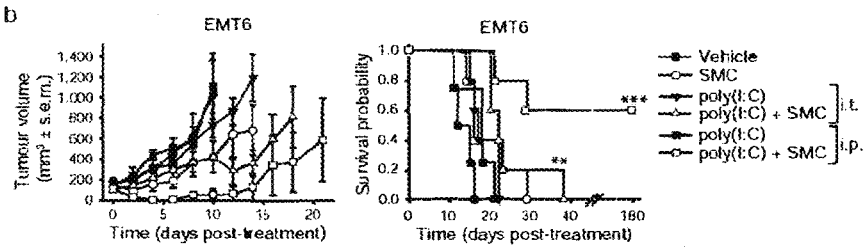
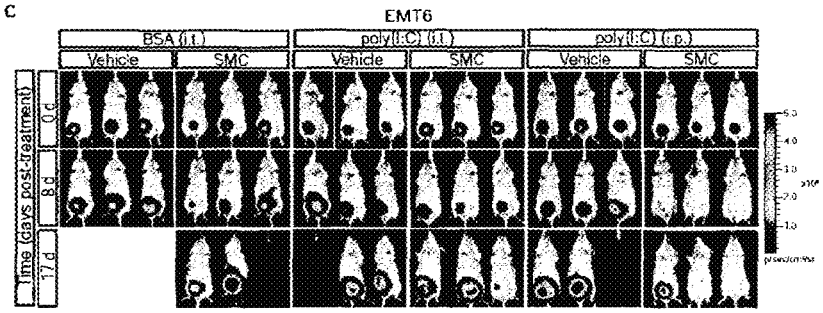
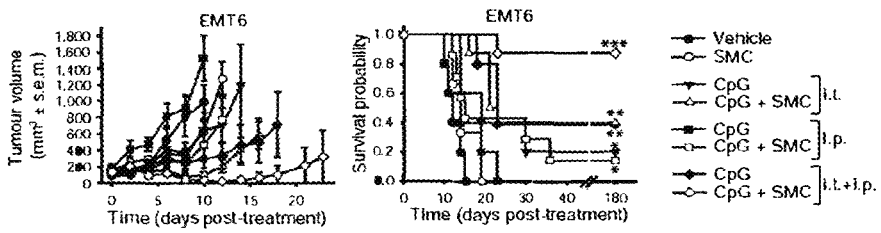
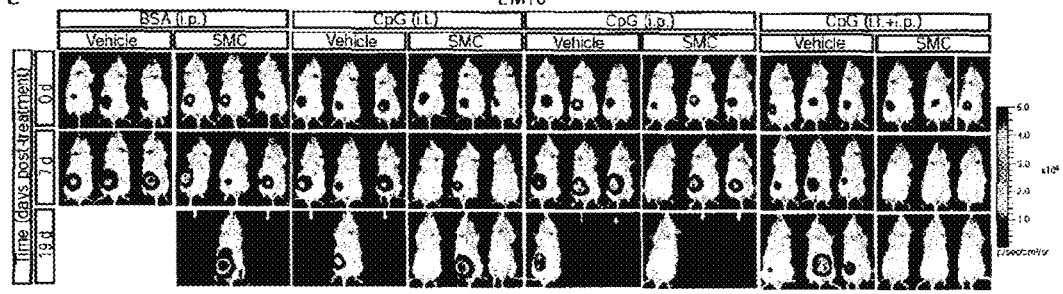

SMC COMBINATION THERAPY FOR THE TREATMENT OF CANCER

BACKGROUND OF THE INVENTION

The death of cells by apoptosis (or programmed cell death), and other cell death pathways, is regulated by various cellular mechanisms. Inhibitor of apoptosis (IAP) proteins, such as X-linked IAP (XIAP) or cellular IAP proteins 1 and 2 (cIAP1 and 2), are regulators of programmed cell death, including (but not limited to) apoptosis pathways, e.g., in cancer cells. Other forms of cell death could include, but are not limited to, necroptosis, necrosis, pyroptosis, and immunogenic cell death. In addition, these IAPs regulate various cell signaling pathways through their ubiquitin E3 ligase activity, which may or may not be related to cell survival. Another regulator of apoptosis is the polypeptide Smac. Smac is a proapoptotic protein released from mitochondria in conjunction with cell death. Smac can bind to IAPs, antagonizing their function. Smac mimetic compounds (SMCs) are non-endogenous proapoptotic compounds capable of carrying out one or more of the functions or activities of endogenous Smac.

The prototypical XIAP protein directly inhibits key initiator and executioner caspase proteins within apoptosis cascades. XIAP can thereby thwart the completion of apoptotic programs. Cellular IAP proteins 1 and 2 are E3 ubiquitin ligases that regulate apoptotic signaling pathways engaged by immune cytokines. The dual loss of cIAP1 and 2 can cause TNFα, TRAIL, and/or IL-1β to become toxic to, e.g., the majority of cancer cells. SMCs may inhibit XIAP, cIAP1, cIAP2, or other IAPs, and/or contribute to other proapoptotic mechanisms.

Treatment of cancer by the administration of SMCs has been proposed. However, SMCs alone may be insufficient to treat certain cancers. There exists a need for methods of treating cancer that improve the efficacy of SMC treatment in one or more types of cancer.

SUMMARY OF THE INVENTION

The present invention includes compositions and methods for the treatment of cancer by the administration of an SMC and an immunostimulatory, or immunomodulatory, agent. SMCs and immunostimulatory agents are described herein, including, without limitation, the SMCs of Table 1 and the immunostimulatory agents of Tables 2 and 3.

One aspect of the present invention is a composition including an SMC from Table 1 and an immunostimulatory agent from Table 2 or Table 3, such that the SMC and the immunostimulatory agent are provided in amounts that together are sufficient to treat cancer when administered to a patient in need thereof.

Another aspect of the present invention is a method for treating a patient diagnosed with cancer, the method including administering to the patient an SMC from Table 1 and an immunostimulatory agent from Table 2 or Table 3, such that the SMC and the immunostimulatory agent are administered simultaneously or within 28 days of each other in amounts that together are sufficient to treat the cancer.

In some embodiments, the SMC and the immunostimulatory agent are administered within 14 days of each other, within 10 days of each other, within 5 days of each other, within 24 hours of each other, within 6 hours of each other, or simultaneously.

In particular embodiments, the SMC is a monovalent SMC, such as LCL161, SM-122, GDC-0152/RG7419, GDC-0917/CUDC-427, or SM-406/AT-406/Debio1143. In other embodiments, the SMC is a bivalent SMC, such as AEG40826/HGS1049, OICR720, TL32711/Birinapant, SM-1387/APG-1387, or SM-164.

In particular embodiments, the immunostimulatory agent is a TLR agonist from Table 2. In certain embodiments, the immunostimulatory agent is a lipopolysaccharide, peptidoglycan, or lipopeptide. In other embodiments, the immunostimulatory agent is a CpG oligodeoxynucleotide, such as CpG-ODN 2216. In still other embodiments, the immunostimulatory agent is imiquimod or poly(I:C).

In particular embodiments, the immunostimulatory agent is a virus from Table 3. In certain embodiments, the immunostimulatory agent is a vesicular stomatitis virus (VSV), such as VSV-M51R, VSV-MΔ51, VSV-IFNβ, or VSV-IFNβ-NIS. In other embodiments, the immunostimulatory agent is an adenovirus, maraba vesiculovirus, reovirus, rhabdovirus, or vaccinia virus, or a variant thereof. In some embodiments, the immunostimulatory agent is a Talimogene laherparepvec.

In some embodiments, a composition or method of the present invention includes a plurality of immunostimulatory or immunomodulatory agents, including but not limited to interferons, and/or a plurality of SMCs.

In some embodiments, a composition or method of the present invention includes one or more interferon agents, such as an interferon type 1 agent, an interferon type 2 agent, and/or an interferon type 3 agent.

In any method of the present invention, the cancer can be a cancer that is refractory to treatment by an SMC in the absence of an immunostimulatory or immunomodulatory agent. In any method of the present invention, the treatment can further include administration of a therapeutic agent including an interferon.

In any method of the present invention, the cancer can be a cancer that is selected from adrenal cancer, basal cell carcinoma, biliary tract cancer, bladder cancer, bone cancer, brain cancer, breast cancer, cervical cancer, choriocarcinoma, colon cancer, colorectal cancer, connective tissue cancer, cancer of the digestive system, endometrial cancer, epipharyngeal carcinoma, esophageal cancer, eye cancer, gallbladder cancer, gastric cancer, cancer of the head and neck, hepatocellular carcinoma, intra-epithelial neoplasm, kidney cancer, laryngeal cancer, leukemia, liver cancer, liver metastases, lung cancer, lymphoma, melanoma, myeloma, multiple myeloma, neuroblastoma, mesothelioma, neuroglioma, myelodysplastic syndrome, multiple myeloma, oral cavity cancer, ovarian cancer, paediatric cancer, pancreatic cancer, pancreatic endocrine tumors, penile cancer, plasma cell tumors, pituitary adenoma, thymoma, prostate cancer, renal cell carcinoma, cancer of the respiratory system, rhabdomyosarcoma, salivary gland cancer, sarcoma, skin cancer, small bowel cancer, stomach cancer, testicular cancer, thyroid cancer, ureteral cancer, and cancer of the urinary system.

The invention further includes a composition including an SMC from Table 1 and an immunostimulatory agent. The immunostimulatory agent may include a killed virus, an inactivated virus, or a viral vaccine, such that the SMC and the immunostimulatory agent are provided in amounts that together are sufficient to treat cancer when administered to a patient in need thereof. In particular embodiments, the said immunostimulatory agent is a NRRP or a rabies vaccine. In other embodiments, the invention includes a composition including an SMC from Table 1 and an immunostimulatory agent. The immunostimulatory agent may include a first agent that primes an immune response and at least a second agent that boosts the immune response, such that the SMC and the said immunostimulatory agent are provided in amounts that together are sufficient to treat cancer when administered to a patient in need thereof. In certain embodiments, one or both of the first agent and the second agent is an oncolytic virus vaccine. In other particular embodiments, the first agent is an adenovirus carrying a tumor antigen and the second agent is a vesiculovirus, such as a Maraba-MG1 carrying the same tumor antigen as the adenovirus or a Maraba-MG1 that does not carry a tumor antigen.

"Neighboring" cell means a cell sufficiently proximal to a reference cell to directly or indirectly receive an immune, inflammatory, or proapoptotic signal from the reference cell.

"Potentiating apoptosis or cell death" means to increase the likelihood that one or more cells will apoptose or die. A treatment may potentiate cell death by increasing the likelihood that one or more treated cells will apoptose, and/or by increasing the likelihood that one or more cells neighboring a treated cell will apoptose or die.

"Endogenous Smac activity" means one or more biological functions of Smac that result in the potentiation of apoptosis, including at least the inhibition of cIAP1 and cIAP2. It is not required that the biological function occur or be possible in all cells under all conditions, only that Smac is capable of the biological function in some cells under certain naturally occurring in vivo conditions.

"Smac mimetic compound" or "SMC" means a composition of one or more components, e.g., a small molecule, compound, polypeptide, protein, or any complex thereof, capable of inhibiting cIAP1 and/or inhibiting cIAP2. Smac mimetic compounds include the compounds listed in Table 1. To "induce an apoptotic program" means to cause a change in the proteins or protein profiles of one or more cells such that the amount, availability, or activity of one or more proteins capable of participating in an IAP-mediated apoptotic pathway is increased, or such that one or more proteins capable of participating in an IAP-mediated apoptotic pathway are primed for participation in the activity of such a pathway. Inducing an apoptotic program does not require the initiation of cell death per se: induction of a program of apoptosis in a manner that does not result in cell death may synergize with treatment with an SMC that potentiates apoptosis, leading to cell death.

"Immunostimulatory agent" means a composition of one or more components cumulatively capable of inducing an apoptotic or inflammatory program in one or more cells of a subject, and cell death downstream of this program being inhibited by at least cIAP1 and cIAP2. An immunostimulatory agent may be, e.g., a TLR agonist (e.g., a compound listed in Table 2) or a virus (e.g., a virus listed in Table 3), such as an oncolytic virus.

"Treating cancer" means to induce the death of one or more cancer cells in a subject, or to provoke an immune response which could lead to tumor regression and block tumor spread (metastasis). Treating cancer may completely or partially abolish some or all of the signs and symptoms of cancer in a subject, decrease the severity of one or more symptoms of cancer in a subject, lessen the progression of one or more symptoms of cancer in a subject, or mediate the progression or severity of one or more subsequently developed symptoms.

"Prodrug" means a therapeutic agent that is prepared in an inactive form that may be converted to an active form within the body of a subject, e.g. within the cells of a subject, by the action of one or more enzymes, chemicals, or conditions present within the subject.

By a "low dosage" or "low concentration" is meant at least 5% less (e.g., at least 10%, 20%, 50%, 80%, 90%, or even 95%) than the lowest standard recommended dosage or lowest standard recommended concentration of a particular compound formulated for a given route of administration for treatment of any human disease or condition.

By a "high dosage" is meant at least 5% (e.g., at least 10%, 20%, 50%, 100%, 200%, or even 300%) more than the highest standard recommended dosage of a particular compound for treatment of any human disease or condition.

BRIEF DESCRIPTION OF THE DRAWINGS

FIG. 1a is a pair of graphs showing the results of Alamar blue viability assays of cells treated with LCL161 and increasing MOIs of VSVΔ51. Error bars, mean±s.d. FIG. 1b is a set of micrographs of cells treated with LCL161 and 0.1 MOI of VSVΔ51-GFP. FIG. 1c is a pair of graphs showing viability (Alamar Blue) of cells infected with VSVΔ51 (0.1 MOI) in the presence of increasing concentrations of LCL161. Error bars, mean±s.d. FIG. 1d is a pair of graphs showing data from cells that were infected with VSVΔ51 for 24 hours. Cell culture supernatant was exposed to virus-inactivating UV light and then media was applied to new cells for viability assays (Alamar Blue) in the presence of LCL161. Error bars, mean±s.d. FIG. 1e is a graph showing the viability of cells co-treated with LCL161 and non-spreading virus VSVΔ51ΔG (0.1 MOI). Error bars, mean±s.d. FIG. 1f is a graph and a pair of images relating to cells that were overlaid with agarose media containing LCL161, inoculated with VSVΔ51-GFP in the middle of the well, and infectivity measured by fluorescence and cytotoxicity was assessed by crystal violet staining (images were superimposed; non-superimposed images are in FIG. 11). Error bars, mean±s.d.

FIG. 2a is a pair of graphs showing data from cells that were pretreated with LCL161 and infected with the indicated MOI of VSVΔ51. Virus titer was assessed by a standard plaque assay. FIG. 2b is a pair of graphs and a set of micrographs captured over time from cells that were treated with LCL161 and VSVΔ51-GFP. The graphs plot the number of GFP signals over time. Error bars, mean±s.d. n=12. FIG. 2c, is pair of graphs showing data from an experiment in which cell culture supernatants from LCL161 and VSVΔ51 treated cells were processed for the presence of IFNβ by ELISA. Error bars, mean±s.d. n=3. FIG. 2d is a pair of graphs showing data from an experiment in which cells were treated with LCL161 and VSVΔ51 for 20 hours and processed for RT-qPCR to measure interferon stimulated gene (ISG) expression. Error bars, mean±s.d. n=3. FIG. 2e is a pair of images showing immunoblots for STAT1 pathway activation performed on cells that were pretreated with LCL161 and subsequently stimulated with IFNβ.

FIG. 3a is a graph showing Alamar blue viability assay of cells transfected with combinations of nontargeting (NT), TNF-R1 and DR5 siRNA and subsequently treated with LCL161 and VSVΔ51 (0.1 MOI or IFNβ. Error bars, mean±s.d. FIG. 3b is a graph showing the viability of cells transfected with NT or IFNAR1 siRNA and subsequently treated with LCL161 and VSVΔ51ΔG. Error bars, mean±s.d. FIG. 3c is a graph showing data from an experiment in which cells were pretreated with LCL161, infected with 0.5 MOI of VSVΔ51, and cytokine gene expression was measured by RT-qPCR. Error bars, mean±s.d. FIG. 3d is a chart showing data collected from an experiment in which cytokine ELISAs were performed on cells transfected with NT or IFNAR1 siRNA and subsequently treated with LCL161 and 0.1 MOI of VSVΔ51. Error bars, mean±s.d. FIG. 3e is a graph showing the viability of cells co-treated with LCL161 and cytokines. Error bars, mean±s.d. FIG. 3f is a graph showing data from an experiment in which cells were pretreated with LCL161, stimulated with 250 U/mL (~20 pg/mL) IFNβ and cytokine mRNA levels were determined by RT-qPCR. Error bars, mean±s.d. FIG. 3g is a pair of graphs showing the results of cytokine ELISAs conducted on cells treated with LCL161 and 0.1 MOI of VSVΔ51. FIG. 3h is a graph showing the result of cytokine ELISAs performed on cells expressing IKKβ-DN and treated with LCL161 and VSVΔ51 or IFNβ. Error bars, mean±s.d.

FIGS. 4a-4g are a set of graphs and images showing that combinatorial SMC and OV treatment is efficacious in vivo and is dependent on cytokine signaling. FIG. 4a is a pair of graphs showing data from an experiment in which EMT6-Fluc tumors were treated with 50 mg/kg LCL161 (p.o.) and, 5×10⁸ PFU VSVΔ51 (i.v.). The left panel depicts tumor growth. The right panel represents the Kaplan-Meier curve depicting mouse survival. Error bars, mean±s.e.m. n=5 per group. Log-rank with Holm-Sidak multiple comparison: , p<0.01; *, p<0.001. Representative data from two independent experiments are shown. FIG. 4b is a series of representative IVIS images that were acquired from the experiment of FIG. 4a. FIGS. 4c and 4d are sets of immunofluorescence images of infection and apoptosis in 24 hour treated tumors using α-VSV or α-c-caspase-3 antibodies. FIG. 4e is an image showing an immunoblot in which protein lysates of tumors from the corresponding treated mice were immunoblotted with the indicated antibodies. FIG. 4f is a pair of graphs showing data from an experiment in which mice bearing EMT6-Fluc tumors were injected with neutralizing TNFα or isotype matched antibodies, and subsequently treated with 50 mg/kg LCL161 (p.o.) and 5×10⁸ PFU VSVΔ51 (i.v.). The left panel depicts tumor growth. The right panel represents the Kaplan-Meier curve depicting mouse survival. Error bars, mean±s.e.m. Vehicle α-TNFα, n=5; SMC α-TNFα, n=5; vehicle+VSVΔ51, n=5; α-TNFα, n=5; SMC+VSVΔ51 α-TNFα, n=7; SMC+VSVΔ51 α-IgG, n=7. Log-rank with Holm-Sidak multiple comparison: ***, p<0.001. FIG. 4g is a set of representative IVIS images that were acquired from the experiment of FIG. 4f.

FIGS. 5a-5e are a series of graphs and images showing that small molecule immune stimulators enhance SMC therapy in murine cancer models. FIG. 5a is a graph showing the results of Alamar blue viability assays of EMT6 cells which were co-cultured with splenocytes in a transwell system, and for which the segregated splenocytes were treated with LCL161 and the indicated TLR agonists. Error bars, mean±s.d. Representative data from at least three independent experiments using biological replicates (n=3) is shown. FIG. 5b is a pair of graphs showing the results of an experiment in which established EMT6-Fluc tumors were treated with SMC (50 mg/kg LCL161, p.o.) and poly(I:C) (15 ug i.t. or 2.5 mg/kg i.p.). The left panel depicts tumor growth. The right panel represents the Kaplan-Meier curve depicting mouse survival. Vehicle, vehicle+poly(I:C) i.p., n=4; remainder groups, n=5. Error bars, mean±s.e.m. Log-rank with Holm-Sidak multiple comparison: , p<0.01; *, p<0.001. FIG. 5c is a series of representative IVIS images that were acquired from the experiment of FIG. 5b. FIG. 5d is a pair of graphs showing the results of an experiment in which EMT6-Fluc tumors were treated with LCL161 or combinations of 200 μg (i.t.) and/or 2.5 mg/kg (i.p.) CpG ODN 2216. The left panel depicts tumor growth. The right panel represents the Kaplan-Meier curve depicting mouse survival. Vehicle, n=5; SMC, n=5; vehicle+CpG i.p., n=5; SMC+CpG i.p., n=7; vehicle+CpG i.t., n=5; SMC+CpG i.t., n=8; vehicle+CpG i.p.+i.t., n=5; SMC+CpG i.p.+i.t., n=8. Error bars, mean±s.e.m. Log-rank with Holm-Sidak multiple comparison: *, p<0.05; , p<0.01; *, p<0.001. FIG. 5e is a series of representative IVIS images that were acquired from the experiment of FIG. 5d.

FIG. 9a is a series of images showing the results of a virus spreading assay of cells that were overlaid with 0.7% agarose in the presence of vehicle or LCL161 and 500 PFU of the indicated viruses were dispensed in to the middle of the well. Cytotoxicity was assessed by crystal violet staining. Arrow denotes extension of the cell death zone from the origin of OV infection. FIG. 9b is a set of graphs showing the Alamar blue viability of cells treated with LCL161 and increasing MOIs of VSVΔ51 or Maraba-MG1. Error bars, mean±s.d. Representative data from two independent experiments using biological replicates (n=3) is shown.

FIG. 10a shows Alamar blue viability of cells transfected with nontargeting (NT) siRNA or siRNA targeting cIAP1, cIAP2 or XIAP, and subsequently treated with LCL161 and 0.1 MOI VSVΔ51 for 48 hours. Error bars, mean±s.d. Representative data from three independent experiments using biological replicates (n=3) is shown. FIG. 10b is a representative siRNA efficacy immunoblots for the experiment of FIG. 10a.

FIG. 12a is a set of images showing images from an experiment in which EMT6-bearing mice were treated with 50 mg/kg LCL161 (p.o.) and 5×10$^8$ PFU firefly luciferase tagged VSVΔ51 (VSVΔ51-Fluc) via i.v. injection. Virus distribution and replication was imaged at 24 and 48 hours using the IVIS. Red outline denotes region of tumors. Representative data from two independent experiments are shown. Arrow indicates spleen infected with VSVΔ51-Fluc. FIG. 12b is a graph showing data from an experiment in which tumors and tissues at 48 hour post-infection were homogenized and virus titrations were performed for each group. Error bars, mean±s.e.m.

FIG. 13a is an immunoblot showing knockdown in samples from the experiment of FIG. 3a. FIG. 13b is an immunoblot showing knockdown in samples from the experiment of FIG. 3b.

FIG. 14a is a pair of images of immunoblots in which immunoblotting for caspase and PARP activation was conducted on cells pretreated with LCL161 and subsequently treated with 1 MOI of VSVΔ51. FIG. 14b is a series of images showing micrographs of caspase activation that were acquired with cells that were co-treated with LCL161 and VSVΔ51 in the presence of the caspase-3/7 substrate DEVD-488. FIG. 14c is a graph in which the proportion of DEVD-488-positive cells from the experiment of FIG. 14b was plotted (n=12). Error bars, mean±s.d. FIG. 14d is a series of images from an experiment in which apoptosis was assessed by micrographs of translocated phosphatidyl serine (Annexin V-CF594, green) and loss of plasma membrane integrity (YOYO-1, blue) in cells treated with LCL161 and VSVΔ51. FIG. 14e is a graph in which the proportion of Annexin V-CF594-positive and YOYO-1-negative apoptotic cells from the experiment of FIG. 14d was plotted (n=9). Error bars, mean±s.d. FIG. 14f is a pair of graphs showing alamar blue viability of cells transfected with nontargeting (NT) siRNA or siRNA targeting caspase-8 or RIP1, and subsequently treated with LCL161 and 0.1 MOI of VSVΔ51 (n=3). Error bars, mean±s.d. FIG. 14g, is an image of an immunoblot showing representative siRNA efficacy for the experiment of FIG. 14f.

FIG. 15a is a pair of graphs showing Alamar blue viability assay of cells co-treated with 5 μM SMC and increasing MOIs of VSVΔ51-GFP or VSVΔ51-TNFα for 24 hours. Error bars, mean±s.d. FIG. 15b is a graph showing representative EC50 shifts from the experiment of FIG. 15a. The dose required to yield 50% viable cells in the presence in SMC versus vehicle was determined using nonlinear regression and plotted as EC50 shift. Representative data from three independent experiments using biological replicates (n=3).

FIG. 17a is a graph showing the results of an Alamar blue viability assay of EMT6 cells transfected with nontargeting (NT) or TNF-R1 siRNA and subsequently treated with LCL161 and VSVΔ51 (0.1 MOI) or IFNβ. Error bars, mean±s.d. FIG. 17b is a representative siRNA efficacy blot from the experiment of FIG. 17a. FIG. 17c is a graph showing the viability of EMT6 cells that were pretreated with TNFα neutralizing antibodies and subsequently treated with 5 μM SMC and VSVΔ51 or IFNβ.

FIG. 18a is a schematic showing that virus infection in refractory cancer cells leads to the production of Type 1 IFN, which subsequently induces expression of IFN stimulated genes, such as TRAIL. Type 1 IFN stimulation also leads to the NF-κB-dependent production of TNFα. IAP antagonism by SMC treatment leads to upregulation of TNFα and TRAIL expression and apoptosis of neighboring tumor cells. FIG. 18b is a schematic showing that infection of a single tumor cell results in the activation of innate antiviral Type 1 IFN pathway, leading to the secretion of Type 1 IFNs onto neighboring cells. The neighboring cells also produce the proinflammatory cytokines TNFα and TRAIL. The singly infected cell undergoes oncolysis and the remainder of the tumor mass remains intact. On the other hand, neighboring cells undergo bystander cell death due upon SMC treatment as a result of the SMC-mediated upregulation of TNFα/TRAIL and promotion of apoptosis upon proinflammatory cytokine activation.

FIG. 19a is graph showing weights from LCL161 treated mice female BALB/c mice (50 mg/kg LCL161, p.o.) that were recorded after a single treatment (day 0). n=5 per group. Error bars, mean±s.e.m. FIG. 19b is a blot of samples from an experiment in which EMT6-tumor bearing mice were treated with 50 mg/kg LCL161 (p.o.). Tumors were harvested at the indicated time for western blotting using the indicated antibodies.

FIGS. 20a to 20c are graphs showing measurements of mouse weights upon SMC and oncolytic VSV (FIG. 20a), poly(I:C) (FIG. 20b), or CpG (FIG. 20c)

co-treatment in tumor-bearing animals from the experiments depicted in FIGS. 4a, 5b, and 5d, respectively. Error bars, mean±s.e.m.

Figure 21:
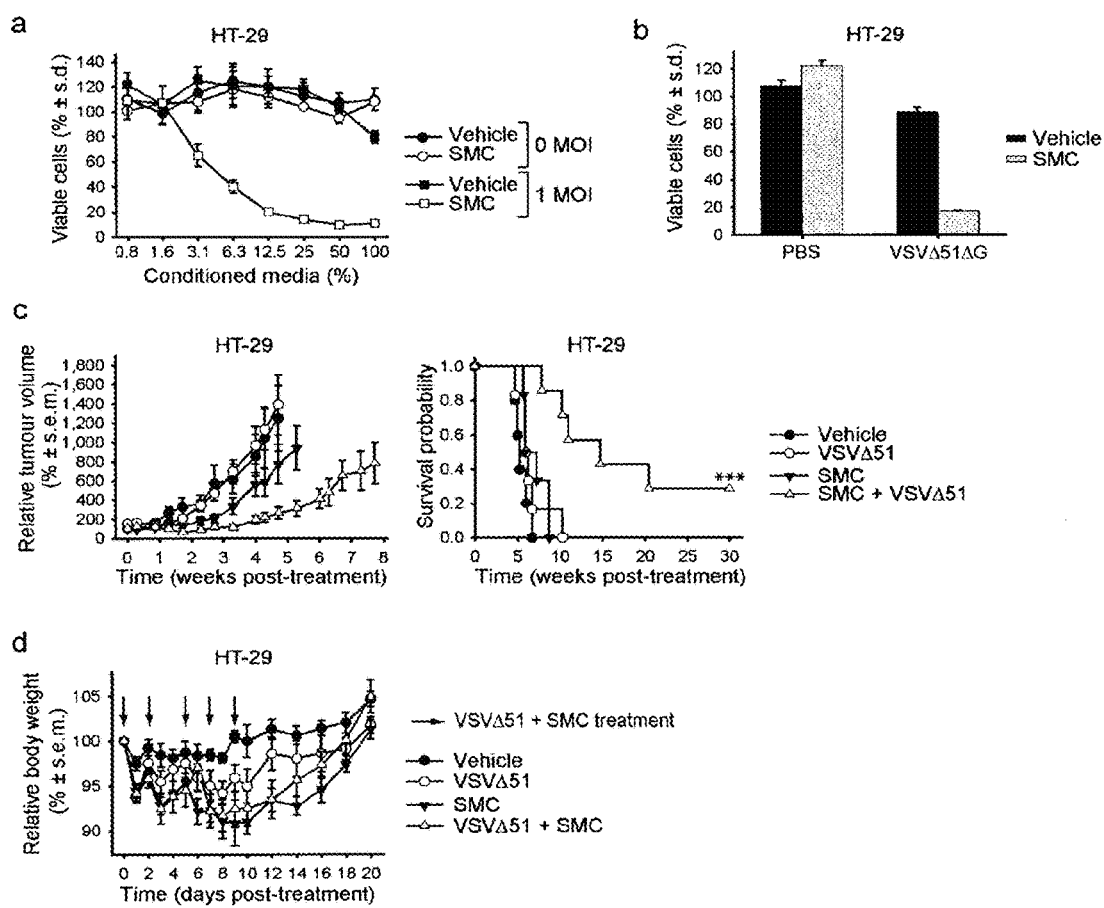

FIGS. 21a-21d are a series of graphs showing that VSVΔ51-induced cell death in HT-29 cell is potentiated by SMC treatment in vitro and in vivo. FIG. 21a is a graph showing data from an experiment in which cells were infected with VSVΔ51, the cell culture supernatant was exposed to UV light for 1 hour and was applied to new cells at the indicated dose in the presence of LCL161. Viability was ascertained by Alamar blue. Error bars, mean±s.d. FIG. 21b is a graph showing Alamar blue viability of cells co-treated with LCL161 and a non-spreading virus VSVΔ51ΔG (0.1 MOI). Error bars, mean±s.d. Panels a and b show representative data from three independent experiments using biological replicates (n=3). FIG. 21c is a pair of graphs showing data from an experiment in which CD-1 nude mice with established HT-29 tumors were treated with 50 mg/kg LCL161 (p.o.) and $1 \times 10^8$ PFU VSVΔ51 (i.t.). Vehicle, n=5; VSVΔ51, n=6; SMC, n=6; VSVΔ51+SMC, n=7. The left panel depicts tumor growth relative to day 0 post-treatment. The right panel represents the Kaplan-Meier curve depicting mouse survival. Error bars, mean±s.e.m. Log-rank with Holm-Sidak multiple comparison: ***, p<0.001. FIG. 21d is a graph showing measurement of mouse weights upon SMC and OV co-treatment in tumor-bearing animals. Error bars, mean±s.e.m.

Figure 22:
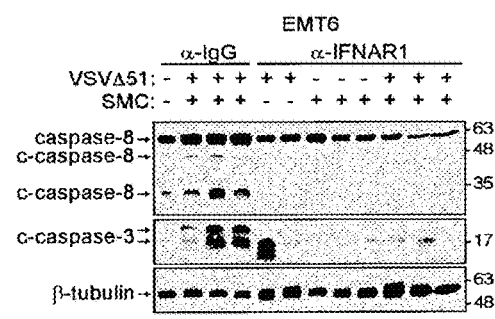

FIG. 22 is a blot showing that type I IFN signaling is required for SMC and OV synergy in vivo. EMT6 tumor bearing mice were treated with vehicle or 50 mg/kg LCL161 for 4 hours, and subsequently treated with neutralizing IFNAR1 or isotype antibodies for 20 hours. Subsequently, animals were treated with PBS or VSVΔ51 for 18 hours. Tumors were processed for Western blotting with the indicated antibodies.

Figure 23:
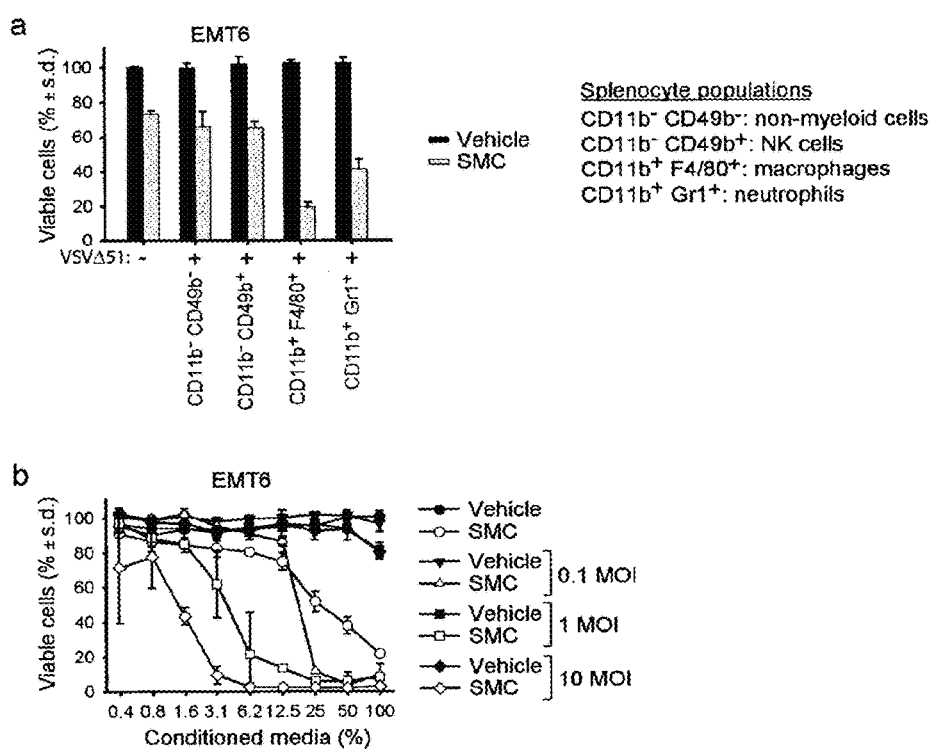

FIGS. 23a and 23b are a pair of graphs showing that oncolytic infection of innate immune cells leads to cancer cell death in the presence of SMCs. FIG. 23a is a graph showing data from an experiment in which immune subpopulations were sorted from splenocytes (CD11b+F4/80+: macrophage; CD11b+Gr1+: neutrophil; CD11 b−CD49b+: NK cell; CD11 b−CD49b−: T and B cells) and were infected with 1 MOI of VSVΔ51 for 24 hours. Cell culture supernatants were applied to SMC-treated ETM6 cells for 24 hours and EMT6 viability was assessed by Alamar Blue. Error bars, mean±s.d. FIG. 23b is a chart showing data from an experiment in which bone marrow derived macrophages were infected with VSVΔ51 and the supernatant was applied to EMT6 cells in the presence of 5 μM SMC, and viability was measured by Alamar blue. Error bars, mean±s.d.

Figure 13:
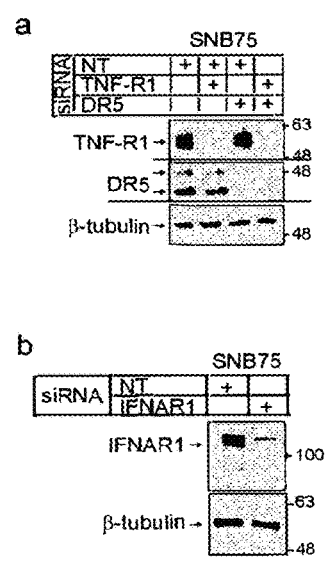
FIGS. 13a and 13b are images showing verification of siRNA-mediated knockdown of non-targeting (NT), TNFR1, DR5 and IFNAR1 by immunoblotting.
Figure 14:
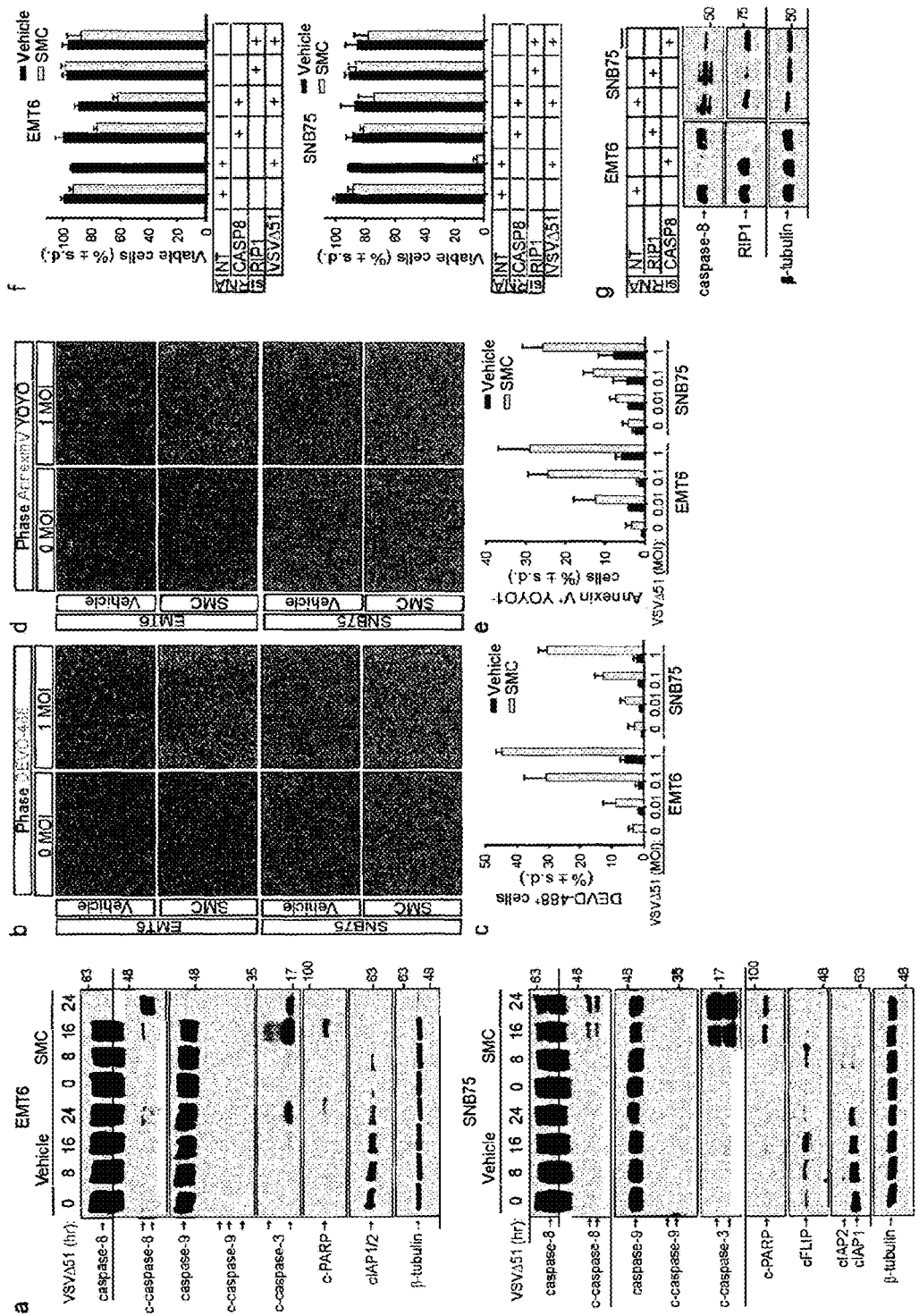
FIGS. 14a-14g are images and graphs showing that SMC synergizes with OVs to induce caspase-8- and RIP-1-dependent apoptosis in cancer cells. All panels of FIG. 14 show representative data from three independent experiments using biological replicates.
Figure 17:
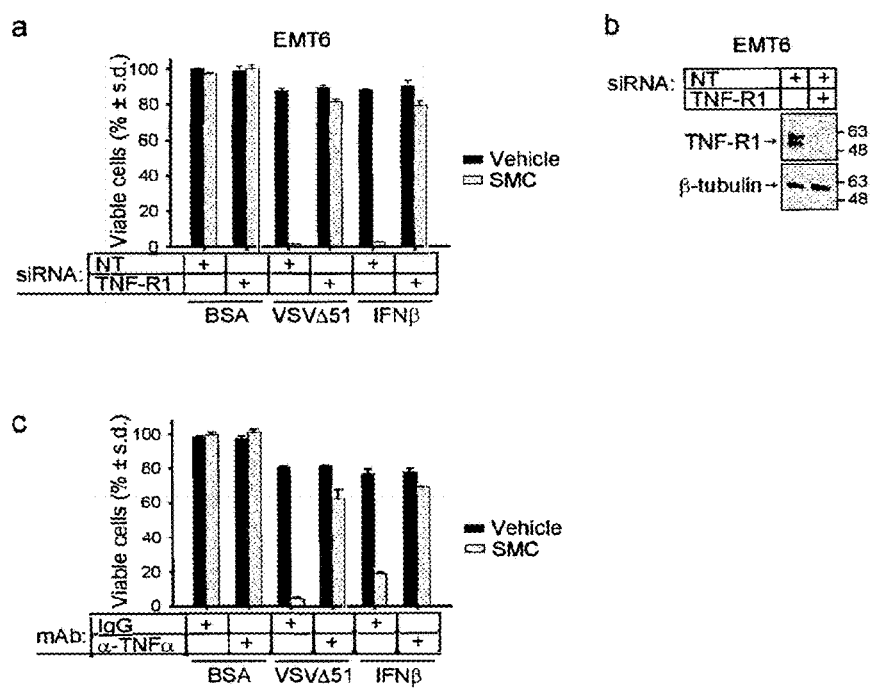
FIGS. 17a-17c are a pair of graphs and an image showing that TNFα signaling is required for type I IFN induced synergy with SMC treatment. All panels of FIG. 17 show representative data from at least three independent experiments using biological replicates (n=3).
Figure 19:
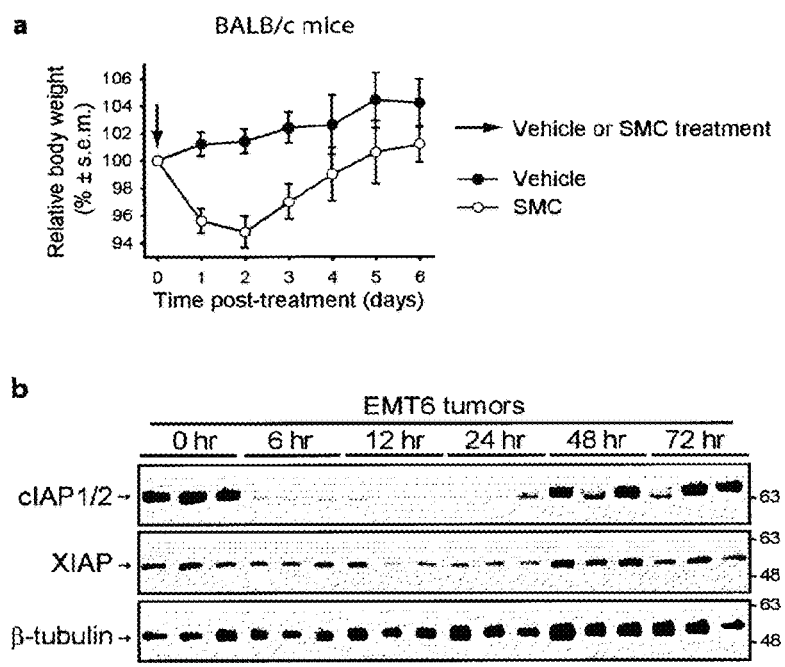
FIGS. 19a and 19b are a graph and a blot showing that SMC treatment causes minimal transient weight loss and leads to downregulation of cIAP1/2.

FIGS. 24a-24h are a series of images of full-length immunoblots. Immunoblots of FIGS. 24a to 24h pertain to (a) FIG. 2e, (b) FIG. 4e, (c) FIG. 10b, (d) FIG. 13, (e) FIG. 14a, (f) FIG. 14g, (g) FIG. 19, and (h) FIG. 17, respectively.

Figure 25:
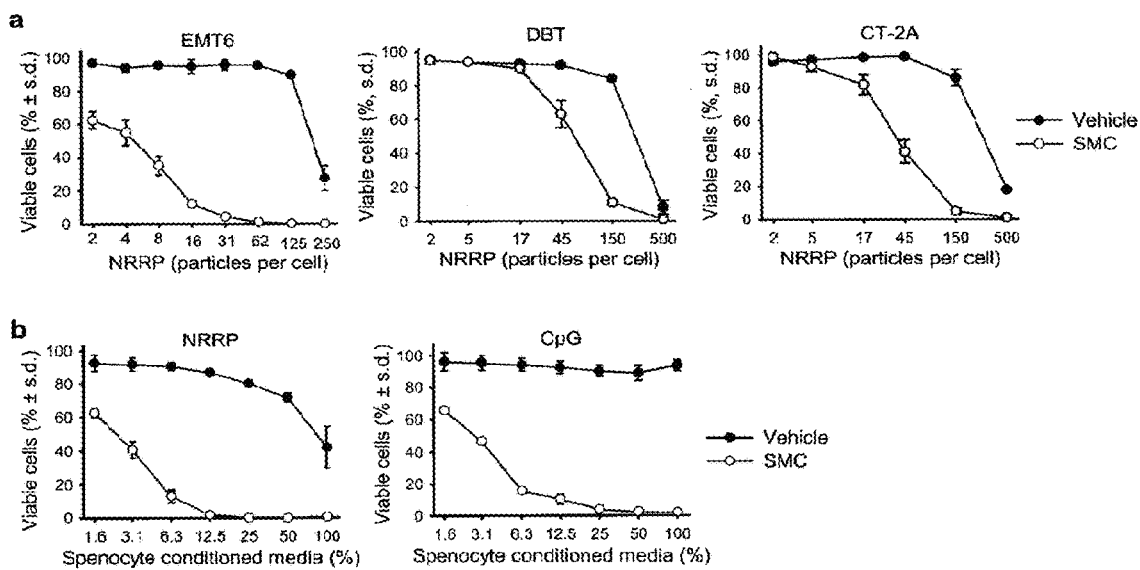

FIGS. 25a and 25b are a set of graphs showing that non-replicating rhabdovirus-derived particles (NRRPs) synergize with SMCs to cause cancer cell death. FIG. 25a is a set of graphs showing data from an experiment in which EMT6, DBT, and CT-2A cancer cells were co-treated with the SMC LCL161 (SMC; EMT6: 5 μM, DBT and CT-2A: 15 μM) and different numbers of NRRPs for 48 hr (EMT6) or 72 hr (DBT, CT-2A), and cell viability was assessed by Alamar Blue. FIG. 25b is a pair of graphs showing data from an experiment in which ufractionated mouse splenocytes were incubated with 1 particle per cell of NRRP or 250 μM CpG ODN 2216 for 24 hr. Subsequently, the supernatant was applied to EMT6 cells in a dose-response fashion, and 5 μM LCL161 was added. EMT6 viability was assessed 48 hr post-treatment by Alamar blue.

Figure 26:
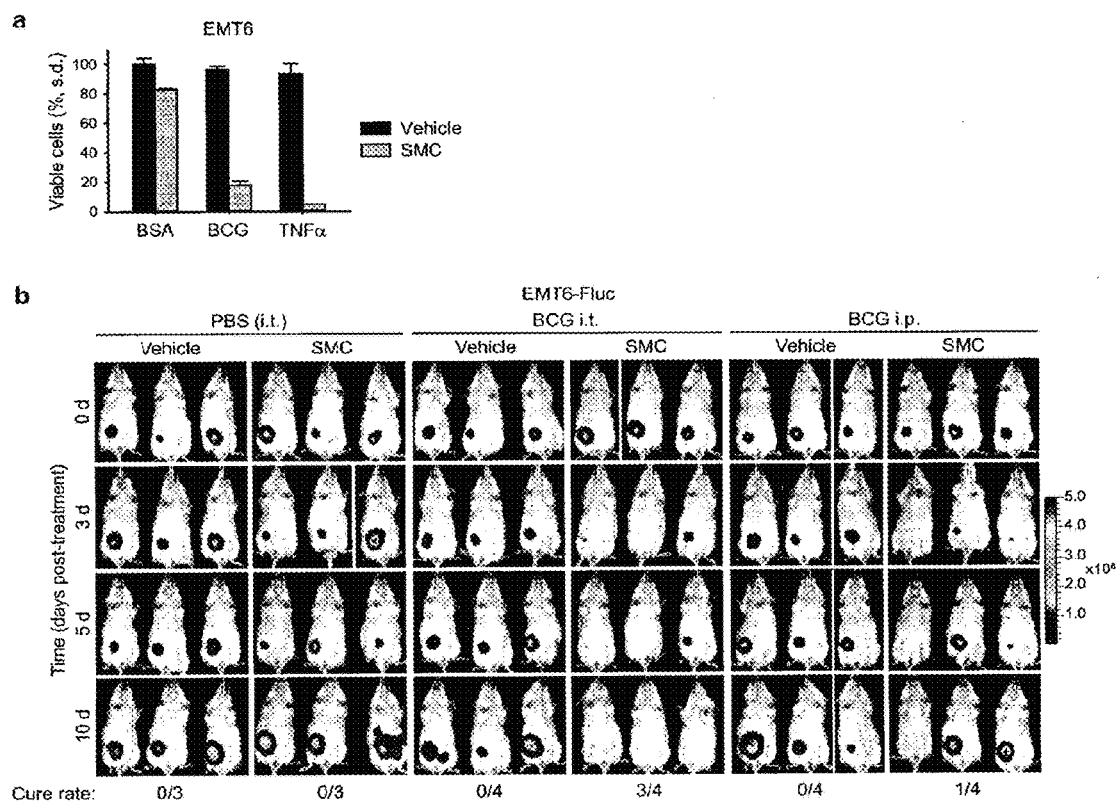

FIGS. 26a and 26b are a graph and a set of image showing that vaccines synergize with SMCs to cause cancer cell death. FIG. 26a is a graph showing data from an experiment in which EMT6 cells were treated with vehicle or 5 μM LCL161 (SMC) and 1000 CFU/mL BCG or 1 ng/mL TNFα for 48 hr, and viability was assessed by Alamar blue. FIG. 26b is a set of representative IVIS images depicting survival of mice bearing mammary fat pad tumors (EMT6-Fluc) that were treated twice with vehicle or 50 mg/kg LCL161 (SMC) and PBS intratumorally (i.t.), BCG ($1 \times 10^5$ CFU) i.t., or BCG ($1 \times 10^5$ CFU) intraperitoneally (i.p.) and subjected to live tumor bioluminescence imaging by IVIS CCD camera at various time points. Scale: p/sec/cm2/sr.

FIGS. 27a and 27b are a pair of graphs and a set of images showing that SMCs synergize with type I IFN to cause mammary tumor regression. FIG. 27a is a pair of graphs showing data from an experiment in which mice were injected with EMT6-Fluc tumors in the mammary fat pad and were treated at eight days post-implantation with combinations of vehicle or 50 mg/kg LCL161 (SMC) orally and bovine serum albumin (BSA), 1 μg IFNα intraperitoneally (i.p.), or 2 μg IFNα intratumorally (i.t.). The left panel depicts tumor growth. The right panel represents the Kaplan-Meier curve depicting mouse survival. Error bars, mean±s.e.m. FIG. 27b is a series of representative IVIS images from the experiment described in 27a. Scale: p/sec/cm2/sr.

Figure 28:
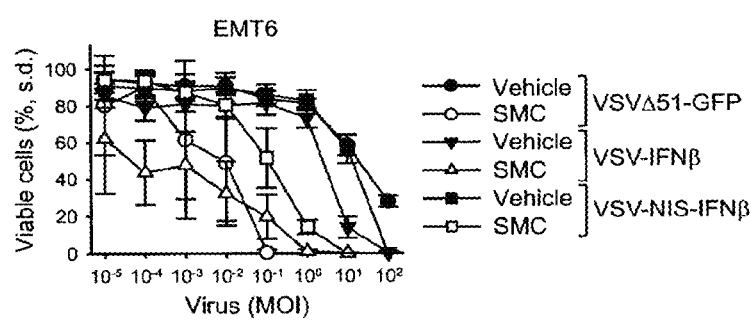

FIG. 28 is a graph showing that the expression of type I IFN from VSV synergizes with SMCs to cause cancer cell death. The graph shows data from an experiment in which EMT6 cells were co-treated with vehicle or 5 μM LCL161 (SMC) and differing multiplicity of infection (MOI) of VSVΔ51-GFP, VSV-IFNβ, or VSV-NIS-IFNβ. Cell viability was assessed 48 hr post-treatment by Alamar blue.

Figure 29:
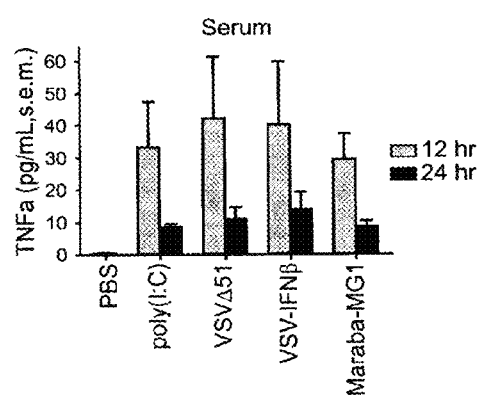

FIG. 29 is a graph showing that non-viral and viral triggers induce robust expression of TNFα in vivo. Mice were treated with 50 mg of poly(I:C) intraperitoneally or with intravenous injections of $5 \times 10^8$ PFU VSVΔ51, VSV-mIFNβ, or Maraba-MG1. At the indicated times, serum was isolated and processed for ELISA to quantify the levels of TNFα.

Figure 30:
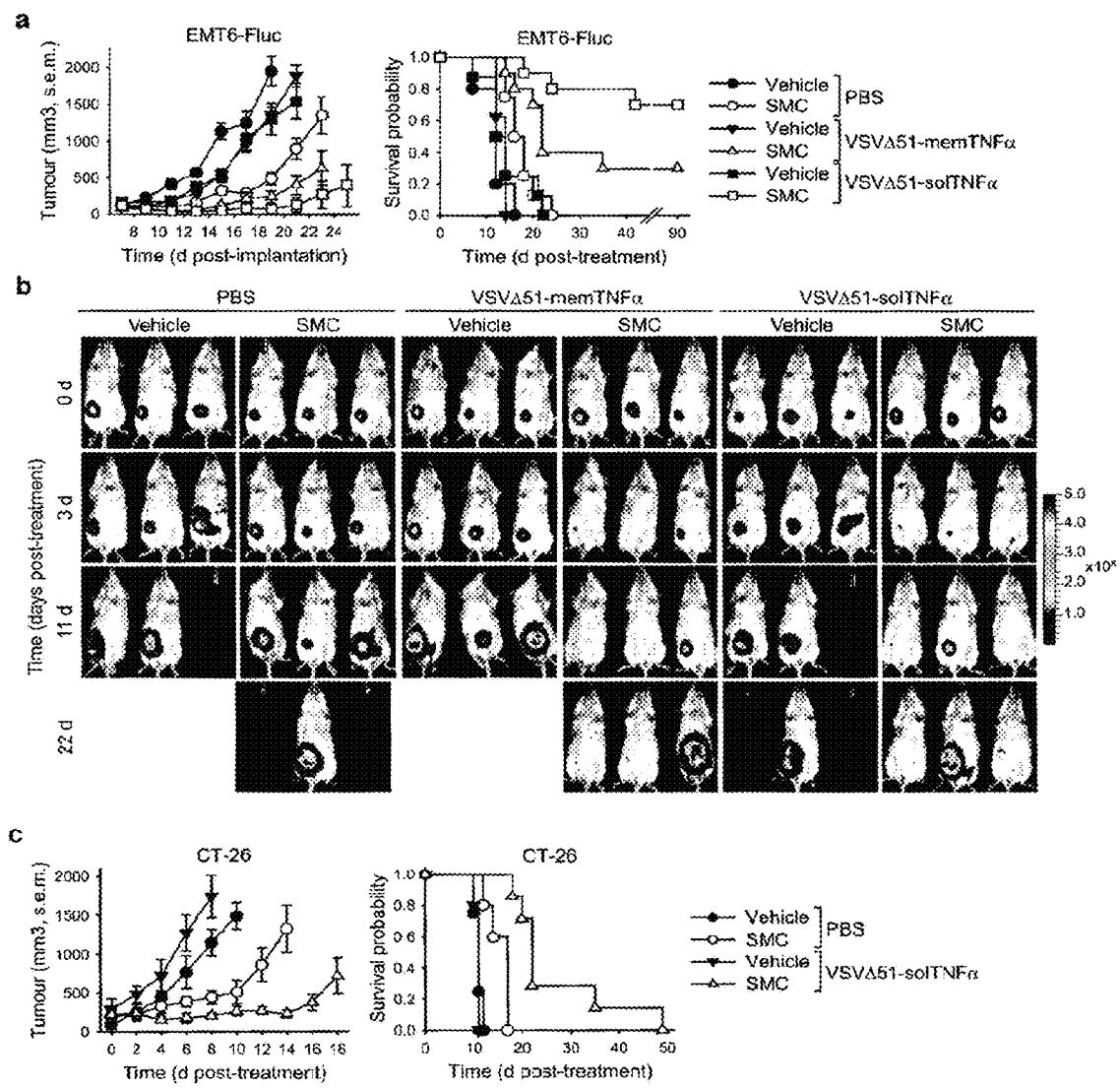

FIGS. 30a-30c are a set of graphs and images showing that virally-expressed proinflammatory cytokines synergizes with SMCs to induce mammary tumor regression. FIG. 30a is a pair of graphs showing data from an experiment in which mice were injected with EMT6-Fluc tumors in the mammary fat pad, and were treated at seven days post-implantation with combinations of vehicle or 50 mg/kg LCL161 (SMC) orally and PBS, $1 \times 10^8$ PFU VSVΔ51-memTNFα (i.v.), or $1 \times 10^8$ PFU VSVΔ51-solTNFα (i.v.). The left panel depicts tumor growth. The right panel represents the Kaplan-Meier curve depicting mouse survival. Error bars, mean±s.e.m. FIG. 30b is a set of representative bioluminescent IVIS images that were acquired from the experiment described in FIG. 30a. Scale: p/sec/cm2/sr. FIG. 30c is a pair of graphs showing data from an experiment in which mice were injected with CT-26 tumors subcutaneously and were treated 10 days post-implantation with combinations of vehicle or 50 mg/kg LCL161 orally and either PBS or $1 \times 10^8$ PFU VSVΔ51-solTNFα intratumorally. The left panel depicts tumor growth. The right panel represents the Kaplan-Meier curve depicting mouse survival. Error bars, mean±s.e.m.

Figure 31:
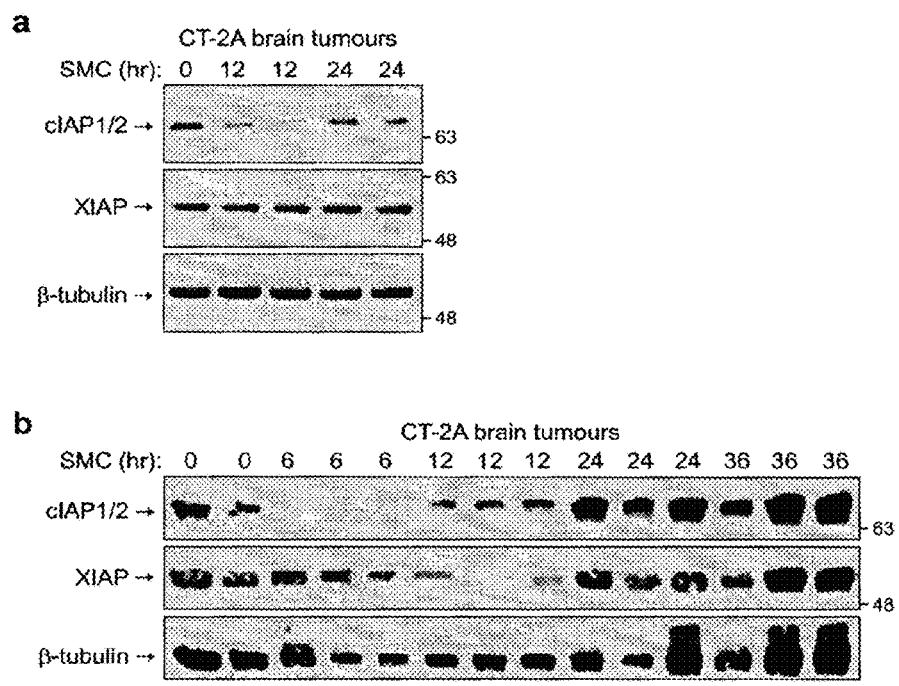

FIGS. 31a and 31b are a set of images showing that SMC treatment leads to down-regulation of cIAP1/2 protein in vivo in an orthotopic, syngeneic mouse model of glioblastoma. FIG. 31a is an image showing an immunoblot from an experiment in which CT-2A cells were implanted intracranially and treated with 50 mg/kg orally of LCL161 (SMC) and tumors were excised at the indicated time points and processed for western blotting using antibodies against cIAP1/2, XIAP, and β-tubulin. FIG. 31b is an image showing an immunoblot from an experiment in which CT-2A cells were implanted intracranially and treated with 10 uL of 100 µM LCL161 intratumorally and tumors were excised at the indicated time points and processed for western blotting using antibodies against cIAP1/2, XIAP, and β-tubulin.

Figure 32:
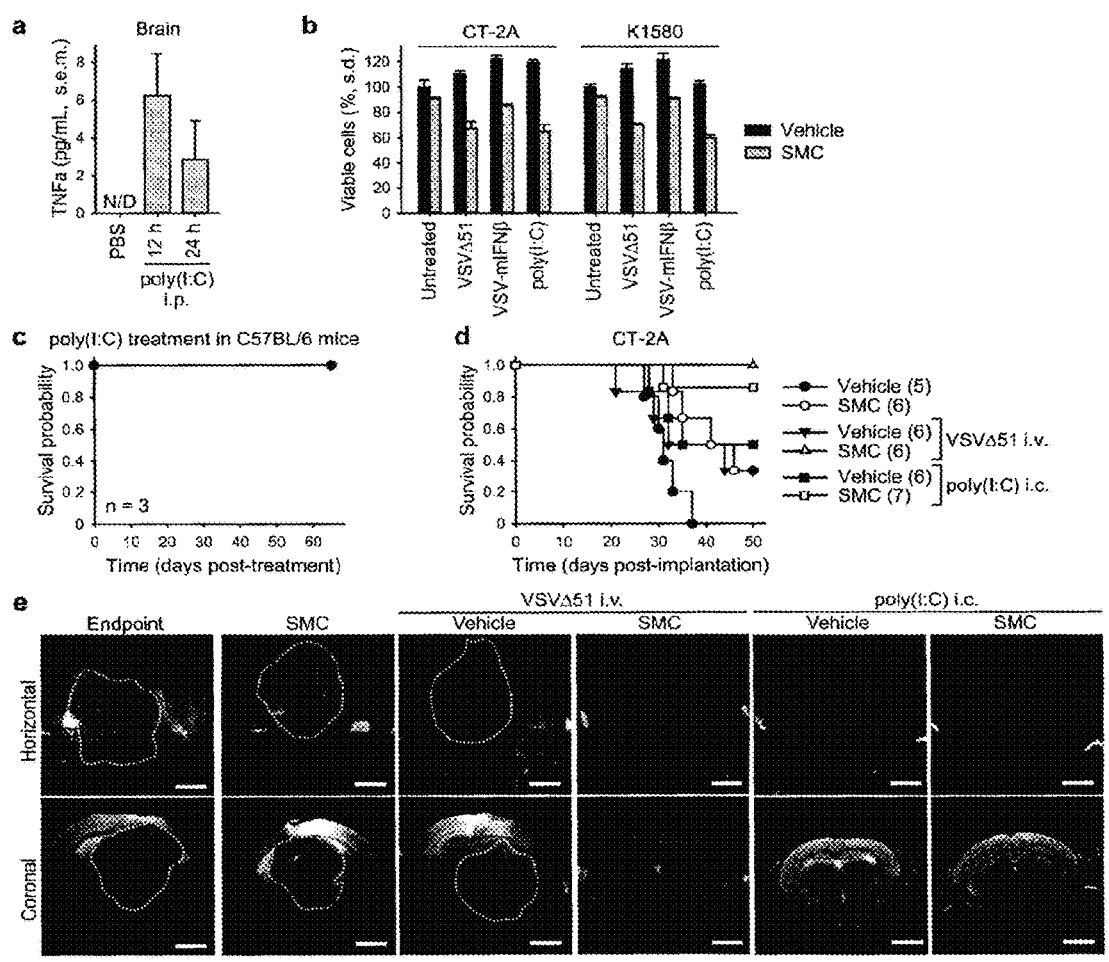

FIGS. 32a-32e are a set of graphs and images showing that a transient proinflammatory response in the brain synergizes with SMCs to cause glioblastoma cell death. FIG. 32a is a graph showing data from an experiment in which an ELISA was conducted to determine the levels of soluble TNFα from 300 mg of crude brain protein extract that was derived from mice injected intraperitoneally (i.p.) with PBS or 50 mg poly(I:C) for 12 or 24 h. Brain protein extracts were obtained by mechanical homogenization in saline solution. FIG. 32b is a graph showing data from Alamar blue viability assays of mouse glioblastoma cells (CT-2A, K1580) that were treated with 70 mg of crude brain homogenates and 5 µM LCL161 (SMC) in culture for 48 h. Brain homogenates were obtained from mice that were treated for 12 h with i.p. injections of poly(I:C), or intravenous injections of $5 \times 10^8$ PFU VSVΔ51 or VSV-mIFNβ. FIG. 32c represents the Kaplan-Meier curve depicting survival of mice that received three intracranial treatments of 50 mg poly(I:C). Treatments were on days 0, 3, and 7. FIG. 32d represents the Kaplan-Meier curve depicting survival of mice bearing CT-2A intracranial tumors that received combinations of SMC, VSVΔ51 or poly(I:C). Mice received combinations of three treatments of vehicle, three treatments of 75 mg/kg LCL161 (oral), three treatments of $5 \times 10^8$ PFU VSVΔ51 (i.v.), or two treatments of 50 mg poly(I:C) (intracranial, i.c.). Mice were treated on day 7, 10, and 14 post tumor cell implantation with the different conditions, except for the poly(I:C) treated group that received i.c. injections on day 7 and 15. Numbers in brackets denote number of mice per group. FIG. 34e is a series of representative MRI images of mouse skulls from the experiments depicted in FIG. 34d, which shows an animal at endpoint and a representative mouse of the indicated groups at 50 days post-implantation. Dashed line denotes the brain tumor.

Figure 33:
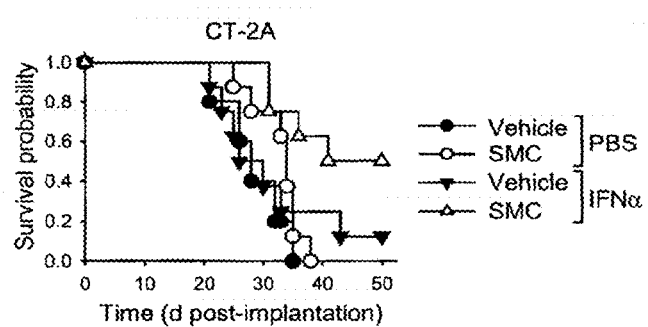

FIG. 33 is a graph showing that SMCs synergize with type I IFN to eradicate brain tumors. The graph represents the Kaplan-Meier curve depicting survival of mice bearing CT-2A that received intracranial injections of vehicle or 100 µM LCL161 (SMC) with PBS or 1 µg IFNα at 7 days post-implantation.

DETAILED DESCRIPTION

The present invention includes methods and compositions for enhancing the efficacy of Smac mimetic compounds (SMCs) in the treatment of cancer. In particular, the present invention includes methods and compositions for combination therapies that include an SMC and a second agent that stimulates one or more cell death pathways that are inhibited by cIAP1 and/or cIAP2. The second agent may be, e.g., a TLR agonist a virus, such as an oncolytic virus, or an interferon or related agent.

The data provided herein demonstrates that treatment with an immunostimulatory agent and an SMC results in tumor regression and durable cures in vivo (see, e.g., Example 1). These combination therapies were well tolerated by mice, with body weight returning to pre-treatment levels shortly after the cessation of therapy. Tested combination therapies were able to treat several treatment refractory, aggressive mouse models of cancer. One of skill in the art will recognize, based on the disclosure and data provided herein, that any one or more of a variety of SMCs and any one or more of a variety of immunostimulatory agents, such as a TLR agonist, pathogen, or pathogen mimetic, may be combined in one or more embodiments of the present invention to potentiate apoptosis and treat cancer.

While other approaches to improve SMC therapy have been attempted, very rarely have complete responses been observed, particularly in aggressive immunocompetent model systems. Some embodiments of the present invention, including treatment of cancer with a pathogen mimetic, e.g., a pathogen mimetic having a mechanism of action partially dependent on TRAIL, can have certain advantages. First, this approach can evoke TNFα-mediated apoptosis and necroptosis: given the plasticity and heterogeneity of some advanced cancers, treatments that simultaneously induce multiple distinct cell death mechanisms may have greater efficacy than those that do not. Second, pathogen mimetics can elicit an integrated innate immune response that includes layers of negative feedback. These feedback mechanisms may act to temper the cytokine response in a manner difficult to replicate using recombinant proteins, and thus act as a safeguard to this combination therapy strategy.

SMCs

An SMC of the present invention may be any small molecule, compound, polypeptide, protein, or any complex thereof, capable, or predicted of being capable, of inhibiting cIAP1 and/or cIAP2, and, optionally, one or more additional endogenous Smac activities. An SMC of the present invention is capable of potentiating apoptosis by mimicking one or more activities of endogenous Smac, including but not limited to, the inhibition of cIAP1 and the inhibition of cIAP2. An endogenous Smac activity may be, e.g., interaction with a particular protein, inhibition of a particular protein's function, or inhibition of a particular IAP. In particular embodiments, the SMC inhibits both cIAP1 and cIAP2. In some embodiments, the SMC inhibits one or more other IAPs in addition to cIAP1 and cIAP2, such as XIAP or Livin/ML-IAP, the single BIR-containing IAP. In particular embodiments, the SMC inhibits cIAP1, cIAP2, and XIAP. In any embodiment including an SMC and an immune stimulant, an SMC having particular activities may be selected for combination with one or more particular immune stimulants. In any embodiment of the present invention, the SMC may be capable of activities of which Smac is not capable. In some instances, these additional activities may contribute to the efficacy of the methods or compositions of the present invention.

Treatment with SMCs can deplete cells of cIAP1 and cIAP2, through, e.g., the induction of auto- or trans-ubiquitination and proteasomal-mediated degradation. SMCs can also de-repress XIAP's inhibition of caspases. SMCs may primarily function by targeting cIAP1 and 2, and by converting TNFα, and other cytokines or death ligands, from a survival signal to a death signal, e.g., for cancer cells.

Certain SMCs inhibit at least XIAP and the cIAPs. Such "pan-IAP" SMCs can intervene at multiple distinct yet interrelated stages of programmed cell death inhibition. This characteristic minimizes opportunities for cancers to develop resistance to treatment with a pan-IAP SMC, as multiple death pathways are affected by such an SMC, and allows synergy with existing and emerging cancer therapeutics that activate various apoptotic pathways in which SMCs can intervene.

One or more inflammatory cytokines or death ligands, such as TNFα, TRAIL, and IL-1β, potently synergize with SMC therapy in many tumor-derived cell lines. Strategies to increase death ligand concentrations in SMC-treated tumors, in particular using approaches that would limit the toxicities commonly associated with recombinant cytokine therapy, are thus very attractive. TNFα, TRAIL, and dozens of other cytokines and chemokines can be upregulated in response to pathogen recognition by the innate immune system of a subject. Importantly, this ancient response to microbial pathogens is usually self-limiting and safe for the subject, due to stringent negative regulation that limits the strength and duration of its activity.

SMCs may be rationally designed based on Smac. The ability of a compound to potentiate apoptosis by mimicking one or more functions or activities of endogenous Smac can be predicted based on similarity to endogenous Smac or known SMCs. An SMC may be a compound, polypeptide, protein, or a complex of two or more compounds, polypeptides, or proteins.

In some instances, SMCs are small molecule IAP antagonists based on an N-terminal tetrapeptide sequence (revealed after processing) of the polypeptide Smac. In some instances, an SMC is a monomer (monovalent) or dimer (bivalent). In particular instances, an SMC includes 1 or 2 moieties that mimic the tetrapeptide sequence of AVPI from Smac/DIABLO, the second mitochondrial activator of caspases, or other similar IBMs (e.g., IAP-binding motifs from other proteins like casp9). A dimeric SMC of the present invention may be a homodimer or a heterodimer. In certain embodiments, the dimer subunits are tethered by various linkers. The linkers may be in the same defined spot of either subunit, but could also be located at different anchor points (which may be 'aa' position, P1, P2, P3 or P4, with sometimes a P5 group available). In various arrangements, the dimer subunits may be in different orientations, e.g., head to tail, head to head, or tail to tail. The heterodimers can include two different monomers with differing affinities for different BIR domains or different IAPs. Alternatively, a heterodimer can include a Smac monomer and a ligand for another receptor or target which is not an IAP. In some instances, an SMCs can be cyclic. In some instances, an SMC can be trimeric or multimeric. A multimerized SMC can exhibit a fold increase in activity of 7,000-fold or more, such as 10-, 20-, 30-, 40-, 50-, 100-, 200-, 1,000-, 5,000-, 7,000-fold, or more (measured, e.g., by EC50 in vitro) over one or more corresponding monomers. This may occur, in some instances, e.g., because the tethering enhances the ubiquitination between IAPs or because the dual BIR binding enhances the stability of the interaction. Although multimers, such as dimers, may exhibit increased activity, monomers may be preferable in some embodiments. For example, in some instances, a low molecular weight SMC may be preferable, e.g., for reasons related to bioavailability.

In some instances of the present invention, an agent capable of inhibiting cIAP1/2 is a bestatin or Me-bestatin analog. Bestatin or Me-bestatin analogs may induce cIAP1/2 autoubiquitination, mimicking the biological activity of Smac.

In certain embodiments of the present invention, an SMC combination treatment includes one or more SMCs and one or more interferon agents, such as an interferon type 1 agent, an interferon type 2 agent, and an interferon type 3 agent. Combination treatments including an interferon agent may be useful in the treatment of cancer, such as multiple myeloma.

In some embodiments, a VSV expressing IFN, and optionally expressing a gene that enables imaging, such as NIS, the sodium-iodide symporter, is used in combination with an SMC. For instance, such a VSV may be used in combination with an SMC, such as the Ascentage Smac mimetic SM-1387/APG-1387, the Novartis Smac mimetic LCL161, or Birinapant. Such combinations may be useful in the treatment of cancer, such as hepatocellular carcinoma or liver metastases.

Various SMCs are known in the art. Non-limiting examples of SMCs are provided in Table 1. While Table 1 includes suggested mechanisms by which various SMCs may function, methods and compositions of the present invention are not limited by or to these mechanisms.

TABLE 1

Smac mimetic compounds

| Compound | Structure or Reference | Clinical Status | Organization; author/inventor |
| --- | --- | --- | --- |
| GDC-0152/ RG7419 | Baker J E, Boerboom L E, Olinger G N. Cardioplegia-induced damage to ischemic immature myocardium is independent of oxygen availability. Ann Thorac Surg. 1990 Dec;50(6):934-9. | Clinical trials | Genentech/Roche; W. Fairbrother |
| GDC-0145 | | Clinical trials | Genentech/Roche; W. Fairbrother |
| AEG40826/ HGS1029 | | Clinical trials | Aegera/Pharmascience (Canada); J. Jaquith |
| LCL-161 | Chen K F, Lin J P, Shiau C W, Tai W T, Liu C Y, Yu H C, Chen P J, Cheng A L. Inhibition of Bcl-2 improves effect of LCL161, a SMAC mimetic, in hepatocellular carcinoma cells. Biochem Pharmacol. 2012 Aug. 1;84(3): 268-77. doi: 10.1016/j.bcp.2012.04.023. Epub 2012 May 9. | Clinical trials | Novartis; L. Zawel |
| AT-406/ SM406/ Debio1143/ D1143 | Cai Q, Sun H, Peng Y, Lu J, Nikolovska-Coleska Z, McEachern D, Liu L, Qiu S, Yang C Y, Miller R, Yi H, Zhang T, Sun D, Kang S, Guo M, Leopold L, Yang D, Wang S. A potent and orally active antagonist (SM-406/AT-406) of multiple inhibitor of apoptosis proteins (IAPs) in clinical development for cancer treatment. J Med Chem. 2011 Apr. 28;54(8):2714-26. doi: 10.1021/jm101505d. Epub 2011 Mar. 28. | Clinical trials | Ascenta (USA)/DebioPharma (Switzerland); Shaomeng Wang (University of Michigan) |
| TL32711/ Birinapant (formerly TL32711) | Dubrez L, Berthelet J, Glorian V. IAP proteins as targets for drug development in oncology. Onco Targets Ther. 2013 Sep. 16;9:1285-1304. eCollection 2013. Review. | Clinical trials | Tetralogic (USA, formerly Gentara with GTI cpd designations); S. Condon |
| GDC-0917/ CUDC-427 | Wong H, Gould S E, Budha N, Darbonne W C, Kadel E E 3rd, La H, Alicke B, Halladay J S, Erickson R, Portera C, Tolcher A W, Infante J R, Mamounas M, Flygare J A, Hop C E, | Clinical trials | Curis (Genentech); W. Fairbrother |

TABLE 1-continued

Smac mimetic compounds

| Compound | Structure or Reference | Clinical Status | Organization; author/inventor |
|---|---|---|---|
| | Fairbrother W J. Learning and confirming with preclinical studies: modeling and simulation in the discovery of GDC-0917, an inhibitor of apoptosis proteins antagonist. Drug Metab Dispos. 2013 Dec.;41(12):2014-13. doi:10.1124/dmd.113.053926. Epub 2013 Sep. 16. | | |
| APG-1387/ SM-1387 | | Clinical trials | Ascenta (USA)/Ascentage (China); Shaomeng Wang |
| AZD5582 | Hennessy E J, Adam A, Aquila B M, Castriotta L M, Cook D, Hattersley M, Hird A W, Huntington C, Kamhi V M, Laing N M, Li D, Macintyre T, Omer C A, Oza V, Patterson T, Repik G, Rooney M T, Saeh J C, Sha L, Vasbinder M M, Wang H, Whitston D. Discovery of a Novel Class of Dimeric Smac Mimetics as Potent IAP Antagonists Resulting in a Clinical Candidate for the Treatment of Cancer (AZD5582). J Med Chem. 2013 Dec. 27;56(24):9897-919. doi: 10.1021/jm401075x. Epub 2013 Dec. 13. | Clinical candidate | AstraZeneca; E. Hennessy |
| T-3256336 | Sumi H, Yabuki M, Iwai K, Morimoto M, Hibino R, Inazuka M, Hashimoto K, Kosugi Y, Aoyama K, Yamamoto S, Yoshimatsu M, Yamasaki H, Tozawa R, Ishikawa T, Yoshida S. Antitumor activity and pharmacodynamic biomarkers of a novel and orally available small-molecule antagonist of inhibitor of apoptosis proteins. Mol Cancer Ther. 2013 Feb;12(2):230-40. doi: 10.1158/1535-7163.MCT-12-0699. Epub 2012 Dec. 12. | Clinical candidate | Takeda (Japan); D. Dougan, T. Ishikawa |
| JP1584 | | Clinical candidate | Joyant (GeminX, USA); Xiaodong Wang, Patrick Harran |
| JP1201 | | Clinical candidate | Joyant (GeminX, USA); Xiaodong Wang, Patick Harran |
| GT-A | | Clinical candidate | Joyant (GerminX, USA); Xiaodong Wang, Patrick Harran |
| AT-IAP | Gianni Chessari, Ahn Maria, Ildiko Buck, Elisabetta Chiarparin, Joe Coyle, James Day, Martyn Frederickson, Charlotte Griffiths-Jones, Keisha Hearn, Steven Howard, Tom Heightman, Petra Hillmann, Aman Iqbal, Christopher N. Johnson, Jon Lewis, Vanessa Martins, Joanne Munck, Mike Reader, Lee Page, Anna Hopkins, Alessia Millemaggi, Caroline Richardson, Gordon Saxty, Tomoko Smyth, Emiliano Tamanini, Neil Thompson, George Ward, Glyn Williams, Pamela Williams, Nicola Wilsher, and Alison Woolford. Abstract 2944: AT-IAP, a dual cIAP1 and XIAP antagonist with oral antitumor activity in melanoma models. *Cancer Research*: Apr. 15, 2013; Volume 73, Issue 8, Supplement 1 doi: 10.1158/1538-7445.AM2013-2944 Proceedings: AACR 104th Annual Meeting 2013; Apr. 6-10, 2013; Washington, DC | Clinical candidate | Astex (UK)/Otsuka (Japan); G. Chessari |
| inhib1 | Park C M, Sun C, Olejniczak E T, Wilson A E, Meadows R P, Betz S F, Elmore S W, Fesik S W. Non-peptidic small molecule inhibitors of XIAP. Bioorg Med Chem Lett. 2005 Feb. 1;15(3):771-5. | | Pfizer (IDUN acquired cpds from Abbott collaboration); S W Fesik, K J Tomaselli |
| inhib2 | Park C M, Sun C, Olejniczak E T, Wilson A E, Meadows R P, Betz S F, Elmore S W, Fesik S W. Non-peptidic small molecule inhibitors of XIAP. Bioorg Med Chem Lett. 2005 Feb. 1;15(3):771-5. | | Pfizer (IDUN acquired cpds from Abbott collaboration); S W Fesik, K J Tomaselli |
| AT-406/ SM406/ Debio 1143/ D1143 | Cai Q, Sun H, Peng Y, Lu J, Nikolovska-Coleska Z, McEachern D, Liu L, Qiu S, Yang C Y, Miller R, Yi H, Zhang T, Sun D, Kang S, Guo M, Leopoid L, Yang D, Wang S. A potent and orally active antagonist (SM-406/AT-406) of multiple inhibitor of apoptosis proteins (IAPs) in clinical development for cancer treatment. J Med Chem. 2011 Apr. 28; 54(8):2714-26. doi: 10. 1021/jm101505d. Epub 2011 Mar. 28. | Clinical trials | Ascenta (USA)/DebioPharma (Switzerland); Shaomeng Wang (University of Michigan) |
| AT-406/ SM406/ Debio1143/ D1143 | Cai Q, Sun H, Peng Y, Lu J, Nikolovska-Coleska Z, McEachern D, Liu L, Qiu S, Yang C Y, Miller R, Yi H, Zhang T, Sun D, Kang S, Guo M, Leopold L, Yang D, Wang S. A potent and orally active antagonist (SM-406/AT-406) of multiple inhibitor of apoptosis proteins (IAPs) in clinical development for cancer treatment. J Med Chem. 2011 Apr. 28;54(8):2714-26. doi: 10.1021/jm101505d. Epub 2011 Mar. 28. | Clinical trials | Ascenta (USA)/DebioPharma (Switzerland); Shaomeng Wang (University of Michigan) |

TABLE 1-continued

Smac mimetic compounds

| Compound | Structure or Reference | Clinical Status | Organization; author/inventor |
|---|---|---|---|
| BI-75D2 | Formula: $C_{26}H_{26}N_4O_4S_2$ 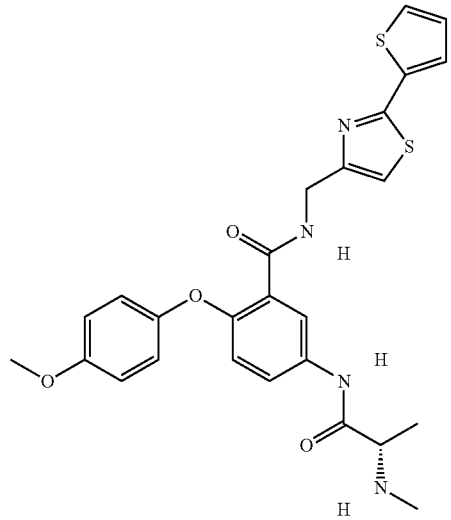 | Preclinical | Sanford-Burnham Institute; J. Reed |
| T5TR1 | Crisóstomo F R, Feng Y, Zhu X, Welsh K, An J, Reed J C, Huang Z. Design and synthesis of a simplified inhibitor for XIAP-BIR3 domain. Bioorg Med Chem Lett. 2009 Nov. 15;19(22):6413-8. doi: 0.1016/j.bmcl.2009.09.058. Epub 2009 Sep. 17. PubMed PMID: 19819692; PubMed Central PMCID: PMC3807767. | Preclinical | Sanford-Burnham Institute (NIH?); J. Reed |
| ML-101 | Welsh K, Yuan H, Stonich D, Su Y, Garcia X, Cuddy M, Houghten R, Sergienko E, Reed J C, Ardecky R, Ganji S R, Lopez M, Dad S, Chung T D Y, Cosford N. Antagonists of IAP-family anti-apoptotic proteins- Probe 1. 2009 May 18 [updated 2010 Sep. 2]. Probe Reports from the NIH Molecular Libraries Program [Internet]. Bethesda (MD): National Center for Biotechnology Information (US); 2010-. Available from http://www.ncbi.nim.nih.gov/books/NBK47341/; González-López M, Welsh K, Finlay D, Ardecky R J, Ganji S R, Su Y, Yuan H, Teriete P, Mace P D, Riedl S J, Vuori K, Reed J C, Cosford N D. Design, synthesis and evalutation of monovalent Smac mimetics that bind to the BIR2 domain of the anti-apoptotic protein XIAP. Bioorg Med Chem Lett. 2011 Jul. 15;21(14):4332-6. doi: 10.1016:j.bmcl.2011.05.049. Epub 2011 May 24. | Preclinical | Sanford-Burnham Institute (NIH?); J. Reed |
| MLS-0390866 | Welsh K, Yuan H, Stonich D, Su Y, Garcia X, Cuddy M, Houghten R, Sergienko E, Reed J C, Ardecky R, Ganji S R, Lopez M, Dad S, Chung T D Y, Cosford N. Antagonists of IAP-family anti-apoptotic proteins-Probe 1. 2009 May 18 [updated 2010 Sep. 2]. Probe Reports from the NIH Molecular Libraries Program [Internet]. Bethesda (MD): National Center for Biotechnology Information (US); 2010-. Available from http://www.ncbi.nlm.nih.gov/books/NBK47341/PubMed | Preclinical | Sanford-Burnham Institute (NIH?); J. Reed |
| MLS- | Finlay D, Vamos M, González-López M, Ardecky R J, Ganji S R, Yuan H, Su Y, Cooley T R, Hauser C T, Welsh K, Reed J C, Cosford N D, Vuori K. Small-Molecule IAP Antagonists Sensitize Cancer Cells to TRAIL-Induced Apoptosis: Roles of XIAP and cIAPS. Mol Cancer Ther. 2014 January;13(1):5-15. doi: 10.1158/1535-7163.MCT-13-0153. Epub 2013 Nov. 5. | Preclinical | Sanford-Burnham institute (NIH?); J. Reed |
| ML183 | Ardecky R J, Welsh K, Finlay D, Lee P S, González-López M, Ganji S R, Ravanan P, Mace P D, Riedl S J, Vuori K, Reed J C, Cosford N D. Design, synthesis and evaluation of inhibitor of apoptosis protein (IAP) antagonists that are highly selective for the BIR2 domain of XIAP. Bioorg Med Chem Lett. 2013 Jul. 15;23(14):4253-7. doi: 10.1016/j.bmcl.2013.04.096. Epub 2013 May 14;-Lopez M, Welsh K, Yuan H, Stonich D, Su Y, Garcia X, Cuddy M, Houghten R, Sergienko E, Reed J C, Ardecky R, Reddy S, Finlay D, Vuori K, Dad S, Chung T D Y, Cosford N D P. Antagonists of IAP-family anti-apoptotic proteins-Probe 2. 2009 Sep. 1 [undated 2011 Feb. 10 ]. Probe Reports from the NIH Molecular Libraries Program [Internet]. Bethesda (MD): National Center for Biotechnology Information (US); 2010-. Available from http://www.ncbi.nim.nih.gov/books/NBK55068/ | Preclinical | Sanford-Burnham Institute (NIH?); J. Reed |
| SM-83 | Gatti L, De Cesare M, Ciusani E, Corna E, Arrighetti N, Cominetti D, Belvisi L, Potenza D, Moroni E, Vasile F, Lecis D, Delia D, Castiglioni V, Scanziani E, Seneci P, Zaffaroni N, Perego P. Antitumor Activity of a Novel Homodimeric SMAC Mimetic in Ovarian Carcinoma. Mol Pharm. 2014 Jan. 6;11(1):283-93. doi: 10.1021/mp4004578. Epub 2013 Nov. 27. | Preclinical | University of Milan; M. Bolognesi |
| SMAC037/ SM37 | Mastrangelo E, Cossu F, Milani M, Sorrentino G, Lecis D, Delia D, Manzoni L, Drago C, Seneci P, Scolastico C, Rizzo V, Bolognesi M. Targeting the X-linked inhibitor of apoptosis protein through 4-substituted azabicyclo[5.3.0]alkene smac mimetics. Structure, activity, and recognition principles. J Mol Biol. 2008 Dec. 19;384(3):673-89. dio: 10.1016/j.jmb.2008.09.064. pub 2008 Oct. 7. | Preclinical | University of Milan; M. Bolognesi |

TABLE 1-continued

Smac mimetic compounds

| Compound | Structure or Reference | Clinical Status | Organization; author/inventor |
|---|---|---|---|
| SMAC066 | Cossu F, Malvezzi F, Canevari G, Mastrangelo E, Lecis D, Delia D, Seneci P, Scolastico C, Bolognesi M, Milani M. Recognition of Smac-mimetic compounds by the BIR domain of cIAP1. Protein Sci. 2010 ec;19(12):2418-29. doi: 10.1002/pro.523. | Preclinical | University of Milan; M. Bolognesi |
| SMC9a | Monomer: Seneci P, Bianchi A, Battaglia C, Belvisi M, Bolognesi M, Caprini A, Cossu F, Franco Ed, Matteo Md, Delia D, Drago C, Khaled A, Lecis D, Manzoni L, Marizzoni M, Mastrangelo E, Milani M, Motto I, Moroni E, Potenza D, Rizzo V, Servida F, Turlizzi E, Varrone M, Vasile F, Scolastico C. Rational design, synthesis and characterization of potent, non-peptidic Smac mimics/XIAP inhibitors as proapoptotic agents for cancer therapy. Bioorg Med Chem. 2009 Aug. 15;17(16):5834-56. doi: 10.1016/j.bmc.2009.07.009. Epub 2009 Jul. 10. Dimer in different configurations: Ferrari V, Cutler D J, Uptake of chloroquine by human erythrocytes. Biochem Pharmacol. 1990 Feb. 15;39(4):753-62. PubMed PMID: 2306282.; Cossu F, Milani M, Vachette P, Malvezzi F, Grassi S, Lecis D, Delia D, Drago C, Seneci P, Bolognesi M, Mastrangelo E. Structural insight into inhibitor of apoptosis proteins recognition by a potent divalent smac-mimetic. PLoS One. 2012;7(11):e49527. doi: 10.1371/journal.pone.0049527. Epub 2012 Nov. 15. | Preclinical | University of Milan; M. Bolognesi |
| OICR-720 | Enwere E K, Holbrook J, Lejmi-Mrad R, Vineham J, Timusk K, Sivaraj B, Isaac M, Uehling D, Al-awar R, LaCasse E, Komeluk R G. TWEAK and cIAP1 regulate myoblast fusion through the noncanonical NF-κB signaling pathway. Sci Signal. 2012 Oct. 16;5(246):ra75. doi: 10.1126/scisignal.2003086. | Preclinical | Ontario Institute for Cancer Research; R. Komeluk |
| SM-164 | Sun H, Nikolovska-Coleska Z, Lu J, Meagher J L, Yang C Y, Qiu S, Tomita Y, Ueda Y, Jiang S, Krajewski K, Roller P P, Stuckey J A, Wang S. Design, synthesis, and characterization of a potent, nonpeptide, cell-permeable, bivalent Smac mimetic that concurrently targets both the BIR2 and BIR3 domains in XIAP. J Am Chem Soc. 2007 Dec. 12;129(49):15279-94. Epub 2007 Nov. 14. | Preclinical | Ascenta |
| SM1200 | Sheng R, Sun H, Liu L, Lu J, McEachern D, Wang G, Wen J, Min P, Du Z, Lu H, Kang S, Guo M, Yang D, Wang S. A potent bivalent Smac mimetic (SM-1200) achieving rapid, complete, and durable tumor regression in mice. J Med Chem. 2013 May 23;56(10):3969-79. doi: 10.1021/jm400216d. Epub 2013 May 7. | Preclinical | Ascenta |
| SM-173 | Lu J, Bai L, Sun H, Nikolovska-Coleska Z, McEachern D, Qiu S, Miller R S, Yi H, Shangary S, Sun Y, Meagher J L, Stuckey J A, Wang S. SM-164: a novel, bivalent Smac mimetic that includes apoptosis and tumor regression by concurrent removal of the blockade of cIAP-1/2 and XIAP. Cancer Res. 2008 Nov. 5; 68(22):9384-93. doi: 10.1158/0008-5472.CAN-08-2655. | Preclinical | Ascenta |
| Compound 21 | Sun H, Stuckey J A, Nikolovska-Coleska Z, Qin D, Meagher J L, Qiu S, Lu J, Yang C Y, Saito N G, Wang S. Structure-based design, synthesis, evaluation, and crystallographic studies of conformationally constrained Smac mimetics as inhibitors of the X-linked inhibitor of apoptosis protein (XIAP). J Med Chem. 2008 Nov. 27;51(22):7169-80. doi: 10.1021/jm8006849. | Preclinical | Ascenta |
| WS-5 | Zhang B, Nikolovska-Coleska Z, Bai L, Qiu S, Yang C Y, Sun H, Wang S, Wu Y. Design, synthesis, and evaluation of tricyclic, conformationally constrained small-molecule mimetics of second mitochondria-derived activator of caspases. J Med Chem. 2008 Dec 11;51(23):7352-5. doi: 0.1021/jm801146d. | Preclinical | Ascenta |
| SH-130 | Dai Y, Liu M, Tang W, DeSano J, Burstein E, Davis M, Pienta K, Lawrence T, Xu L. Molecularly targeted radiosensitization of human prostate cancer by modulating inhibitor of apoptosis. Clin Cancer Res. 2008 Dec. 1;14(23): 7701-10. doi:10.1158/1078-0432.CCR-08-088. | Preclinical | Ascenta |
| SM162 | Sun H, Liu L, Lu J, Qiu S, Yang C Y, Yi H, Wang S. Cyclopeptide Smac mimetics as antagonists of IAP proteins. Bioorg Med Chem Lett. 2010 May 5;20(10):3043-6. | Preclinical | Ascenta |
| SM163 (compound 3) | Sun H, Liu L, Lu J, Qiu S, Yang C Y, Yi H, Wang S. Cyclopeptide Smac mimetics as antagonists of IAP proteins. Bioorg Med Chem Lett. 2010 May 15;20(10):3043-6. | Preclinical | Ascenta |
| SM337 | Wang S. Design of small-molecule Smac mimetics as IAP antagonists. Curr Top Microbiol Immunol. 2011;348:89-113. doi: 10.1007/82 2010 111. | Preclinical | Ascenta |
| SM122 (or SH122) | Lu J, Bai L, Sun H, Nikolovska-Coleska Z, McEachern D, Qiu S, Miller R S, Yi H, Shangary S, Sun Y, Meagher J L, Stuckey J A, Wang S, SM-164: a novel, bivalent Smac mimetic that induces apoptosis and tumor regression by concurrent removal of the blockade of cIAP-1/2 and XIAP. Cancer Res. 2008 Nov. 15;68(22):9384-93. doi: 10.1158/0008-5472.CAN-08-2655. | Preclinical | Ascenta |
| AEG40730 | Bertrand M J, Milutinovic S, Dickson K M, Ho W C, Boudreault A, Durkin J, Gillard J W, Jaquith J B, Morris S J, Barker P A. cIAP1 and cIAP2 facilitate cancer cell survival by functioning as E3 ligases that promote RIP1 ubiquitination. Mol Cell. 2008 Jun. 20;30(6):689-700. doi: 10.1016/j.molcel.2008.05.014. | Preclinical | Aegera |
| LBW242 | Keating J, Tsoli M, Hallahan A R, Ingram W J, Haber M, Ziegler D S. Targeting the inhibitor of apoptosis proteins as a novel therapeutic strategy in medulloblastoma. Mol Cancer Ther. 2012 Dec;11(12):2654-63. doi: 10.1158/1535-7163.MCT-12-0352. Epub 2012 Sep. 25. | Preclinical | Novartis |
| BV6 | Müller-Sienerth N, Dietz L, Holtz P, Kapp M, Grigoleit G U, Schmuck C, Wajant H, Siegmund D. SMAC mimetic BV6 induces cell death in monocytes and maturation of monocyte-derived dendritic cells. PLoS One. 2011;6(6):e21556. doi: 10.1371/journal.pone.0021556. Epub 2011 Jun. 30. | Preclinical | Genentech |
| MV1 | *Monomeric version of BV6*: Fulda S, Vucic D. Targeting IAP proteins for therapeutic intervention in cancer. Nat Rev Drug Discov. 2012 Feb. 1;11(2):109-24. dio: 10.1038/nrd3627. Review. Erratum in: Nat Rev Drug Discov. 2012 Apr.; 11(4):331. | Preclinical | Genentech |

TABLE 1-continued

Smac mimetic compounds

| Compound | Structure or Reference | Clinical Status | Organization; author/inventor |
|---|---|---|---|
| ATRA hybrid | Itoh Y, Ishikawa M, Kitaguchi R, Okuhira K, Naito M, Hashimoto Y. Double protein knockdown of cIAP1 and CRABP-II using a hybrid molecule consisting of ATRA and IAPs antagonist. Bioorg Med Chem Lett. 2012 Jul. 1;22(13):4453-7. doi: 10.1016/j.bmcl.2012.04.134. Epub 2012 May 23. | Preclinical | Genentech |
| SNIPER (bestatin and Estrogen receptor ligand fusion) | Okuhira K, Demizu Y, Hattori T, Ohoka N, Shibata N, Nishimaki-Mogami T, Okuda H, Kurihara M, Naito M. Development of hybrid small molecules that induces degradation of estrogen receptor-alpha and necrotic cell death in breast cancer cells. Cancer Sci. 2013 Aug. 30. doi: 10.1111/cas.12272. [Epub ahead of print] | Preclinical | |
| RMT5265 | Ramachandiran S, Cain J, Liao A, He Y, Guo X, Boise L H, Fu H, Ratner L, Khoury H J, Bernal-Mizrachi L. The Smac mimetic RMT5265.2HCL induces apoptosis in EBV and HTLV-I associated lymphoma cells by inhibiting XIAP and promoting the mitochondrial release of cytochrome C and Smac. Leuk Res. 2012 Jun;36(6):784-90. doi: 10.1016/j.leukres.2011.12.024. Epub 2012 Feb. 10; Li L, Thomas R M, Suzuki H, De Brabander J K, Wang X, Harran P G. A small molecule Smac mimic potentiates TRAIL- and TNFalpha-mediated cell death. Science. 2004 Sep. 3;305(5689):1471-4. | Preclincal | Joyant (USA) |
| JP1010 | Probst B L, Liu L, Ramesh V, Li L, Sun H, Minna J D, Wang L. Smac mimetics increase cancer cell response to chemotherapeutics in a TNF-α-dependent manner. Cell Death Differ. 2010 October;17(10):1645-54. doi: 10.1038/cdd.2010.44. Epub 2010 Apr. 30. | Preclinical | Joyant (USA) |
| JP1400 | Probst B L, Liu L, Ramesh V, Li L, Sun H, Minna J D, Wang L. Smac mimetics increase cancer cell response to chemotherapeutics in a TNF-α-dependent manner. Cell Death Differ. 2010 October;17(10):1645-54. doi: 10.1038/cdd.2010.44. Epub 2010 Apr. 30. | Preclinical | Joyant (USA) |
| ABT-10 | | Preclinical | Abbott |
| A-410099.1 | Oost T K, Sun C, Armstrong R C, Al-Assaad A S, Betz S F, Deckwerth T L, Ding H, Elmore S W, Meadows R P, Olejniczak E T, Oleksijew A, Oltersdorf T, Rosenberg S H, Shoemaker A R, Tomaselli K J, Zou H, Fesik S W. Discovery of potent antagonists of the antiapoptotic protein XIAP for the treatment of cancer. J Med Chem. 2004 Aug. 26;47(18):4417-26. | Preclinical | Abbott |
| 822B | Jae Sik Shin, Seung-Woo Hong, Dong-Hoon Jin, In-Hwan Bae, Maeng-Sug Kim, Young-Soon Na, Jae-Lyun Lee, Yong Sang Hong, and Tae-Won Kim. Abstract 592: Novel IAP antagonist (822B) induces apoptosis through degradation of IAP proteins which have a BIR3 domain in human pancreatic cancer cells. *Cancer Research*: Apr. 15, 2011; Volume 71, Issue 8, Supplement 1 doi: 10.1158/1538-7445.AM011-592 Proceedings: AACR 102nd Annual Meeting 2011 Apr. 2-6, 2011; Orlando, FL | Preclinical | Hanmi (Korea) |
| GT13402 | | Preclinical | Tetralogic |
| SWiii-123 (sigma2R ligand hybrid) | Zeng C, Vangveravong S, McDunn J E, Hawkins W G, Mach R H, Sigma-2 receptor ligand as a novel method for delivering a SMAC mimetic drug for treating ovarian cancer. Br J Cancer. 2013 Oct. 29;109(9):2368-77. doi: 10.1038/bjc.2013.593. Epub 2013 Oct. 8. | Preclinical | (R H Mach) |
| | | Preclinical | Apoptos (USA) |
| | | Preclinical | Sanofi-Aventis/Synthelabo (EU) |

Immunostimulatory Agents

An immunostimulatory or immunomodulatory agent of the present invention may be any agent capable of inducing a receptor-mediated apoptotic program that is inhibited by cIAP1 and cIAP2 in one or more cells of a subject. An immune stimulant of the present invention may induce an apoptotic program regulated by cIAP1 (BIRC2), cIAP2 (BIRC3 or API2), and optionally, one or more additional IAPs, e.g., one or more of the human IAP proteins NAIP (BIRC1), XIAP (BIRC4), survivin (BIRC5), Apollon/Bruce (BIRC6), ML-IAP (BIRC7 or livin), and ILP-2 (BIRC8). It is additionally known that various immunomodulatory or immunostimulatory agents, such as CpGs or IAP antagonists, can change immune cell contexts.

In some instances, an immune stimulant may be a TLR agonist, such as a TLR ligand. A TLR agonist of the present invention may be an agonist of one or more of TLR-1, TLR-2, TLR-3, TLR-4, TLR-5, TLR-6, TLR-7, TLR-8, TLR-9, and TLR-10 in humans or related proteins in other species (e.g., murine TLR-1 to TLR-9 and TLR-11 to TLR-13). TLRs can recognize highly conserved structural motifs known as pathogen-associated microbial patterns (PAMPs), which are exclusively expressed by microbial pathogens, as well as danger-associated molecular patterns (DAMPs) that are endogenous molecules released from necrotic or dying cells. PAMPs include various bacterial cell wall components such as lipopolysaccharide (LPS), peptidoglycan (PGN), and lipopeptides, as well as flagellin, bacterial DNA, and viral double-stranded RNA. DAMPs include intracellular proteins such as heat shock proteins as well as protein fragments from the extracellular matrix. Agonists of the present invention further include, for example, CpG oligodeoxynucleotides (CpG ODNs), such as Class A, B, and C CpG ODN's, base analogs, nucleic acids such as dsRNA or pathogen DNA, or pathogen or pathogen-like cells or virions. In certain embodiments, the immunostimulatory agent is an agent that mimics a virus or bacteria or is a synthetic TLR agonist.

Various TLR agonists are known in the art. Non-limiting examples of TLR agonists are provided in Table 2. While Table 2 includes suggested mechanisms, uses, or TLR targets by which various TLR agonists may function, methods and compositions of the present invention are not limited by or to these mechanisms, uses, or targets.

TABLE 2

Immunostimulatory agents: TLR Agonists

| Compound | Structure or Reference |
|---|---|
| Poly-ICLC (polyinosinic:polycytidylic acid; poly(I:C)) | Levy H B. Historical overview of the use of polynucleotides in cancer. J Biol Response Mod. 1985;4:475-480. 7. Levy H B. Induction of interferon in vivo by polynucleotides. Tex Rep Biol Med. 1977;35:91-98. |
| Poly(A:U) polyadenylic-polyuridylic acid | Ducret J P, Caillé P, Sancho Garnier H, et al. A phase I clinical tolerance study of polyadenylic-polyuridylic acid in cancer patients. J Biol Response Mod 1985;4:129-133. Polyadenylic.polyuridylic acid in the cotreatment of cancer. Michelson A M, Lacour F, Lacour J. Proc Soc Exp Biol Med. 1985 May;179(1):1-8. |
| CL075 | Gorden KB, et al., 2005. Synthetic TLR agonists reveal functional differences between human TLR7 and TLR8. J Immunol. 174(3):1259-68; InvivoGen, InvivoGen Insight (Company Newsletter) Spring 2013: 8 pages.<br>Formula: $C_{13}H_{13}N_3S$<br>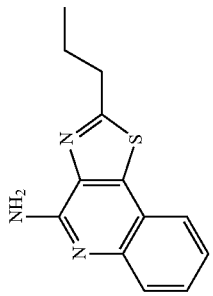 |
| CL097 | Salio M. et al., 2007. Modulation of human natural killer T cell ligands on TLR-mediated antigen-presenting cell activation. PNAS 104: 20490-20495. Butchi nJ. et al., 2008. Analysis of the Neuroinflammatory Response to TLR7 Stimulation in the Brain: Comparison of Multiple TLR7 and/or TLR8 Agonists J Immunol 180: 7604-7612 |

TABLE 2-continued
Immunostimulatory agents: TLR Agonists
| CL264 | U.S. Patent Publication No. 20110077263<br>Formula: $C_{19}H_{23}N_7O_4$ | 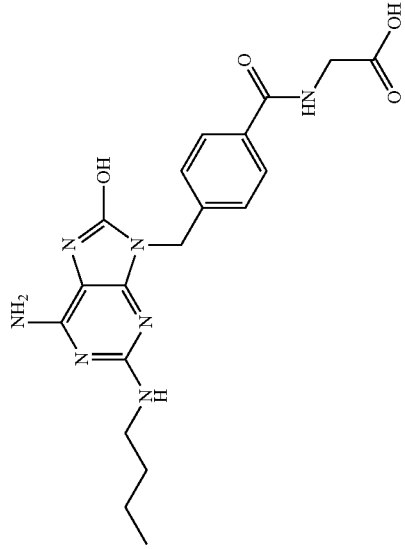 |
| CL307<br>Gardiquimod ™ | U.S. Patent Publication No. 20110077263<br>Formula: $C_{17}H_{23}N_5O$ | 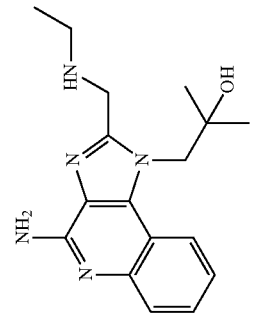 |

TABLE 2-continued

Immunostimulatory agents: TLR Agonists

| | |
|---|---|
| Loxoribine | Gorden KB. et al., 2005. Synthetic TLR agonists reveal functional differences between human TLR7 and TLR8. J Immunol. 174(3):1259-68. 2. Schindler U. & Baichwal VR., 1994. Three NF-kB binding sites in the human E-selectin gene required for maximal tumor necrosis factor alpha-induced expression. Mol Cell Biol, 14(9):5820-5831. Formula: $C_{13}H_{17}N_5O_6$ 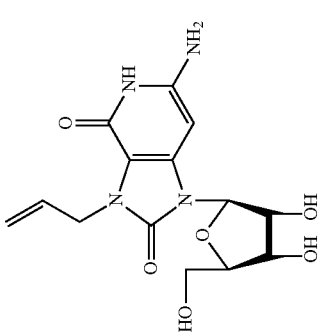 |
| Poly(dT) | Jurk M. et al., 2006. Modulating responsiveness of human TLR7 and 8 to small molecule ligands with T-rich phosphorothiate oligodeoxynucleotides. Eur J Immunol. 36(7):1815-26. 2. Gorden KKB. et al., 2006. Oligodeoxynucleotides Differentially Modulate Activation of TLR7 and TLR8 by Imidazoquinolines. J. Immunol. 177: 8164-8170. 3. Gorden KKB. et al., 2006. Cutting Edge: Activation of Murine TLR8 by a Combination of Imidazoquinoline Immune Response Modifiers and Poly T Oligodeoxynucleotides J. Immunol., 177: 6584-6587. |
| R848 | Hemmi H. et al. 2002. Small anti-viral compounds activate immune cells via the TLR7 MyD88-dependent signaling pathway. Nat Immunol, 3(2):196-200. 2. Jurk m. et al. 2002. Human TLR7 or TLR8 independently confer responsiveness to the antiviral compound R848. Nat Immunol, 3(6):499. 3. Gorden KKB. et al., 2006. Cutting Edge: Activation of Murine TLR8 by a Combination of Imidazoquinoline Immune Response Modifiers and PolyT Oligodeoxynucleotides J. Immunol., 177: 6584-6587 Formula: $C_{17}H_{22}N_4O_2$, HCl 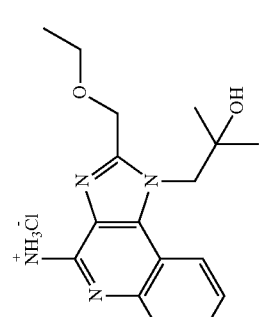 |
| ODN 1585 | Ballas Z K. et al., 2001. Divergent therapeutic and immunologic effects of oligodeoxynucleotides with distinct CpG motifs. J Immunol. 167(9):4878-86 |
| ODN 2216 | Ballas Z K. et al., 2001. Divergent therapeutic and immunologic effects of oligodeoxynucleotides with distinct CpG motifs. J Immunol. 167(9):4878-86 |
| ODN 2336 | |

TABLE 2-continued

Immunostimulatory agents: TLR Agonists

| | |
|---|---|
| ODN 1668 | Heit A. et al., 2004. CpG-DNA aided cross-priming by cross-presenting B cells. J Immunol. 172(3):1501-7 |
| ODN 1826 | Z Moldoveanu, L Love-Homan, W. Q Huang, A. M Krieg CpG DNA, a novel immune enhancer for systemic and mucosal immunization with influenza virus Vaccine, 16 (1998), pp. 1216-1224 |
| ODN 2006 (ODN 7909 or PF-3512676) | Z Moldoveanu, L Love-Homan, W. Q Huang, A. M Krieg CpG DNA, a novel immune enhancer for systemic and mucosal immunization with influenza virus Vaccine, 16 (1998), pp. 1216-1224 |
| ODN 2007 | Krieg, A; CpG motifs in bacterial DNA and their immune effects. Annu Rev Immunol 2002. 20: 709 |
| ODN 2395 | Roda J M. et al., 2005. CpG-containing oligodeoxynucleotides act through TLR9 to enhance the NK cell cytokine response to antibodycoated tumor cells. J Immunol. 175(3):1619-27. |
| ODN M362 | Hartmann G, Battiany J, Poeck H, et al.: Rational design of new CpG oligonucleotides that combine B cell activation with high IFN-alpha induction in plasmacytoid dendritic cells. Eur J Immunol 2003; 33:1633-41 |
| ODN 1018 | Magone, M. T., Chan, C. C., Beck, L., Whitcup, S. M., Raz, E. (2000) Systemic or mucosal administration of immunostimulatory DNA inhibits early and late phases of murine allergic conjunctivitis Eur. J. Immunol. 30, 1841-1850 |
| CL401 | Formula: $C_{54}H_{92}N_8O_4S$ |

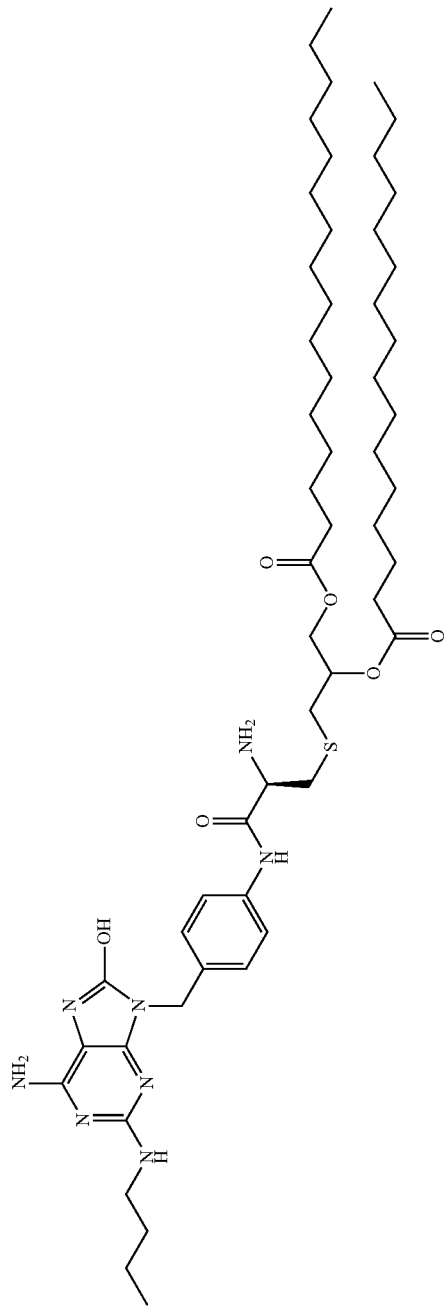

TABLE 2-continued
Immunostimulatory agents: TLR Agonists
| Adilipoline ™ (CL413;) | Formula: $C_{81}H_{145}N_{17}O_{12}S$ | 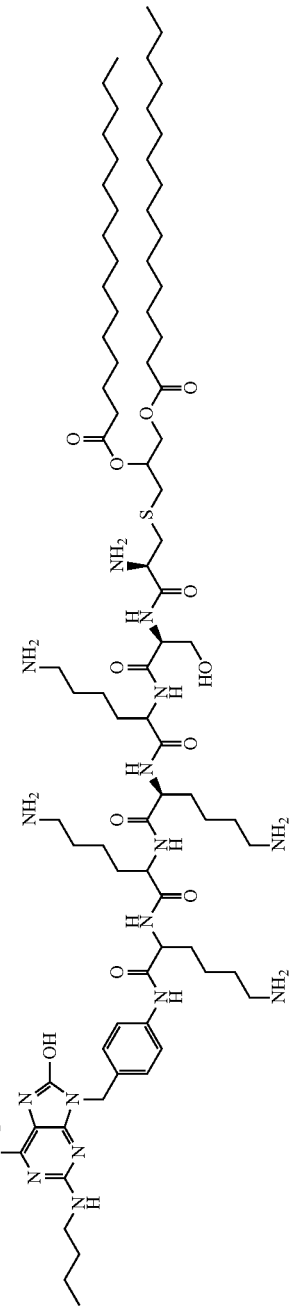 |
| CL531 | Formula: $C_{82}H_{144}N_{16}O_{14}S$ | 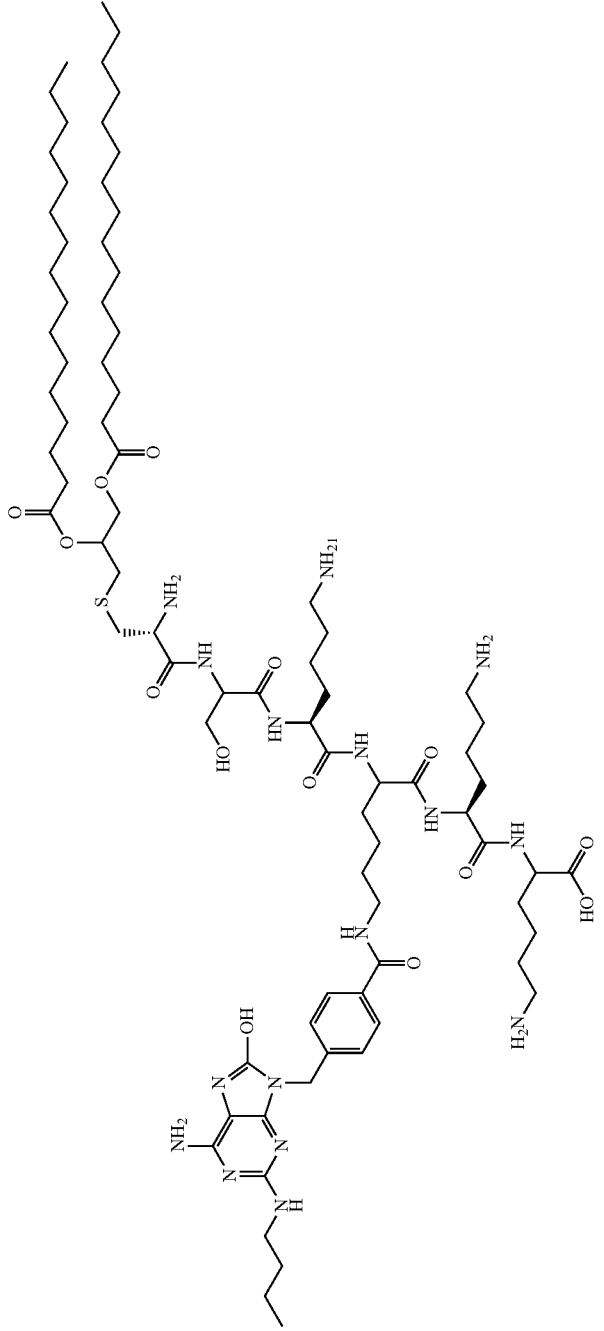 |

TABLE 2-continued
Immunostimulatory agents: TLR Agonists
| | |
|---|---|
| CL572 | Formula: $C_{41}H_{65}N_9O_7S$ 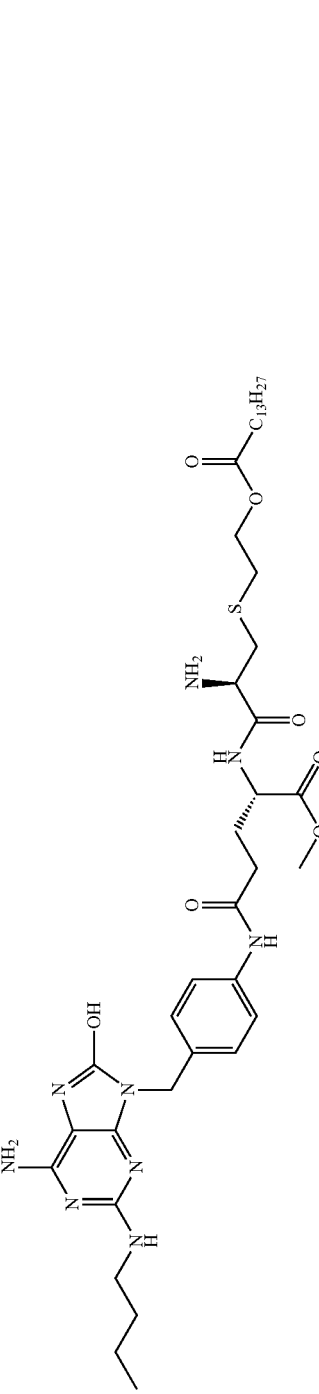 |
| AdiFectin ™ (CL347;) | Formula: $C_{72}H_{134}N_{11}O_6P$ 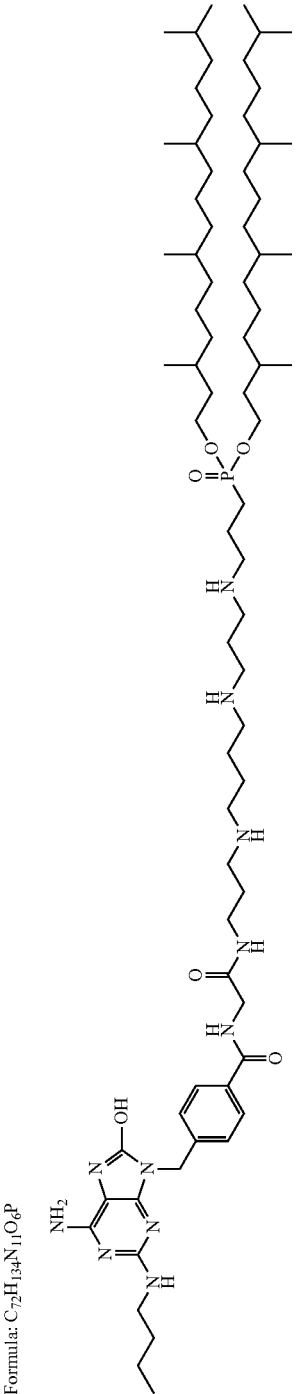 |
| CL419 | Formula: $C_{48}H_{97}N_5O_5S$ 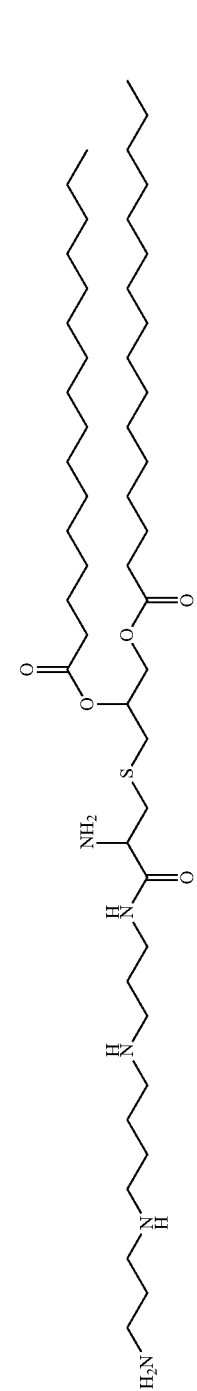 |

TABLE 2-continued

Immunostimulatory agents: TLR Agonists

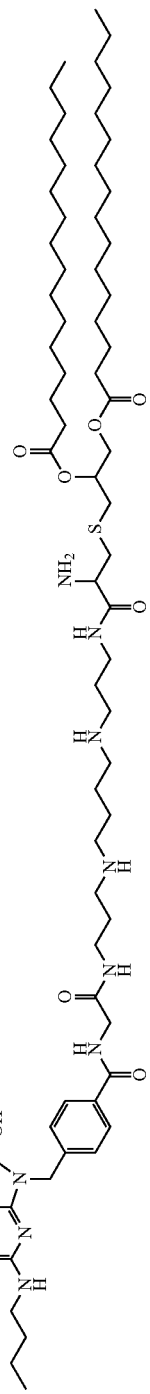

| PamadiFectin ™ (CL553;) | Formula: $C_{67}H_{118}N_{12}O_8S$ |
| --- | --- |
| Peptidoglycan | |
| Diacylated lipopeptide | Buwitt-Beckmann u. et al., 2005. Toll-like receptor 6-independent signaling by diacylated lipopeptides. Eur J Immunol. 35(1):282-9 |
| Triacylated lipopeptide | Aliprantis ao et al., 1999. Cell activation and apoptosis by bacterial lipoproteins through toll-like receptor-2. Science.285(5428):736-9. Ozinsky a. et al., 2000. The repertoire for pattern recognition of pathogens by the innate immune system is defined by cooperation between toll-like receptors. PNAS. 97(25):13766-71.3 |
| Lipopolysaccharide (LPS) | N/A |
| CpG 7909 | |
| 852A | |
| Ampligen | |
| Resiquimod | |
| ANA975 | |
| Imiquimod (InvivoGen) | |
| Monophosphoryl lipid A (MPL) | |
| CpG 7909 (i.e., PF-3512676) | |
| CpG 1018 ISS | |
| Bacillus Calmette-Guérin (BCG) | N/A |
| Zymosan A | |

| Compound | Compound Type or Application | Agonist of: |
| --- | --- | --- |
| Poly-ICLC (polyinosinic:polycytidylic acid; poly(I:C)) | Intratumoral admininstration for treatment of mesothelioma (see, e.g., Currie A J, Van Der Most R G, Broomfield S A, Prosser A C, Tovey M G, Robinson B W. Targeting the effector site with IFN-αβ-inducing TLR ligands reactivates tumor-resident CD8 T cell responses to eradicate established solid tumors. J. Immunol. 2008; 180(3):1535-1544.) | Toll-like receptor (TLR)-3 |
| Poly(A:U) polyadenylic-polyuridylic acid | Synthetic double stranded RNA molecule | TLR-3 |
| CL075 | Thiazoquinoline compound | TRL-7 or TLR-7/8 |
| CL097 | Imidazoquinline compound | TRL-7 or TLR-7/8 |
| CL264 | Adenine analog | TRL-7 or TLR-7/8 |

TABLE 2-continued

Immunostimulatory agents: TLR Agonists

| Name | Description | Target |
|---|---|---|
| CL307 | Base analog | TRL-7 or TLR-7/8 |
| Gardiquimod ™ | Imidazoquinoline compound | TRL-7 or TLR-7/8 |
| Loxoribine | Guanosine analog | TRL-7 or TLR-7/8 |
| Poly(dT) | Thymidine homopolymer ODN (17 mer) | TRL-7 or TLR-7/8 |
| R848 | Imidazoquinoline compound | TRL-7 or TLR-7/8 |
| ODN 1585 | Class A CpG ODN | TLR-9 |
| ODN 2216 | Class A CpG ODN | TLR-9 |
| ODN 2336 | Class A CpG ODN | TLR-9 |
| ODN 1668 | Class B CpG ODN | TLR-9 |
| ODN 1826 | Class B CpG ODN | TLR-9 |
| ODN 2006 (ODN 7909 or PF-3512676) | Class B CpG ODN | TLR-9 |
| ODN 2007 | Class B CpG ODN | TLR-9 |
| ODN 2395 | Class C CpG ODN | TLR-9 |
| ODN M362 | Class C CpG ODN | TLR-9 |
| ODN 1018 | Class B | TLR-9 agonist |
| CL401 | Dual TLR agonist | TLR-2 and TLR-7 |
| Adilipoline ™ (CL413;) | Dual TLR agonist | TLR-2 and TLR-7 |
| CL531 | Dual TLR agonist | TLR-2 and TLR-7 |
| CL572 ( | Dual TLR agonist | Human TLR-2, mouse TLR-7, and human TLR-7 |
| AdiFectin ™ (CL347;) | TLR agonist and nucleic acid carrier | TLR-7 |
| CL419 | TLR agonist and nucleic acid carrier | TLR-2 |
| ParnadiFectin ™ (CL553;) | TLR agonist and nucleic acid carrier | TLR-2 and TLR-7 |
| Peptidoglycan | TLR agonist; cell surface location (*Expert Rev Clin Pharmacol* 4(2):275-289, 2011) | TLR-1/2; TLR-2/6 |
| Diacylated lipopeptide | TLR ligand; cell surface location | TLR-2/6 |
| Triacylated lipopeptide | TLR ligand; cell surface location | TLR-1/2 |
| Lipopolysaccharide (LPS) | TLR ligand; cell surface location; intratumoral administration for treatment of glioma. (see, e.g., Mariani C L, Rajon D, Bova F J, Streit W J. Nonspecific immunotherapy with intratumoral lipopolysaccharide and zymosan A but not GM-CSF leads to an effective anti-tumor response in subcutaneous RG-2 gliomas. J. Neurooncol. 2007; 85(3):231-240.) | TLR-4 |
| CpG 7909 | Intravenous administration for treatment of non-Hodgkin lymphoma. (see. e.g., Link B K, Ballas Z K, Weisdorf D, et al. Oligodeoxynucleotide CpG 7909 delivered as intravenous infusion demonstrates immunologic modulation in patients with previously treated non-Hodgkin lymphoma. J. Immunother. 2006; 29(5):558-568.) | TLR-9 |
| 852A | Intravenous administration for treatment of melanoma and other cancer [12, 55]; (see, e.g., Dudek A Z, Yunis C, Harrison L I, et al. First in human Phase I trial of 852A, a novel systematic Toll-like receptor 7 agonist, to activate innate immune responses in patients with advanced cancer. Clin. Cancer Res. 2007; 13(23):7119-7125'; Dummer R, Hauschild A, Becker J C, et al. An exploratory study of systemic administration of the Toll-like receptor-7 agonist 852A in patients with refractory metastatic melanoma. Clin. Cancer Res. 2008; 14(3):856-864. intravenous administration for treatment of chronic lymphocytic leukemia (see, e.g., Spaner D E, Shi Y, White D, et al. A Phase I/II trial of TLR7 agonist immunotherapy in chronic lymphocytic leukemia. Leukemia. 2010; 24(1):222-226.) | TLR-7 |
| Ampligen | Intravenous administration for treatment of chronic fatigue syndrome [60]; intravenous administration for treatment of HIV (see, e.g. Thompson K A, Strayer D R, Salvato P D, et al. Results of a double-blind placebo-controlled study of the double-stranded RNA drug poly:polyC12U in the treatment of HIV infection. Eur. J. Clin. Microbiol. Infect. Dis. 1996; 15(7):580-587. [PubMed: 8874076]) | TLR-3 |

TABLE 2-continued

Immunostimulatory agents: TLR Agonists

| | | |
|---|---|---|
| Resiquimod | Oral administration for treatment of hepatitis C ((see, e.g., Pockros P J, Guyader D, Patton H, et al. Oral resiquimod in chronic HCV infection: safety and efficacy in 2 placebo-controlled, double-blind Phase IIa studies, J. Hepatol. 2007; 47(2):174-182.); Topical administration for treatment of Herpes simplex virus 2 (see, e.g., Mark K E, Corey L, Meng T C, et al. Topical resiquimod 0.01% gel decreases herpes simplex virus type 2 genital shedding: a randomized, controlled trial. J. Infect. Dis. 2007; 195(9):1342-1331.) | TLR-7/8 |
| ANA975 | Oral administration for treatment of hepatitis (see, e.g., Fletcher S, Steffy K, Averett D. Masked oral prodrugs of Toll-like receptor 7 agonists: a new approach for the treatment of infectious disease. Curr. Opin. Investig. Drugs. 2006; 7(8):702-708.) | TLR-7 |
| Imiquimod (InvivoGen) | Imidazoquinoline compound; topical administration for treatment of basal cell carcinoma (see, e.g., Schulze H J, Cribier B, Requena L, et al. Imiquimod 5% cream for the treatment of superficial basal cell carcinoma: results from a randomized vehicle-controlled Phase III study in Europe. Br. J. Dermatol. 2005; 152(5):939-947; Quirk C, Gebauer K, Owens M, Stampone P. Two-year interim results from a 5-year study evaluating clinical recurrence of superficial basal cell carcinoma after treatment with imiquimod 5% cream daily for 6 weeks. Australas J. Dermatol. 2006; 47(4):258-265.); Topical administration for treatment of squamous cell carcinoma (see, e.g., Ondo A L, Mings S M. Pestak R M, Shanler S D. Topical combination therapy for cutaneous squamous cell carcinoma in situ with 5-fluorouracil cream and imiquimod cream in patients who have failed topical monotherapy. J. Am. Acad. Dermatol. 2006; 55(6):1092-1094). Topical administration for treatment of melanoma (see, e.g., Turza K, Dengel L T, Harris R C, et al. Effectiveness of imiquimod limited to dermal melanoma metastases, with simultaneous resistance of subcutaneous metastasis. J. Cutan. Pathol. 2009 DOI: 10.1111/j.1600-0560.2009.01290.x. (Epub ahead of print); (see, e.g., Green D S, Dalgleish A G, Belonwu N, Fischer M D, Bodman-Smith M D. Topical imiquimod and intralesional interleukin-2 increase activated lymphocytes and restore the Th1/Th2 balance in patients with metastatic melanoma. Br. J. Dermatol. 2008; 159(3):606-614.); Topical administration for treatment of vulvar intraepithelial neoplasia (see, e.g., Van Seters M, Van Beurden M, Ten Kate F J, et al. Treatment of vulvar intraepithelial neoplasia with topical imiquimod. N. Engl. J. Med. 2008; 358(14):1465-1473.); Topical administration for treatment of cutaneous lymphoma (see, e.g., Stavrakoglou A, Brown V L, Coutts I. Successful treatment of primary cutaneous follicle centre lymphoma with topical 5% imiquimod. Br. J. Dermatol. 2007; 157(3):620-622.); Topical treatment as Human papillomavirus (HPV) vaccine (see, e.g., Daayana S, Elkord E, Winters U, et al. Phase II trial of imiquimod and HPV therapeutic vaccination in patients with vulval intraepithelial neoplasia. Br. J. Cancer. 2010; 102(7):1129-1136); Subcutaneous/intramuscular administration: New York esophageal squamous cell carcinoma 1 cancer antigen (NY-ESO-1) protein vaccine for melanoma (see, e.g., Adams S, O'Neill D W, Nonaka D, et al. Immunization of malignant melanoma patients with full-length NY-ESO-1 protein using TLR7 agonist imiquimod as vaccine adjuvant. J. Immunol. 2008; 181(1):776-784.) | TLR-7 |
| Monophosphoryl lipid A (MPL) | Subcutaneous/intramuscular administration for vaccination against HPV (see, e.g., Harper D M Franco E L, Wheeler C M, et al. Sustained efficacy up to 4.5 years of a bivalent L1 virus-like particle vaccine against human papillomavirus types 16 and 18: follow-up from arandomised control trial. Lancet. 2006; 367(9518):1247-1255.); Subcutaneous/intramuscular administration for vaccination against non-small-cell lung cancer (see, e.g., Butts C, Murray N, Maksymiuk A, et al. Randomized Phase IIB trial of BLP25 liposome vaccine in stage IIIB and IV non-small-cell lung cancer. J. Clin. Oncol. 2005; 23(27):6674-6681.) | TLR-4 |
| CpG 7909 (i.e., PF-3512676) | Subcutaneous/intramuscular administration for treatment of non-small-cell lung cancer (see, e.g., Manegold C, Gravenor D, Woytowitz D, et al. Randomized Phase II Trial of a Toll-like receptor 9 agonist oligodeoxynucleotide, PF-3512676, in combination with first-line taxane plus platinum chemotherapy for advanced-stage non-small-cell lung cancer. J. Clin. Oncol. 2008; 26(24):3979-3986; Readett, D.; Denis, L.; Krieg, A.; Benner, R.; Hanson, D. PF-3512676 (CPG 7909) a Toll-like receptor 9 agonist-status of development for non-small cell lung cancer (NSCLC). Presented at: 12th World Congress on Lung Cancer; Seoul, Korea. 2-6 Sept, 2007); Subcutaneous/intramuscular administration for treatment of metastatic melanoma (see, e.g., | TLR-9 |

TABLE 2-continued

Immunostimulatory agents: TLR Agonists

| | | |
|---|---|---|
| | Pashenkov M, Goess G, Wagner C, et al. Phase II trial of a Toll-like receptor 9-activating oligonucleotide in patients with metastatic melanoma. J. Clin. Oncol. 2006; 24(36):5716-5724.; Subcutaneous/intramuscular administration; Melan-A peptide vaccine for melanoma (see, e.g., Speiser D E, Lienard D, Rufer N, et al. Rapid and strong human CD8+ T cell responses to vaccination with peptide, IFA, and CpG oligodeoxynucleotide 7909. J. Clin. Invest. 2005; 115(3): 739-746; Appay V, Jandus C, Voelter V, et al. New generation vaccine induces effective melanoma-specific CD8+ T cells in the circulation but not in the tumor site. J. Immunol. 2006; 177(3):1670-1678.); Subcutaneous/intramuscular administration; NY-ESO-1 protein vaccine (see, e.g., Valmori D, Souleimanian N E, Tosello V, et al. Vaccination with NY-ESO-1 protein and CpG in Montanide induces integrated antibody/Th1 responses and CD8 T cells through cross-priming. Proc. Natl. Acad. Sci. USA. 2007; 104(21):8947-8952.) | |
| CpG 1018 ISS | Subcutaneous/intramuscular administration for treatment of lymphoma (see, e.g., Friedberg J W, Kim H, McCauley M, et al. Combination immunotherapy with a CpG oligonucleotide (1018 ISS) and rituximab in patients with non-Hodgkin lymphoma: increased interferon-α/β-inducible gene expression, without significant toxicity. Blood. 2005; 105(2):489-495; Friedberg J W, Kelly J L, Neuberg D, et al. Phase II study of a TLR-9 agonist (1018 ISS) with rituximab in patients with relapsed or refractory follicular lymphoma. Br. J. Haematol. 2009; 146(3):282-291.) | TLR-9 |
| Bacillus Calmette-Guérin (BCG) | Intratumoral administration for treatment of bladder cancer (see, e.g., Simons M P, O'Donnell M A. Griffith T S. Role of neutrophils in BCG immunotherapy for bladder cancer. Urol. Oncol. 2008; 26(4):341-345.) | TLR-2 |
| Zymosan A | Intratumoral administration for treatment of glioma (see, e.g., Mariani C L, Rajon D, Bova F J, Streit W J. Nonspecific immunotherapy with intratumoral lipopolysaccharide and zymosan A but not GM-CSF leads to an effective anti-tumor response in subcutaneous RG-2 gliomas. J. Neurooncol. 2007; 85(3):231-240.) | TLR-2 |

In other instances, an immune stimulant may be a virus, e.g., an oncolytic virus. An oncolytic virus is a virus that selectively infects, replicates, and/or selectively kills cancer cells. Viruses of the present invention include, without limitation, adenoviruses, Herpes simplex viruses, measles viruses, Newcastle disease viruses, parvoviruses, polioviruses, reoviruses, Seneca Valley viruses, retroviruses, Vaccinia viruses, vesicular stomatitis viruses, lentiviruses, rhabdoviruses, sindvis viruses, coxsackieviruses, poxviruses, and others. In particular embodiments of the present invention, the immunostimulatory agent is a rhabodvirus, e.g., VSV. Rhabdoviruses can replicate quickly with high IFN production. In other particular embodiments, the immunostimulatory agent is a feral member, such as Maraba virus, with the MG1 double mutation, Farmington virus, Carajas virus. Viral immunostimulatory agents of the present invention include mutant viruses (e.g., VSV with a Δ51 mutation in the Matrix, or M, protein), transgene-modified viruses (e.g., VSV-hIFNβ), viruses carrying -TNFα, -LTα/-TNFβ, -TRAIL, FasL, -TL1α, chimeric viruses (eg rabies), or pseudotyped viruses (e.g., viruses pseudotyped with G proteins from LCMV or other viruses). In some instances, the virus of the present invention will be selected to reduce neurotoxicity. Viruses in general, and in particular oncolytic viruses, are known in the art.

In certain embodiments, the immunostimulatory agent is a killed VSV NRRP particle or a prime-and-boost tumor vaccine. NRRPs are wild type VSV that have been modified to produce an infectious vector that can no longer replicate or spread, but that retains oncolytic and immunostimulatory properties. NRRPs may be produced using gamma irradiation, UV, or busulfan. Particular combination therapies include prime-and-boost with adeno-MAGE3 (melanoma antigen) and/or Maraba-MG1-MAGE3. Other particular combination therapies include UV-killed or gamma irradiation-killed wild-type VSV NRRPs. NRRPs may demonstrate low or absent neurotixicity. NRRPs may be useful, e.g., in the treatment of glioma, hematological (liquid) tumors, or multiple myeloma.

In some instances, the immunostimulatory agent of the present invention is a vaccine strain, attenuated virus or microorganism, or killed virus or microorganism. In some instances, the immunostimulatory agent may be, e.g., BCG, live or dead Rabies vaccines, or an influenza vaccine.

Non-limiting examples of viruses of the present invention, e.g., oncolytic viruses, are provided in Table 3. While Table 3 includes suggested mechanisms or uses for the provided viruses, methods and compositions of the present invention are not limited by or to these mechanisms or uses.

TABLE 3

Immunostimulatory agents

| Strain | Modification(s)/ Description | Virus | Clinical Trial; Indication; Route; Status; Reference |
| --- | --- | --- | --- |
| Oncorine (H101) | E1B-55k– | Adenovirus | Phase 2; SCCHN; intratumoral (IT); completed; Xu RH, Yuan ZY, Guan ZZ, Cao Y, Wang HQ, Hu XH, Feng JF, Zhang Y, Li F, Chen ZT, Wang JJ, Huang JJ, Zhou QH, Song ST. [Phase II clinical study of intratumoral H101, an E1B deleted adenovirus, in combination with chemotherapy in patients with cancer]. Ai Zheng. 2003 Dec; 22(12): 1307-10. Chinese. |
| Oncorine (H101) | E3– | Adenovirus | Phase 3; SCCHN; IT; Completed; Xia ZJ, Chang JH, Zhang L, Jiang WQ, Guan ZZ, Liu JW, Zhang Y, Hu XH, Wu GH, Wang HQ, Chen ZC, Chen JC, Zhou QH, Lu JW, Fan QX, Huang JJ, Zheng X. [Phase III randomized clinical trial of intratumoral injection of E1B gene-deleted adenovirus (H101) combined with cisplatin-based chemotherapy in treating squamous cell cancer of head and neck or esophagus]. Ai Zheng. 2004 Dec; 23(12): 1666-70. Chinese. |
| Onyx-015 | E1B-55k– | Adenovirus | Phase 1; Lung Mets; intravenous (IV); Completed; Nemunaitis J, Cunningham C, Buchanan A, Blackburn A, Edelman G, Maples P, Netto G, Tong A, Randlev B, Olson S, Kirn D. Intravenous infusion of a replication-selective adenovirus (ONYX-015) in cancer patients: safety, feasibility and biological activity. Gene Ther. 2001 May; 8(10): 746-59. |
| Onyx-015 | E3B– | Adenovirus | Phase 1; Glioma; Intracavity; Completed; Chiocca EA, Abbed KM, Tatter S, Louis DN, Hochberg FH, Barker F, Kracher J, Grossman SA, Fisher JD, Carson K, Rosenblum M, Mikkelsen T, Olson J, Markert J, Rosenfeld S, Nabors LB, Brem S, Phuphanich S, Freeman S, Kaplan R, Zwiebel J. A phase I open-label, dose-escalation, multi-institutional trial of injection with an E1B-Attenuated adenovirus, ONYX-015, into the peritumoral region of recurrent malignant gliomas, in the adjuvant setting. Mol Ther. 2004 Nov; 10(5): 958-66. Phase 1; Ovarian cancer; intraperitoneal (IP); Completed; Vasey PA, Shulman LN, Campos S, Davis J, Gore M, Johnston S, Kirn DH, O'Neill V, Siddiqui N, Seiden MV, Kaye SB. Phase I trial of intraperitoneal injection of the E1B-55-kd-gene-deleted adenovirus ONYX-015 (dl1520) given on days 1 through 5 every 3 weeks in patients with recurrent/refractory epithelial ovarian cancer. J Clin Oncol. 2002 Mar 15; 20(6): 1562-9. Phase 1; SCCHN; IT; Completed; Ganly I, Kirn D, Eckhardt G, Rodriguez GI, Soutar DS, Otto R, Robertson AG, Park O, Gulley ML, Heise C, Von Hoff DD, Kaye SB. A phase I study of Onyx-015, an E1B attenuated adenovirus, administered intratumorally to patients with recurrent head and neck cancer. Clin Cancer Res. 2000 Mar; 6(3): 798-806. Erratum in: Clin Cancer Res 2000 May; 6(5): 2120. Clin Cancer Res 2001 Mar; 7(3): 754. Eckhardt SG [corrected to Eckhardt G]. Phase 1; Solid tumors; IV; Completed; Nemunaitis J, Senzer N, Sarmiento S, Zhang YA, Arzaga R, Sands B, Maples P, Tong AW. A phase I trial of intravenous infusion of ONYX-015 and enbrel in solid tumor patients. Cancer Gene Ther. 2007 Nov; 14(11): 885-93. Epub 2007 Aug 17. Phase 1; Sarcoma; IT; Completed; Galanis E, Okuno SH, Nascimento AG, Lewis BD, Lee RA, Oliveira AM, Sloan JA, Atherton P, Edmonson JH, Erlichman C, Randlev B, Wang Q, Freeman S, Rubin J. Phase I-II trial of |

TABLE 3-continued

Immunostimulatory agents

| Strain | Modification(s)/Description | Virus | Clinical Trial; Indication; Route; Status; Reference |
|---|---|---|---|
| | | | ONYX-015 in combination with MAP chemotherapy in patients with advanced sarcomas. Gene Ther. 2005 Mar; 12(5): 437-45.<br>Phase 1/2; PanCa; IT; Completed; Hecht JR, Bedford R, Abbruzzese JL, Lahoti S, Reid TR, Soetikno RM, Kirn DH, Freeman SM. A phase I/II trial of intratumoral endoscopic ultrasound injection of ONYX-015 with intravenous gemcitabine in unresectable pancreatic carcinoma. Clin Cancer Res. 2003 Feb; 9(2): 555-61.<br>Phase 2; CRC; IV; Completed; Hamid O, Varterasian ML, Wadler S, Hecht JR, Benson A 3rd, Galanis E, Uprichard M, Omer C, Bycott P, Hackman RC, Shields AF. Phase II trial of intravenous CI-1042 in patients with metastatic colorectal cancer. J Clin Oncol. 2003 Apr 15; 21(8): 1498-504.<br>Phase 2; Hepatobiliary; IT; Completed; Makower D, Rozenblit A, Kaufman H, Edelman M, Lane ME, Zwiebel J, Haynes H, Wadler S. Phase II clinical trial of intralesional administration of the oncolytic adenovirus ONYX-015 in patients with hepatobiliary tumors with correlative p53 studies. Clin Cancer Res. 2003 Feb; 9(2): 693-702.<br>Phase 2; CRC, PanCa; intra-arteria (IA); Completed; Reid T, Galanis E, Abbruzzese J, Sze D, Wein LM, Andrews J, Randlev B, Heise C, Uprichard M, Hatfield M, Rome L, Rubin J, Kirn D. Hepatic arterial infusion of a replication-selective oncolytic adenovirus (dl1520): phase II viral, immunologic, and clinical endpoints. Cancer Res. 2002 Nov 1; 62(21): 6070-9.<br>Phase 2; SCCHN; IT; Completed; Nemunaitis J, Khuri F, Ganly I, Arseneau J, Posner M, Vokes E, Kuhn J, McCarty T, Landers S, Blackburn A, Romel L, Randlev B, Kaye S, Kirn D. Phase II trial of intratumoral administration of ONYX-015, a replication-selective adenovirus, in patients with refractory head and neck cancer. J Clin Oncol. 2001 Jan 15; 19(2): 289-98.<br>Phase 2; SCCHN; IT; Completed; Khuri FR, Nemunaitis J, Ganly I, Arseneau J, Tannock IF, Romel L, Gore M, Ironside J, MacDougall RH, Heise C, Randlev B, Gillenwater AM, Bruso P, Kaye SB, Hong WK, Kirn DH. a controlled trial of intratumoral ONYX-015, a selectively-replicating adenovirus, in combination with cisplatin and 5-fluorouracil in patients with recurrent head and neck cancer. Nat Med. 2000 Aug; 6(8): 879-85.<br>Phase 2; CRC; IV; Completed; Reid TR, Freeman S, Post L, McCormick F, Sze DY. Effects of Onyx-015 among metastatic colorectal cancer patients that have failed prior treatment with 5-FU/leucovorin. Cancer Gene Ther. 2005 Aug; 12(8): 673-81. |
| CG7060 | PSA control | Adenovirus | Phase 1; Prostate cancer; IT; Completed; DeWeese TL, van der Poel H, Li S, Mikhak B, Drew R, Goemann M, Hamper U, DeJong R, Detorie N, Rodriguez R, Haulk T, DeMarzo AM, Piantadosi S, Yu DC, Chen Y, Henderson DR, Carducci MA, Nelson WG, Simons JW. A phase I trial of CV706, a replication-competent, PSA selective oncolytic adenovirus, for the treatment of locally recurrent prostate cancer following radiation therapy. Cancer Res. 2001 Oct 15; 61(20): 7464-72. |
| CG7870/CV787 | Rat probasin-E1A | Adenovirus | Phase 1/2; Prostate cancer; IV; Completed; Small EJ, Carducci MA, Burke JM, Rodriguez R, Fong L, van Ummersen L, Yu DC, Aimi J, Ando D, Working P, Kirn D, Wilding G. A phase I trial of intravenous CG7870, a replication-selective, prostate-specific antigen-targeted oncolytic adenovirus, for the treatment of hormone-refractory, metastatic prostate cancer. Mol Ther. 2006 Jul; 14(1): 107-17. Epub 2006 May 9. |
| CG7870/CV787 | hPSA-E1B, E3+ | Adenovirus | Phase 1/2; Prostate cancer; IV; Terminated 2005 |
| CG0070 | E2F-1, GM-CSF | Adenovirus | Phase 2/3; Bladder cancer; Intracavity; Not yet open; Ramesh N, Ge Y, Ennist DL, Zhu M, Mina M, Ganesh S, Reddy PS, Yu DC. CG0070, a conditionally replicating granulocyte macrophage colony-stimulating factor - armed oncolytic adenovirus for the treatment of bladder cancer. Clin Cancer Res. 2006 Jan 1; 12(1): 305-13. |
| Telomelysin | hTERT | Adenovirus | Phase 1; Solid tumors; IT; Completed; Nemunaitis J, Tong AW, Nemunaitis M, Senzer N, Phadke AP, Bedell C, Adams N, Zhang YA, Maples PB, Chen S, Pappen B, Burke J, Ichimaru D, Urata Y, Fujiwara T. A phase I study of telomerase-specific replication competent oncolytic adenovirus (telomelysin) for various solid tumors. Mol Ther. 2010 Feb; 18(2): 429-34. doi: 10.1038/mt.2009.262. Epub 2009 Nov 24. |
| Ad5-CD/TKrep | CD/TK | Adenovirus | Phase 1; Prostate cancer; IT; Completed; Freytag SO, Khil M, Stricker H, Peabody J, Menon M, DePeralta-Venturina M, Nafziger D, Pegg J, Paielli D, Brown S, Barton K, Lu M, Aguilar-Cordova E, Kirn JH. Phase I study of replication-competent adenovirus-mediated double suicide gene therapy for the treatment of locally recurrent prostate cancer. Cancer Res. 2002 Sep 1; 62(17): 4968-76.<br>Phase 1; Prostate cancer; IT; Completed; Freytag SO, Stricker H, Pegg J, Paielli D, Pradhan DG, Peabody J, DePeralta-Venturina M, Xia X, Brown S, Lu M, Kirn JH. Phase I study of replication-competent adenovirus-mediated double-suicide gene therapy in combination with conventional-dose three-dimensional conformal radiation therapy for the treatment of newly diagnosed, intermediate- to high-risk prostate cancer. Cancer Res. 2003 Nov 1; 63(21): 7497-506. |

TABLE 3-continued

Immunostimulatory agents

| Strain | Modification(s)/ Description | Virus | Clinical Trial; Indication; Route; Status; Reference |
|---|---|---|---|
| Ad5-D24-RGD | RGD, Delta-24 | Adenovirus | Phase 1; Ovarian cancer; IP; Completed; Kirnball KJ, Preuss MA, Barnes MN, Wang M, Siegal GP, Wan W, Kuo H, Saddekni S, Stockard CR, Grizzle WE, Harris RD, Aurigemma R, Curiel DT, Alvarez RD. A phase I study of a tropism-modified conditionally replicative adenovirus for recurrent malignant gynecologic diseases. Clin Cancer Res. 2010 Nov 1; 16(21): 5277-87. doi: 10.1158/1078-0432.CCR-10-0791. Epub 2010 Oct 26. Phase 1; Glioma; IT; Recruiting Phase 1/2; Glioma; IT; Recruiting |
| Ad5-SSTR/TK-RGD | SSTR, TK, RGD | Adenovirus | Phase 1; Ovarian cancer; IP; Active; Ramesh N, Ge Y, Ennist DL, Zhu M, Mina M, Ganesh S, Reddy PS, Yu DC. CG0070, a conditionally replicating granulocyte macrophage colony-stimulating factor - armed oncolytic adenovirus for the treatment of bladder cancer. Clin Cancer Res. 2006 Jan 1; 12(1): 305-13. |
| CGTG-102 | Ad5/3, GM-CSF | Adenovirus | Phase 1/2; Solid tumors; IT; Not open; Koski A, Kangasniemi L, Escutenaire S, Pesonen S, Cerullo V, Diaconu I, Nokisalmi P, Raki M, Rajecki M, Guse K, Ranki T, Oksanen M, Holm SL, Haavisto E, Karioja-Kallio A, Laasonen L, Partanen K, Ugolini M, Helminen A, Karli E, Hannuksela P, Pesonen S, Joensuu T, Kanerva A, Hemminki A. Treatment of cancer patients with a serotype 5/3 chimeric oncolytic adenovirus expressing GMCSF. Mol Ther. 2010 Oct; 18(10): 1874-84. doi: 10.1038/mt.2010.161. Epub 2010 Jul 27. |
| CGTG-102 | Delta-24 | Adenovirus | Phase 1; Solid tumors; IT/IV; Recruiting |
| INGN-007 (VRX-007) | wtE1a, ADP | Adenovirus | Phase 1; Solid tumors; IT; Not open; Lichtenstein DL, Spencer JF, Doronin K, Patra D, Meyer JM, Shashkova EV, Kuppuswamy M, Dhar D, Thomas MA, Tollefson AE, Zumstein LA, Wold WS, Toth K. An acute toxicology study with INGN 007, an oncolytic adenovirus vector, in mice and permissive Syrian hamsters; comparisons with wild-type Ad5 and a replication-defective adenovirus vector. Cancer Gene Ther. 2009 Aug; 16(8): 644-54. doi: 10.1038/cgt.2009.5. Epub 2009 Feb 6. |
| ColoAd1 | Ad3/11p | Adenovirus | Phase 1/2; CRC, HCC;; Not open; Kuhn I, Harden P, Bauzon M, Chartier C, Nye J, Thorne S, Reid T, Ni S, Lieber A, Fisher K, Seymour L, Rubanyi GM, Harkins RN, Hermiston TW. Directed evolution generates a novel oncolytic virus for the treatment of colon cancer. PLoS One. 2008 Jun 18; 3(6): e2409. doi: 10.1371/journal.pone.0002409. |
| CAVATAK | — | Coxsackie virus (CVA21) | Phase 1; Melanoma; IT; Completed Phase 2; Melanoma; IT; Recruiting Phase 1; SCCHN; IT; Terminated Phase 1; Solid tumors; IV; Recruiting |
| Talimogene laherparepvec (OncoVEX) | GM-CSF | Herpes simplex virus | Phase 1; Solid tumors; IT; Completed; Hu JC, Coffin RS, Davis CJ, Graham NJ, Groves N, Guest PJ, Harrington KJ, James ND, Love CA, McNeish I, Medley LC, Michael A, Nutting CM, Pandha HS, Shorrock CA, Simpson J, Steiner J, Steven NM, Wright D, Coombes RC. A phase I study of OncoVEXGM-CSF, a second-generation oncolytic herpes simplex virus expressing granulocyte macrophage colony-stimulating factor. Clin Cancer Res. 2006 Nov 15; 12(22): 6737-47. |
| Talimogene laherparepvec (OncoVEX) | ICP34.5(−) | Herpes simplex virus | Phase 2; Melanoma; IT; Completed; Kaufman HL, Kirn DW, DeRaffele G, Mitcham J, Coffin RS, Kirn-Schulze S. Local and distant immunity induced by intralesional vaccination with an oncolytic herpes virus encoding GM-CSF in patients with stage IIIc and IV melanoma. Ann Surg Oncol. 2010 Mar; 17(3): 718-30. doi: 10.1245/s10434-009-0809-6; Senzer NN, Kaufman HL, Amatruda T, Nemunaitis M, Reid T, Daniels G, Gonzalez R, Glaspy J, Whitman E, Harrington K, Goldsweig H, Marshall T, Love C, Coffin R, Nemunaitis JJ. Phase II clinical trial of a granulocyte-macrophage colony-stimulating factor-encoding, second-generation oncolytic herpesvirus in patients with unresectable metastatic melanoma. J Clin Oncol. 2009 Dec 1; 27(34): 5763-71. doi: 0.1200/JCO.2009.24.3675. Epub 2009 Nov 2. |
| Talimogene laherparepvec (OncoVEX) | ICP47(−) | Herpes simplex virus | Phase 3; Melanoma; IT; Active |
| Talimogene laherparepvec (OncoVEX) | Us11 ↑ | Herpes simplex virus | Phase 1/2; SCCHN; IT; Completed; Harrington KJ, Hingorani M, Tanay MA, Hickey J, Bhide SA, Clarke PM, Renouf LC, Thway K, Sibtain A, McNeish IA, Newbold KL, Goldsweig H, Coffin R, Nutting CM. Phase I/II study of oncolytic HSV GM-CSF in combination with radiotherapy and cisplatin in untreated stage III/IV squamous cell cancer of the head and neck. Clin Cancer Res. 2010 Aug 1; 16(15): 4005-15. doi: 10.1158/1078-0432.CCR-10-0196. |
| G207 | ICP34.5(−), ICP6(−) | Herpes simplex virus | Phase 1/2; Glioma; IT; Completed; Markert JM, Liechty PG, Wang W, Gaston S, Braz E, Karrasch M, Nabors LB, Markiewicz M, Lakeman AD, Palmer CA, Parker JN, Whitley RJ, Gillespie GY. Phase Ib trial of mutant herpes simplex virus G207 inoculated pre-and post-tumor resection for recurrent GBM. Mol Ther. 2009 Jan; 17(1): 199-207. doi: 10.1038/mt.2008.228. Epub 2008 Oct 28; Markert JM, Medlock MD, Rabkin SD, Gillespie GY, Todo T, Hunter WD, Palmer CA, Feigenbaum F, Tornatore C, Tufaro F, Martuza RL. Conditionally replicating herpes simplex virus mutant, G207 for the treatment of malignant glioma: results of a phase I trial. Gene Ther. 2000 May; 7(10): 867-74. |

TABLE 3-continued

Immunostimulatory agents

| Strain | Modification(s)/ Description | Virus | Clinical Trial; Indication; Route; Status; Reference |
|---|---|---|---|
| G207 | LacZ(+) | Herpes simplex virus | Phase 1; Glioma; IT; Completed |
| G47Delta | From G207, ICP47− | Herpes simplex virus | Phase 1; Glioma; IT; Recruiting; Todo T, Martuza RL, Rabkin SD, Johnson PA. Oncolytic herpes simplex virus vector with enhanced MHC class I presentation and tumor cell killing. Proc Natl Acad Sci USA. 2001 May 22; 98(11): 6396-401. Epub 2001 May 15. PubMed PMID: 11353831; PubMed Central PMCID: PMC33479. |
| HSV 1716 (Seprehvir) | ICP34.5(−) | Herpes simplex virus | Phase 1; Non-CNS solid tumors; IT; Recruiting<br>Phase 1; SCCHN; IT; Completed; Mace AT, Ganly I, Soutar DS, Brown SM. Potential for efficacy of the oncolytic Herpes simplex virus 1716 in patients with oral squamous cell carcinoma. Head Neck. 2008 Aug; 30(8): 1045-51. doi: 10.1002/hed.20840.<br>Phase 1; Glioma; IT; Completed; Harrow S, Papanastassiou V, Harland J, Mabbs R, Petty R, Fraser M, Hadley D, Patterson J, Brown SM, Rampling R. HSV1716 injection into the brain adjacent to tumor following surgical resection of high-grade glioma: safety data and long-term survival. Gene Ther. 2004 Nov; 11(22): 1648-58; Papanastassiou V, Rampling R, Fraser M, Petty R, Hadley D, Nicoll J, Harland J, Mabbs R, Brown M. The potential for efficacy of the modified (ICP 34.5(−)) herpes simplex virus HSV1716 following intra-tumoral injection into human malignant glioma: a proof of principle study. Gene Ther. 2002 Mar; 9(6): 398-406.<br>Phase 1; Melanoma; IT; MacKie RM, Stewart B, Brown SM. Intralesional injection of herpes simplex virus 1716 in metastatic melanoma. Lancet. 2001 Feb 17; 357(9255): 525-6.<br>Phase 1; Mesothelioma; IF; not active |
| HF10 | HSV-1 HF strain | Herpes simplex virus | Phase 1; Solid tumors; IT; Recruiting<br>Phase 1; Pancreatic cancer; IT; Completed; Nakao A, Kasuya H, Sahin TT, Nomura N, Kanzaki A, Misawa M, Shirota T, Yamada S, Fujii T, Sugimoto H, Shikano T, Nomoto S, Takeda S, Kodera Y, Nishiyama Y. A phase I dose-escalation clinical trial of intraoperative direct intratumoral injection of HF10 oncolytic virus in non-resectable patients with advanced pancreatic cancer. Cancer Gene Ther. 2011 Mar; 18(3): 167-75. doi: 10.1038/cgt.2010.65. Epub 2010 Nov 19.<br>Phase 1; Breast cancer; IT; Completed; Kimata H, Imai T, Kikumori T, Teshigahara O, Nagasaka T, Goshima F, Nishiyama Y, Nakao A. Pilot study of oncolytic viral therapy using mutant herpes simplex virus (HF10) against recurrent metastatic breast cancer. Ann Surg Oncol. 2006 Aug; 13(8): 1078-84. Epub 2006 Jul 24.<br>Phase 1; SCCHN; IT; Completed; Fujimoto Y, Mizuno T, Sugiura S, Goshima F, Kohno S, Nakashima T, Nishiyama Y. Intratumoral injection of herpes simplex virus HF10 in recurrent head and neck squamous cell carcinoma. Acta Otolaryngol. 2006 Oct; 126(10): 1115-7. |
| NV1020 | | Herpes simplex virus | Phase 1; CRC liver mets; IA; Completed; Fong Y, Kim T, Bhargava A, Schwartz L, Brown K, Brody L, Covey A, Karrasch M, Getrajdman G, Meschecher A, Jarnagin W, Kemeny N. A herpes oncolytic virus can be delivered via the vasculature to produce biologic changes in human colorectal cancer. Mol Ther. 2009 Feb; 17(2): 389-94. doi: 10.1038/mt.2008.240. Epub 2008 Nov 18. |
| MV-CEA | CEA | Measles virus (Edmonston) | Phase 1; Ovarian cancer; IP; Completed; Galanis E, Hartmann LC, Cliby WA, Long HJ, Peethambaram PP, Barrette BA, Kaur JS, Haluska PJ Jr, Aderca I, Zollman PJ, Sloan JA, Keeney G, Atherton PJ, Podratz KC, Dowdy SC, Stanhope CR, Wilson TO, Federspiel MJ, Peng KW, Russell SJ. Phase I trial of intraperitoneal administration of an oncolytic measles virus strain engineered to express carcinoembryonic antigen for recurrent ovarian cancer. Cancer Res. 2010 Feb 1; 70(3): 875-82. doi: 10.1158/0008-5472.CAN-09-2762. Epub 2010 Jan 26.<br>Phase 1; Glioma; IT; Recruiting |
| MV-NIS | NIS | Measles virus (Edmonston) | Phase 1; Myeloma; IV; Recruiting<br>Phase 1; Ovarian cancer; IP; Recruiting<br>Phase 1; Mesothelioma; IP; Recruiting<br>Phase 1; SCCHN; IT; Not open |
| NDV-HUJ | — | Newcastle disease virus | Phase 1/2; Glioma; IV; Completed; Freeman AI, Zakay-Rones Z, Gomori JM, Linetsky E, Rasooly L, Greenbaum E, Rozenman-Yair S, Panet A, Libson E, Irving CS, Galun E, Siegal T. Phase I/II trial of intravenous NDV-HUJ oncolytic virus in recurrent glioblastoma multiforme. Mol Ther. 2006 Jan; 13(1): 221-8. Epub 2005 Oct 28; Pecora AL, Rizvi N, Cohen GI, Meropol NJ, Sterman D, Marshall JL, Goldberg S, Gross P, O'Neil JD, Groene WS, Roberts MS, Rabin H, Bamat MK, Lorence RM. Phase I trial of intravenous administration of PV701, an oncolytic virus, in patients with advanced solid cancers. J Clin Oncol. 2002 May 1; 20(9): 2251-66. |
| PV701 | — | Newcastle disease virus | Phase 1; Solid tumors; IV; Completed; Laurie SA, Bell JC, Atkins HL, Roach J, Bamat MK, O'Neil JD, Roberts MS, Groene WS, Lorence RM. A phase 1 clinical study of intravenous administration of PV701, an oncolytic virus, using two-step desensitization. Clin Cancer Res. 2006 Apr 15; 12(8): 2555-62. |

TABLE 3-continued

Immunostimulatory agents

| Strain | Modification(s)/ Description | Virus | Clinical Trial; Indication; Route; Status; Reference |
|---|---|---|---|
| MTH-68/H | — | Newcastle disease virus | Phase 2; Solid tumors; Inhalation; Completed; Csatary LK, Eckhardt S, Bukosza I, Czegledi F, Fenyvesi C, Gergely P, Bodey B, Csatary CM. Attenuated veterinary virus vaccine for the treatment of cancer. Cancer Detect Prev. 1993; 17(6): 619-27. |
| H-1PV | — | Parvovirus | Phase 1/2; Glioma; IT/IV; Recruiting; Geletneky K, Kiprianova I, Ayache A, Koch R, Herrero Y Calle M, Deleu L, Sommer C, Thomas N, Rommelaere J, Schlehofer JR. Regression of advanced rat and human gliomas by local or systemic treatment with oncolytic parvovirus H-1 in rat models. Neuro Oncol. 2010 Aug; 12(8): 804-14. doi: 10.1093/neuonc/noq023. Epub 2010 Mar 18. |
| PVS-RIPO | IRES | Poliovirus (Sabin) | Phase 1; Glioma; IT; Recruiting; Goetz C, Gromeier M. Preparing an oncolytic poliovirus recombinant for clinical application against glioblastoma multiforme. Cytokine Growth Factor Rev. 2010 Apr-Jun; 21(2-3): 197-203. doi: 10.1016/j.cytogfr.2010.02.005. Epub 2010 Mar 17. Review. |
| Reolysin | — | Reovirus (Dearing) | Phase 1/2; Glioma; IT; Completed; Forsyth P, Roldán G, George D, Wallace C, Palmer CA, Morris D, Cairncross G, Matthews MV, Markert J, Gillespie Y, Coffey M, Thompson B, Hamilton M. A phase I trial of intratumoral administration of reovirus in patients with histologically confirmed recurrent malignant gliomas. Mol Ther. 2008 Mar; 16(3): 627-32. doi: 10.1038/sj.mt.6300403. Epub 2008 Feb 5.<br>Phase 1; Peritoneal cancer; IF; Recruiting<br>Phase 1; Solid tumors; IV; Completed; Vidal L, Pandha HS, Yap TA, White CL, Twigger K, Vile RG, Melcher A, Coffey M, Harrington KJ, DeBono JS. A phase I study of intravenous oncolytic reovirus type 3 Dearing in patients with advanced cancer. Clin Cancer Res. 2008 Nov 1; 14(21): 7127-37. doi: 10.1158/1078-0432.CCR-08-0524.<br>Phase 1; Solid tumors; IV; Recruiting<br>Phase 1; CRC; IV; Recruiting<br>Phase 2; Sarcoma; IV; Completed<br>Phase 2; Melanoma; IV; Suspended<br>Phase 2; Ovarian, peritoneal cancer; IV; Recruiting<br>Phase 2; Pancreatic cancer; IV; Recruiting<br>Phase 2; SCCHN; IV; Not recruiting<br>Phase 2; Melanoma; IV; Recruiting<br>Phase 2; Pancreatic cancer; IV; Recruiting<br>Phase 2; Lung cancer; IV; Recruiting<br>Phase 3; SCCHN; IV; Recruiting |
| NTX-010 | | Seneca Valley virus | Phase 2; Small cell lung cancer; IV; Recruiting; PMID: 17971529 |
| Toca 511 | CD | Retrovirus | Phase 1/2; Glioma; IT; Recruiting; Tai CK, Wang WJ, Chen TC, Kasahara N. Single-shot, multicycle suicide gene therapy by replication-competent retrovirus vectors achieves long-term survival benefit in experimental glioma. Mol Ther. 2005 Nov; 12(5): 842-51. |
| JX-594 | GM-CSF | Vaccinia (Wyeth strain) | Phase 1; CRC; IV; Recruiting |
| JX-594 | TK(−) | Vaccinia (Wyeth strain) | Phase 1; Solid tumors; IV; Completed<br>Phase 1; HCC; IT; Completed; Park BH, Hwang T, Liu TC, Sze DY, Kim JS, Kwon HC, Oh SY, Han SY, Yoon JH, Hong SH, Moon A, Speth K, Park C, Ahn YJ, Daneshmand M, Rhee BG, Pinedo HM, Bell JC, Kim DH. Use of a targeted oncolytic poxvirus, JX-594, in patients with refractory primary or metastatic liver cancer: a phase I trial. Lancet Oncol. 2008 Jun; 9(6): 533-42. doi: 10.1016/S1470-2045(08)70107-4. Epub 2008 May 19. Erratum in: Lancet Oncol. 2008 Jul; 9(7): 613.<br>Phase 1; Pediatric solid tumors; IT; Recruiting<br>Phase 1; Melanoma; IT; Completed; Hwang TH, Moon A, Burke J, Ribas A, Stephenson J, Breitbach CJ, Daneshmand M, De Silva N, Parato K, Diallo JS, Lee YS, Liu TC, Bell JC, Kim DH. A mechanistic proof-of-concept clinical trial with JX-594, a targeted multi-mechanistic oncolytic poxvirus, in patients with metastatic melanoma. Mol Ther. 2011 Oct; 19(10): 1913-22. doi: 10.1038/mt.2011.132. Epub 2011 Jul 19.<br>Phase 1/2; Melanoma; IT; Completed; Mastrangelo MJ, Maguire HC Jr, Eisenlohr LC, Laughlin CE, Monken CE, McCue PA, Kovatich AJ, Lattime EC. Intratumoral recombinant GM-CSF-encoding virus as gene therapy in patients with cutaneous melanoma. Cancer Gene Ther. 1999 Sep-Oct; 6(5): 409-22.<br>Phase 2; HCC; IT; Not recruiting, analyzing data<br>Phase 2B; HCC; IV; Recruiting<br>Phase 1/2; CRC; IV/IT; Recruiting<br>Phase 2; CRC; IT; Not yet recruiting |
| vvDD-CDSR | TK−, VGF−, LacZ, CD, Somatostatin R | Vaccinia (Western Reserve) | Phase 1; Solid tumors; IT/IV; Recruiting; McCart JA, Mehta N, Scollard D, Reilly RM, Carrasquillo JA, Tang N, Deng H, Miller M, Xu H, Libutti SK, Alexander HR, Bartlett DL. Oncolytic vaccinia virus expressing the human somatostatin receptor SSTR2: molecular imaging after systemic delivery using 111In-pentetreotide. Mol Ther. 2004 Sep; 10(3): 553-61. |
| GL-ONC1 | Renilla luciferase | Vaccinia | Phase 1; Solid tumors; IV; Recruiting; Gentschev I, Müller M, Adelfinger M, Weibel S, Grummt F, Zimmermann M, Bitzer M, Heisig M, Zhang Q, Yu YA, |

TABLE 3-continued

Immunostimulatory agents

| Strain | Modification(s)/ Description | Virus | Clinical Trial; Indication; Route; Status; Reference |
|---|---|---|---|
| | | | Chen NG, Stritzker J, Lauer UM, Szalay AA. Efficient colonization and therapy of human hepatocellular carcinoma (HCC) using the oncolytic vaccinia virus strain GLV-1h68. PLoS One. 2011; 6(7): e22069. doi: 10.1371/journal.pone.0022069. Epub 2011 Jul 11. |
| (GLV-h68) | GFP, β-gal | Vaccinia | Phase 1/2; Peritoneal carcinomatosis; IP; Recruiting |
| Lister | β-glucoronidase | Vaccinia | Phase 1/2; SCCHN; IV; Recruiting |
| VSV-hIFNβ | IFN-β | Vesicular stomatitis virus (Indiana) | Phase 1; HCC; IT; Recruiting |
| DNX-2401 | DNAtrix | Adenovirus | See, e.g., *Molecular Therapy* 21(10): 1814-1818, 2013 and *Journal of Vascular and Interventional Radiology* 24(8): 1115-1122, 2013 |
| Toca511 | Tocagen | Lentivirus | See, e.g., *Molecular Therapy* 21(10): 1814-1818, 2013 and *Journal of Vascular and Interventional Radiology* 24(8): 1115-1122, 2013 |
| HSV T-VEC | | HSV | See, e.g., *Molecular Therapy* 21(10): 1814-1818, 2013 and *Journal of Vascular and Interventional Radiology* 24(8): 1115-1122, 2013 |
| H-1 ParvOryx | | Parvovirus | See, e.g., *Molecular Therapy* 21(10): 1814-1818, 2013 and *Journal of Vascular and Interventional Radiology* 24(8): 1115-1122, 2013 |
| VACV-TRAIL | (see work of Karolina Autio and Suvi Parvainen, Helsinki) | Vaccinia virus | See, e.g., *Molecular Therapy* 21(10): 1814-1818, 2013 and *Journal of Vascular and Interventional Radiology* 24(8): 1115-1122, 2013 |
| VACV-CD40L | (see work of Karolina Autio and Suvi Parvainen, Helsinki) | Vaccinia virus | See, e.g., *Molecular Therapy* 21(10): 1814-1818, 2013 and *Journal of Vascular and Interventional Radiology* 24(8): 1115-1122, 2013 |
| Maraba | (see work of Dave Stojdl, and John Bell) | Rhabdovirus | Preclinical/Clinical Candidate |
| Maraba-MG1 | (see work of Dave Stojdl, and John Bell) | Rhabdovirus | |
| Maraba MG1-hMAGE-A3 | (see work of Dave Stojdl, Brian Litchy and John Bell) | Rhabdovirus | Preclinical/Clinical Candidate |
| | | Sindbis virus | Preclinical/Clinical Candidate |
| | | Coxsackievirus A21 | Preclinical/Clinical Candidate |
| MYXV | | Poxvirus | Preclinical/Clinical Candidate Chan WM, Rahman MM, McFadden G. Oncolytic myxoma virus: the path to clinic. Vaccine. 2013 Sep 6; 31(39): 4252-8. doi: 10.1016/j.vaccine.2013.05.056. Epub 2013 May 29. |
| WT VSV ('Rose lab') | The parental rWT VSV for most VSV-based OVs. The L gene and the N-terminal 49 residues of the N gene are derived from the Mudd-Summers strain, the rest is from the San Juan strain (both Indiana serotype) | | Recombinant VSV used as oncolytic agent against cancer(see, e.g., see, e.g., *J Gen Virol* 93(12): 2529-2545, 2012; Lawson ND, Stillman EA, Whitt MA, Rose JK. Recombinant vesicular stomatitis viruses from DNA. Proc Natl Acad Sci USA. 1995 May 9; 92(10): 4477-81. Erratum in: Proc Natl Acad Sci USA 1995 Sep 12; 92(19): 9009.) |
| VSV-WT-XN2 (or XN1) | Derivative of rWT VSV ('Rose lab'). Generated using pVSV-XN2 (or pVSV-XN1), a full-length VSV plasmid containing uniqueXhoI and NheI sites flanked by VSV transcription start and stop signals between G and L genes. pVSV-XN2 (or pVSV-XN1) is commonly used to generate recombinant VSVs encoding an extra gene | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10.; Schnell MJ, Buonocore L, Kretzschmar E, Johnson E, Rose JK. Foreign glycoproteins expressed from recombinant vesicular stomatitis viruses are incorporated efficiently into virus particles. Proc Natl Acad Sci USA. 1996 Oct 15; 93(21): 11359-65.) |
| WT VSV ('Wertz lab') | Alternative rWT VSV. The N, P, M and L genes originate from the San Juan strain; G gene from the Orsay strain (both Indiana serotype). Rarely used in OV studies | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Whelan SP, Ball LA, Barr JN, Wertz GT. Efficient recovery of infectious vesicular stomatitis virus entirely from cDNA clones. Proc Natl Acad Sci USA. 1995 Aug 29; 92(18): 8388-92.) |
| VSV-WT-GFP, -RFP, -Luc, -LacZ | WT VSV encoding reporter genes (between G and L) to track virus infection. Based on pVSV-XN2. Toxicity similar to VSV-WT | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Fernadez et al., "Genetically Engineered Vesicular Stomatitis Virus in Gene Therapy: Application for Treatment of Malignant Disease", J Virol 76: 895-904 (2002); Lan Wu, Tian-gui Huang, Marcia Meseck, Jennifer Altomonte, Oliver Ebert, Katsunori Shinozaki, Adolfo Garcia-Sastre, John Fallon, John Mandeli, and Savio L. C. Woo. Human Gene Therapy. June 2008, 19(6): 635-647) |
| VSV-G/GFP | GFP sequence fused to VSV G gene is inserted between the WT G and L genes (in addition to WT G). Toxicity similar to that of VSV-WT | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Dalton, K. P. & Rose, J. K. (2001). Vesicular stomatitis virus glycoprotein containing the entire green fluorescent protein on its cytoplasmic domain is incorporated efficiently into virus particles. Virology 279, 414-421.) |

TABLE 3-continued

Immunostimulatory agents

| Strain | Modification(s)/ Description | Virus | Clinical Trial; Indication; Route; Status; Reference |
|---|---|---|---|
| VSV-rp30 | Derivative of VSV-G/GFP. Generated by positive selection on glioblastoma cells and contains two silent mutations and two missense mutations, one in P and one in L. 'rp30' indicates 30 repeated passages | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Wollmann, G., Tattersall, P. & van den Pol, A. N. (2005). Targeting human glioblastoma cells: comparison of nine viruses with oncolytic potential. J Virol 79, 6005-6022.) |
| VSV-p1-GFP, VSV-p1-RFP | VSV expressing GFP or red fluorescent protein (RFP or dsRed) reporter gene at position 1. Attenuated because all VSV genes are moved downward, to positions 2-6. Safe and still effective as an OV | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Wollmann, G., Rogulin, V., Simon, I., Rose, J. K. & van den Pol, A. N. (2010). Some attenuated variants of vesicular stomatitis virus show enhanced oncolytic activity against human glioblastoma cells relative to normal brain cells. J Virol 84, 1563-1573.) |
| VSV-dG-GFP (or RFP) (replication-defective) | Similar to VSV-p1-GFP or VSV-p1-RFP described above, but with the G gene deleted. Cannot generate a second round of infection. Poor ability to kill tumor cells | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Wollmann, G., Rogulin, V., Simon, I., Rose, J. K. & van den Pol, A. N. (2010). Some attenuated variants of vesicular stomatitis virus show enhanced oncolytic activity against human glioblastoma cells relative to normal brain cells. J Virol 84, 1563-1573.) |
| VSV-ΔP, -ΔL, -ΔG (semi-replication-competent) | Each virus cannot replicate alone because of one VSV gene deleted, but when viruses co-infect, they show good replication, safety and oncolysis (especially the combination of VSVΔG/VSVΔL). VSVΔP and VSVΔL contain dsRed in place of the corresponding viral gene. VSVΔG contains GFP gene in place of G | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Muik, A., Dold, C., Geiβ, Y., Volk, A., Werbizki, M., Dietrich, U. & von Laer, D. (2012). Semireplication-competent vesicular stomatitis virus as a novel platform for oncolytic virotherapy. J Mol Med (Berl) 90, 959-970.) |
| VSV-M51R | M mutant; the M51R mutation was introduced into M | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Kopecky, S. A., Willingham, M. C. & Lyles, D. S. (2001). Matrix protein and another viral component contribute to induction of apoptosis in cells infected with vesicular stomatitis virus. J Virol 75, 12169-12181.) |
| VSV-ΔM51, VSV-ΔM51-GFP, -RFP, -FLuc, -Luc, -LacZ | M mutant; the ΔM51 mutation was introduced into M. In addition, some recombinants encode a reporter gene between the G and L | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Stojdl, D. F., Lichty, B. D., tenOever, B. R., Paterson, J. M., Power, A. T., Knowles, S., Marius, R., Reynard, J., Poliquin, L. & other authors (2003). VSV strains with defects in their ability to shutdown innate immunity are potent systemic anti-cancer agents. Cancer Cell 4, 263-275.; Power, A. T. & Bell, J. C. (2007). Cell-based delivery of oncolytic viruses: a new strategic alliance for a biological strike against cancer. Mol Ther 15, 660-665.; Wu, L., Huang, T. G., Meseck, M., Altomonte, J., Ebert, O., Shinozaki, K., Garci'a-Sastre, A., Fallon, J., Mandeli, J. & Woo, S. L. (2008). rVSV(MD51)-M3 is an effective and safe oncolytic virus for cancer therapy. Hum Gene Ther 19, 635-647.) |
| VSV-*Mmut | M mutant; VSV with a single mutation or combination of mutations at the following M positions: M33A, M51R, V221F and S226R | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Hoffmann, M., Wu, Y. J., Gerber, M., Berger-Rentsch, M., Heimrich, B., Schwemmle, M. & Zimmer, G. (2010). Fusion-active glycoprotein G mediates the cytotoxicity of vesicular stomatitis virus M mutants lacking host shut-off activity. J Gen Virol 91, 2782-2793.) |
| VSV-M6PY >A4-R34E and other M mutants | M mutant; the M51R mutation was introduced into the M gene, and, in addition, the mutations in the PSAP motif (residues 37-40) of M | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Irie, T., Carnero, E., Okumura, A., Garci'a-Sastre, A. & Harty, R. N. (2007). Modifications of the PSAP region of the matrix protein lead to attenuation of vesicular stomatitis virus in vitro and in vivo. J Gen Virol 88, 2559-2567.) |
| VSV-M(mut) | M mutant; VSV M residues 52-54 are mutated from DTY to AAA. M(mut) cannot block nuclear mRNA export | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Heiber, J. F. & Barber, G. N. (2011). Vesicular stomatitis virus expressing tumor suppressor p53 is a highly attenuated, potent oncolytic agent. J Virol 85, 10440-10450.) |
| VSV-G5, -G5R, -G6, -G6R | G mutant; VSV-expressing mutant G with amino acid substitutions at various | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: |

TABLE 3-continued

Immunostimulatory agents

| Strain | Modification(s)/ Description | Virus | Clinical Trial; Indication; Route; Status; Reference |
|---|---|---|---|
| | positions (between residues 100 and 471). Triggers type I IFN secretion as the M51R, but inhibits cellular transcription and host protein translation like WT | | 10.1099/vir.0.046672-0. Epub 2012 Oct 10; Janelle, V., Brassard, F., Lapierre, P., Lamarre, A. & Poliquin, L. (2011). Mutations in the glycoprotein of vesicular stomatitis virus affect cytopathogenicity: potential for oncolytic virotherapy. J Virol 85, 6513-6520.) |
| VSV-CT1 | G mutant; the cytoplasmic tail of the G protein was truncated from 29 to 1 aa. Decreased neuropathology, but marginal oncolytic efficacy | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Ozduman, K., Wollmann, G., Ahmadi, S. A. & van den Pol A. N. (2009). Peripheral immunization blocks lethal actions of vesicular stomatitis virus within the brain. J Virol 83, 11540-11549.; Wollmann, G., Rogulin, V., Simon, I., Rose, J. K. & van den Pol, A. N. (2010). Some attenuated variants of vesicular stomatitis virus show enhanced oncolytic activity against human glioblastoma cells relative to normal brain cells. J Virol 84, 1563-1573.) |
| VSV-CT9-M51 | G mutant; the cytoplasmic tail of VSV-G was reduced from 29 to 9 aa, also has ΔM51 mutation. Attenuated neurotoxicity and good OV abilities | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Ozduman, K., Wollmann, G., Ahmadi, S. A. & van den Pol, A. N. (2009). Peripheral immunization blocks lethal actions of vesicular stomatitis virus within the brain. J Virol 83, 11540-11549.; Wollmann, G., Rogulin, V., Simon, I., Rose, J. K. & van den Pol, A. N. (2010). Some attenuated variants of vesicular stomatitis virus show enhanced oncolytic activity against human glioblastoma cells relative to normal brain cells. J Virol 84, 1563-1573.) |
| VSV-DV/F(L289A) (same as rVSV-F) | Foreign glycoprotein; VSV expressing the NDV fusion protein gene between G and L. The L289A mutation in this protein allows it to induce syncytia alone (without NDV HN protein) | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Ebert, O., Shinozaki, K., Kournioti, C., Park, M. S., Garci'a-Sastre, A. & Woo, S. L. (2004). Syncytia induction enhances the oncolytic potential of vesicular stomatitis virus in virotherapy for cancer. Cancer Res 64, 3265-3270.) |
| VSV-S-GP | Foreign glycoprotein; VSV with the native G gene deleted and replaced with a modified glycoprotein protein (GP) from Sindbis virus (SV). Also expressing mouse GM-CSF and GFP (between SV GP and VSV L). The modified GP protein recognizes the Her2 receptor, which is overexpressed on many breast cancer cells | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Bergman, I., Griffin, J. A., Gao, Y. & Whitaker-Dowling, P. (2007). Treatment of implanted mammary tumors with recombinant vesicular stomatitis virus targeted to Her2/neu. Int J Cancer 121, 425-430.) |
| VSV-ΔG-SV5-F | Foreign glycoprotein; VSV G gene is replaced with the fusogenic simian parainfluenza virus 5 fusion protein (SV5-F) gene | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Chang, G., Xu, S., Watanabe, M., Jayakar, H. R., Whitt, M. A. & Gingrich, J. R. (2010). Enhanced oncolytic activity of vesicular stomatitis virus encoding SV5-F protein against prostate cancer. J Urol 183, 1611-1618.) |
| VSV-FAST, VSV-(ΔM51)-FAST | Foreign glycoprotein; VSV or VSV-MΔ51 expressing the p14 FAST protein of reptilian reovirus (between VSV G and L) | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Brown, C. W., Stephenson, K. B., Hanson, S., Kucharczyk, M., Duncan, R., Bell, J. C. & Lichty, B. D. (2009). The p14 FAST protein of reptilian reovirus increases vesicular stomatitis virus neuropathogenesis. J Virol 83, 552-561.) |
| VSV-LCMV-GP (replication-defective) | Foreign glycoprotein; VSV lacking the G gene was pseudotyped with the non-neurotropic glycoprotein of LMCV | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Muik, A., Kneiske, I., Werbizki, M., Wilflingseder, D., Giroglou, T., Ebert, O., Kraft, A., Dietrich, U., Zimmer, G. & other authors (2011). Pseudotyping vesicular stomatitis virus with lymphocytic choriomeningitis virus glycoproteins enhances infectivity for glioma cells and minimizes neurotropism. J Virol 85, 5679-5684.) |
| VSV-H/F, -αEGFR, -αFR, -αPSMA (replication-defective) | Foreign glycoprotein; VSV lacking the G gene was pseudotyped with the MV F and H displaying single-chain antibodies (scFv) specific for epidermal growth factor receptor, folate receptor, or prostate membrane-specific antigen. Retargeted VSV to | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Ayala-Breton, C., Barber, G. N., Russell, S. J. & Peng, K. W. (2012). Retargeting vesicular stomatitis virus using measles virus envelope glycoproteins. Hum Gene Ther 23, 484-491.) |

TABLE 3-continued

Immunostimulatory agents

| Strain | Modification(s)/ Description | Virus | Clinical Trial; Indication; Route; Status; Reference |
|---|---|---|---|
| VSV-let-7wt | cells that expressed the targeted receptor microRNA target; the let-7 microRNA targets are inserted into the 3'-UTR of VSV M | | Recombinant VSV used as oncolytic agent against cancer (see, e.g., Hastie E, Grdzelishvili VZ. Vesicular stomatitis virus as a flexible platform for oncolytic vir TABLE 3-continued Immunostimulatory agents

| Strain | Modification(s)/ Description | Virus | Clinical Trial; Indication; Route; Status; Reference |
|---|---|---|---|
| | | | expression enhances vesicular stomatitis virus oncolytic therapy in murine squamous cell carcinoma. Laryngoscope 117, 210-214.) |
| VSV-IL23 | Immunomodulation; VSV expressing IL-23. Significantly attenuated in the CNS, but effective OV | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Miller, J. M., Bidula, S. M., Jensen, T. M. & Reiss, C. S. (2010). Vesicular stomatitis virus modified with single chain IL-23 exhibits oncolytic activity against tumor cells in vitro and in vivo. Int J Infereron Cytokine Mediator Res 2010, 63-72.) |
| VSV-IL28 | Immunomodulation; VSV expressing IL-28, a member of the type III IFN (IFN-λ) family | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Wongthida, P., Diaz, R. M., Galivo, F., Kottke, T., Thompson, J., Pulido, J., Pavelko, K., Pease, L., Melcher, A. & Vile, R. (2010). Type III IFN interleukin-28 mediates the antitumor efficacy of oncolytic virus VSV in immune-competent mouse models of cancer. Cancer Res 70, 4539-4549.) |
| VSV-opt.hIL-15 | Immunomodulation; VSV-MΔ51 expressing a highly secreted version of human IL-15 | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Stephenson, K. B., Barra, N. G., Davies, E., Ashkar, A. A. & Lichty, B. D. (2012). Expressing human interleukin-15 from oncolytic vesicular stomatitis virus improves survival in a murine metastatic colon adenocarcinoma model through the enhancement of antitumor immunity. Cancer Gene Ther 19, 238-246.) |
| VSV-CD40L | Immunomodulation; VSV expressing CD40L, a member of the tumor necrosis factor (TNF) family of cell-surface molecules | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Galivo, F., Diaz, R. M., Thanarajasingam, U., Jevremovic, D., Wongthida, P., Thompson, J., Kottke, T., Barber, G. N., Melcher, A. & Vile, R. G. (2010). Interference of CD40L-mediated tumor immunotherapy by oncolytic vesicular stomatitis virus. Hum Gene Ther 21, 439-450.) |
| VSV-Flt3L | Immunomodulation; VSV-MΔ51 expressing the soluble form of the human Flt3L, a growth factor activating DCs | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Leveille, S., Goulet, M. L., Lichty, B. D. & Hiscott, J. (2011). Vesicular stomatitis virus oncolytic treatment interferes with tumor-associated dendritic cell functions and abrogates tumor antigen presentation. J Virol 85, 12160-12169.) |
| VSV/hDCT | Immunomodulation; VSV-MΔ51 expressing hDCT | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Boudreau, J. E., Bridle, B. W., Stephenson, K. B., Jenkins, K. M., Brunellie're, J., Bramson, J. L., Lichty, B. D. & Wan, Y. (2009). Recombinant vesicular stomatitis virus transduction of dendritic cells enhances their ability to prime innate and adaptive antitumor immunity. Mol Ther 17, 1465-1472.) |
| VSV-hgp100 | Immunomodulation; VSV expressing hgp100, an altered self-TAA against which tolerance is well-established in C57BL/6 mice | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Wongthida, P., Diaz, R. M., Galivo, F., Kottke, T., Thompson, J., Melcher, A. & Vile, R. (2011). VSV oncolytic virotherapy in the B16 model depends upon intact MyD88 signaling. Mol Ther 19, 150-158.) |
| VSV-ova | Immunomodulation; VSV expressing chicken ovalbumin (for B16ova cancer model) | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Diaz, R. M., Galivo, F., Kottke, T., Wongthida, P., Qiao, J., Thompson, J., Valdes, M., Barber, G. & Vile, R. G. (2007). Oncolytic immunovirotherapy for melanoma using vesicular stomatitis virus. Cancer Res 67, 2840-2848.) |
| VSV-gG | Immunomodulation; VSV expressing EHV-1 glycoprotein G, a broad-spectrum viral chemokine-binding protein | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Altomonte, J., Wu, L., Chen, L., Meseck, M., Ebert, O., Garci'a-Sastre, A., Fallon, J. & Woo, S. L. (2008). Exponential enhancement of oncolytic vesicular stomatitis virus potency by vector-mediated suppression of inflammatory responses in vivo. Mol Ther 16, 146-153.) |
| VSV-UL141 | Immunomodulation; VSV expressing a secreted form of the human cytomegalovirus UL141 protein, known to inhibit the function of NK cells by | | Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Altomonte, J., Wu, L., Meseck, M., Chen, L., Ebert, O., Garcia-Sastre, A., Fallon, J., Mandeli, J. & Woo, S. L. |

TABLE 3-continued

Immunostimulatory agents

| Strain | Modification(s)/Description | Virus | Clinical Trial; Indication; Route; Status; Reference |
|---|---|---|---|
| VSV-(Δ51)-M3 | blocking the ligand of NK cell-activating receptors Immunomodulation; VSV-MΔ51 expressing the murine gammaherpesvirus-68 chemokine-binding protein M3 | | (2009). Enhanced oncolytic potency of vesicular stomatitis virus through vector-mediated inhibition of NK and NKT cells. Cancer Gene Ther 16, 266-278.) Recombinant VSV used as oncolytic agent against cancer (see, e.g., Hastie E, Grdzelishvili VZ. Vesicular stomatitis virus as a flexible platform for oncolytic virotherapy against cancer. J Gen Virol. 2012 Dec; 93(Pt 12): 2529-45. doi: 10.1099/vir.0.046672-0. Epub 2012 Oct 10; Wu, L., Huang, T. G., Meseck, M., Altomonte, J., Ebert, O., Shinozaki, K., Garci'a-Sastre, A., Fallon, J., Mandeli, J. & Woo, S. L. (2008). rVSV(MD51)-M3 is an effective and safe oncolytic virus for cancer therapy. Hum Gene Ther 19, 635-647.) |
| HSV-1 | Genome and Structure: ds DNA; Enveloped Representative Host: Human | Herpesviridae | Clinical phase I/II; Glioma; Wollmann et al. Oncolytic virus therapy for glioblastoma multiforme: concepts and candidates. *Cancer J.* 2012 Jan-Feb; 18(1): 69-81 |
| NDV | Genome and Structure: ss (−) RNA; Enveloped Representative Host: Avian | Paramyxoviridae | Clinical phase I/II; Glioma; Wollmann et al. Oncolytic virus therapy for glioblastoma multiforme: concepts and candidates. *Cancer J.* 2012 Jan-Feb; 18(1): 69-81 |
| Adeno | Genome and Structure: ds DNA; Naked Representative Host: Human | Adenoviridae | Clinical phase I; Glioma; Wollmann et al. Oncolytic virus therapy for glioblastoma multiforme: concepts and candidates. *Cancer J.* 2012 Jan-Feb; 18(1): 69-81 |
| Reo | Genome and Structure: ds RNA; Naked Representative Host: Mammalian | Reoviridae | Clinical phase I; Glioma; Wollmann et al. Oncolytic virus therapy for glioblastoma multiforme: concepts and candidates. *Cancer J.* 2012 Jan-Feb; 18(1): 69-81 |
| Vaccinia | Genome and Structure: ds DNA; Enveloped Representative Host: Cow/horse, others | Poxviridae | Preclinical in vivo; Glioma; Wollmann et al. Oncolytic virus therapy for glioblastoma multiforme: concepts and candidates. *Cancer J.* 2012 Jan-Feb; 18(1): 69-81 |
| Polio | Genome and Structure: ss (+) RNA; Naked Representative Host: Human | Picornaviridae | Clinical phase I; Glioma; Wollmann et al. Oncolytic virus therapy for glioblastoma multiforme: concepts and candidates. *Cancer J.* 2012 Jan-Feb; 18(1): 69-81 |
| VSV | Genome and Structure: ss (−) RNA; Enveloped Representative Host: Livestock/mosquito | Rhabdoviridae | Preclinical in vivo; Glioma; Wollmann et al. Oncolytic virus therapy for glioblastoma multiforme: concepts and candidates. *Cancer J.* 2012 Jan-Feb; 18(1): 69-81 |
| MVM | Genome and Structure: ss DNA; Naked Representative Host: Mouse | Parvoviridae | Preclinical in vitro; Glioma; Wollmann et al. Oncolytic virus therapy for glioblastoma multiforme: concepts and candidates. *Cancer J.* 2012 Jan-Feb; 18(1): 69-81 |
| Sindbis | Genome and Structure: ss (+) RNA; Enveloped Representative Host: Mammalian/mosquito | Togaviridae | Preclinical in vitro; Glioma; Wollmann et al. Oncolytic virus therapy for glioblastoma multiforme: concepts and candidates. *Cancer J.* 2012 Jan-Feb; 18(1): 69-81 |
| PRV | Genome and Structure: ds DNA; Enveloped Representative Host: Pig | Herpesviridae | Preclinical in vitro; Glioma; Wollmann et al. Oncolytic virus therapy for glioblastoma multiforme: concepts and candidates. *Cancer J.* 2012 Jan-Feb; 18(1): 69-81 |
| Measles | Genome and Structure: ss (−) RNA; Enveloped Representative Host: Human | Paramyxoviridae | Clinical phase I; Glioma; Wollmann et al. Oncolytic virus therapy for glioblastoma multiforme: concepts and candidates. *Cancer J.* 2012 Jan-Feb; 18(1): 69-81 |
| Myxoma | Genome and Structure: ds DNA; Enveloped Representative Host: Rabbit | Poxviridae | Preclinical in vivo; Glioma; Wollmann et al. Oncolytic virus therapy for glioblastoma multiforme: concepts and candidates. *Cancer J.* 2012 Jan-Feb; 18(1): 69-81 |
| H1PV | Genome and Structure: ss DNA; Naked Representative Host: Rat | Parvoviridae | Clinical phase I; Glioma; Wollmann et al. Oncolytic virus therapy for glioblastoma multiforme: concepts and candidates. *Cancer J.* 2012 Jan-Feb; 18(1): 69-81 |
| SVV | Genome and Structure: ss (+) RNA; Naked Representative Host: Pig | Picornaviridae | Preclinical in vitro; Glioma; Wollmann et al. Oncolytic virus therapy for glioblastoma multiforme: concepts and candidates. *Cancer J.* 2012 Jan-Feb; 18(1): 69-81 |
| HSV (G207)I | | | Phase I; Malignant glioma; IT injection; Wollmann et al. Oncolytic virus therapy for glioblastoma multiforme: concepts and candidates. *Cancer J.* 2012 Jan-Feb; 18(1): 69-81; Markert JM, Medlock MD, Rabkin SD, et al. Conditionally replicating herpes simplex virus mutant, G207 for the treatment of malignant glioma: results of a phase I trial. Gene Ther. 2000; 7: 867Y874. Phase I; Malignant glioma; IT injection; Wollmann et al. Oncolytic virus therapy for glioblastoma multiforme: concepts and candidates. *Cancer J.* 2012 Jan-Feb; 18(1): 69-81; Markert JM, Liechty PG, WangW, et al. Phase Ib trial of mutant herpes simplex virus G207 inoculated pre-and post-tumor resection for recurrent GBM. Mol Ther. 2009; 17: 199Y207. Phase I; Malignant glioma; IT injection; Wollmann et al. Oncolytic virus therapy for glioblastoma multiforme: concepts and candidates. *Cancer J.* 2012 Jan-Feb; 18(1): 69-81 |
| HSV (1716) | | | Phase II; Malignant glioma; IT injection; Wollmann et al. Oncolytic virus therapy for glioblastoma multiforme: concepts and candidates. *Cancer J.* 2012 Jan-Feb; 18(1): 69-81; Rampling R, Cruickshank G, Papanastassiou V. et al. Toxicity evaluation of replication-competent herpes simplex virus (ICP 34.5 null mutant 1716) in patients with recurrent malignant glioma. Gene Ther. 2000; 7: 859Y866. Phase I; Malignant glioma; IT injection; Wollmann et al. Oncolytic virus therapy for glioblastoma multiforme: concepts and candidates. *Cancer J.* 2012 Jan- |

TABLE 3-continued

Immunostimulatory agents

| Strain | Modification(s)/Description | Virus | Clinical Trial; Indication; Route; Status; Reference |
|---|---|---|---|
| | | | Feb; 18(1): 69-81; Papanastassiou V, Rampling R, Fraser M, et al. The potential for efficacy of the modified (ICP 34.5(j)) herpes simplex virus HSV1716 following intratumoral injection into human malignant glioma: a proof of principle study. Gene Ther. 2002; 9: 398Y406.<br>Phase I; Malignant glioma; IT injection; Wollmann et al. Oncolytic virus therapy for glioblastoma multiforme: concepts and candidates. *Cancer J.* 2012 Jan-Feb; 18(1): 69-81; Harrow S, Papanastassiou V, Harland J, et al. HSV1716 injection into the brain adjacent to tumor following surgical resection of high-grade glioma: safety data and long-term survival. Gene Ther. 2004; 11: 1648Y1658.<br>Phase II; Malignant glioma; Wollmann et al. Oncolytic virus therapy for glioblastoma multiforme: concepts and candidates. *Cancer J.* 2012 Jan-Feb; 18(1): 69-81 |
| HSV (G47Δ) | | | Phase I; Malignant glioma; Wollmann et al. Oncolytic virus therapy for glioblastoma multiforme: concepts and candidates. *Cancer J.* 2012 Jan-Feb; 18(1): 69-81 |
| HSV (M032) | | | Phase I; Malignant glioma; Wollmann et al. Oncolytic virus therapy for glioblastoma multiforme: concepts and candidates. *Cancer J.* 2012 Jan-Feb; 18(1): 69-81 |
| AdV (ONYX-015) | | | Phase I; Malignant glioma; injection to tumor resection cavity; Wollmann et al. Oncolytic virus therapy for glioblastoma multiforme: concepts and candidates. *Cancer J.* 2012 Jan-Feb; 18(1): 69-81; Chiocca EA, Abbed KM, Tatter S, et al. A phase I open-label, dose-escalation, multi-institutional trial of injection with an E1BAttenuated adenovirus, ONYX-015, into the peritumoral region of recurrent malignant gliomas, in the adjuvant setting. Mol Ther. 2004; 10: 958Y966. |
| AdV (Delta24-RGD) | | | Phase I; Malignant glioma; Wollmann et al. Oncolytic virus therapy for glioblastoma multiforme: concepts and candidates. *Cancer J.* 2012 Jan-Feb; 18(1): 69-81 |
| ReoV | | | Phase I; Malignant glioma; IT injection; Wollmann et al. Oncolytic virus therapy for glioblastoma multiforme: concepts and candidates. *Cancer J.* 2012 Jan-Feb; 18(1): 69-81; Forsyth P, Roldan G, George D, et al. A phase I trial of intratumoral administration of reovirus in patients with histologically confirmed recurrent malignant gliomas. Mol Ther. 2008; 16: 627Y632.<br>Phase I; Malignant glioma; Convection enhanced; Wollmann et al. Oncolytic virus therapy for glioblastoma multiforme: concepts and candidates. *Cancer J.* 2012 Jan-Feb; 18(1): 69-81 |
| NDV (HUJ) | | | Phase I/II; Malignant glioma; IV; Wollmann et al. Oncolytic virus therapy for glioblastoma multiforme: concepts and candidates. *Cancer J.* 2012 Jan-Feb; 18(1): 69-81; Freeman AI, Zakay-Rones Z, Gomori JM, et al. Phase I/II trial of intravenous NDV-HUJ oncolytic virus in recurrent glioblastoma multiforme. Mol Ther. 2006; 13: 221Y228.<br>Phase I/II; Malignant glioma; IV; Wollmann et al. Oncolytic virus therapy for glioblastoma multiforme: concepts and candidates. *Cancer J.* 2012 Jan-Feb; 18(1): 69-81 |
| NDV (MTH-68) | | | Case Studies/Series; Malignant glioma; IV; Wollmann et al. Oncolytic virus therapy for glioblastoma multiforme: concepts and candidates. *Cancer J.* 2012 Jan-Feb; 18(1): 69-81; Csatary LK, Bakacs T. Use of Newcastle disease virus vaccine (MTH-68/H) in a patient with high-grade glioblastoma. JAMA. 1999; 281: 1588Y1589.<br>Case Studies/Series; Malignant glioma; IV; Wollmann et al. Oncolytic virus therapy for glioblastoma multiforme: concepts and candidates. *Cancer J.* 2012 Jan-Feb; 18(1): 69-81; Csatary LK, Gosztonyi G, Szeberenyi J, et al. MTH-68/H oncolytic viral treatment in human high-grade gliomas. J Neurooncol. 2004; 67: 83Y93.<br>Case Studies/Series; Malignant glioma; IV; Wollmann et al. Oncolytic virus therapy for glioblastoma multiforme: concepts and candidates. *Cancer J.* 2012 Jan-Feb; 18(1): 69-81; Wagner S, Csatary CM, Gosztonyi G, et al. Combined treatment of pediatric high-grade glioma with the oncolytic viral strain MTH-68/H and oral valproic acid. APMIS. 2006; 114: 731Y743. |
| Measles (MV-CEA) | | | Phase I; Malignant glioma; IT injection; Wollmann et al. Oncolytic virus therapy for glioblastoma multiforme: concepts and candidates. *Cancer J.* 2012 Jan-Feb; 18(1): 69-81 |
| H1 H1PV | | | Phase I; Malignant glioma; IT injection; Wollmann et al. Oncolytic virus therapy for glioblastoma multiforme: concepts and candidates. *Cancer J.* 2012 Jan-Feb; 18(1): 69-81 |
| Polio (PVS-RIPO) | | | Phase I; Malignant glioma; convection-enahnced IT injection; Wollmann et at. Oncolytic virus therapy for glioblastoma multiforme: concepts and candidates. *Cancer J.* 2012 Jan-Feb; 18(1): 69-81 |

Cancers

The methods and compositions of the present invention may be used to treat a wide variety of cancer types. One of skill in the art will appreciate that, since cells of many if not all cancers are capable of receptor-mediated apoptosis, the methods and compositions of the present invention are broadly applicable to many if not all cancers. The combinatorial approach of the present invention is efficacious in various aggressive, treatment refractory tumor models. In particular embodiments, for example, the cancer treated by a method of the present invention may be adrenal cancer, basal cell carcinoma, biliary tract cancer, bladder cancer, bone cancer, brain and other central nervous system (CNS) cancer, breast cancer, cervical cancer, choriocarcinoma, colon cancer, colorectal cancer, connective tissue cancer, cancer of the digestive system, endometrial cancer, epipharyngeal carcinoma, esophageal cancer, eye cancer, gallbladder cancer, gastric cancer, cancer of the head and neck, hepatocellular carcinoma, intra-epithelial neoplasm, kidney cancer, laryngeal cancer, leukemia, liver cancer, liver metastases, lung cancer, lymphomas including Hodgkin's and non-Hodgkin's lymphomas, melanoma, myeloma, multiple myeloma, neuroblastoma, mesothelioma, neuroglioma, myelodysplastic syndrome, multiple myeloma, oral cavity cancer (e.g. lip, tongue, mouth, and pharynx), ovarian cancer, paediatric cancer, pancreatic cancer, pancreatic endocrine tumors, penile cancer, plasma cell tumors, pituitary adenomathymoma, prostate cancer, renal cell carcinoma, cancer of the respiratory system, rhabdomyosarcoma, salivary gland cancer, sarcoma, skin cancer, small bowel cancer, stomach cancer, testicular cancer, thyroid cancer, ureteral cancer, cancer of the urinary system, and other carcinomas and sarcomas. Other cancers are known in the art.

The cancer may be a cancer that is refractory to treatment by SMCs alone. The methods and compositions of the present invention may be particularly useful in cancers that are refractory to treatment by SMCs alone. Typically, a cancer refractory to treatment with SMCs alone may be a cancer in which IAP-mediated apoptotic pathways are not significantly induced. In particular embodiments, a cancer of the present invention is a cancer in which one or more apoptotic pathways are not significantly induced, i.e., is not activated in a manner such that treatment with SMCs alone is sufficient to effectively treat the cancer. For instance, a cancer of the present invention can be a cancer in which a cIAP1/2-mediated apoptotic pathway is not significantly induced.

A cancer of the present invention may be a cancer refractory to treatment by one or more immunostimulatory agents. In particular embodiments, a cancer of the present invention may be a cancer refractory to treatment by one or more immunostimulatory agents (absent an SMC) and also refractory to treatment by one or more SMCs (absent an immunostimulatory agent).

Formulations and Administration

In some instances, delivery of a naked, i.e. native form, of an SMC and/or immunostimulatory agent may be sufficient to potentiate apoptosis and/or treat cancer. SMCs and/or immunostimulatory agents may be administered in the form of salts, esters, amides, prodrugs, derivatives, and the like, provided the salt, ester, amide, prodrug or derivative is suitably pharmacologically effective, e.g., capable of potentiating apoptosis and/or treating cancer.

Salts, esters, amides, prodrugs and other derivatives of an SMC or immunostimulatory agent can be prepared using standard procedures known in the art of synthetic organic chemistry. For example, an acid salt of SMCs and/or immunostimulatory agents may be prepared from a free base form of the SMC or immunostimulatory agent using conventional methodology that typically involves reaction with a suitable acid. Generally, the base form of the SMC or immunostimulatory agent is dissolved in a polar organic solvent, such as methanol or ethanol, and the acid is added thereto. The resulting salt either precipitates or can be brought out of solution by addition of a less polar solvent. Suitable acids for preparing acid addition salts include, but are not limited to, both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

An acid addition salt can be reconverted to the free base by treatment with a suitable base. Certain typical acid addition salts of SMCs and/or immunostimulatory agents, for example, halide salts, such as may be prepared using hydrochloric or hydrobromic acids. Conversely, preparation of basic salts of SMCs and/or immunostimulatory agents of the present invention may be prepared in a similar manner using a pharmaceutically acceptable base, such as sodium hydroxide, potassium hydroxide, ammonium hydroxide, calcium hydroxide, trimethylamine, or the like. Certain typical basic salts include, but are not limited to, alkali metal salts, e.g., sodium salt, and copper salts.

Preparation of esters may involve functionalization of, e.g., hydroxyl and/or carboxyl groups that are present within the molecular structure of SMCs and/or immunostimulatory agents. In certain embodiments, the esters are acyl-substituted derivatives of free alcohol groups, i.e., moieties derived from carboxylic acids of the formula RCOOH where R is alky, and preferably is lower alkyl. Esters may be reconverted to the free acids, if desired, by using conventional hydrogenolysis or hydrolysis procedures.

Amides may also be prepared using techniques known in the art. For example, an amide may be prepared from an ester using suitable amine reactants or prepared from an anhydride or an acid chloride by reaction with ammonia or a lower alkyl amine.

An SMC or immunostimulatory agent of the present invention may be combined with a pharmaceutically acceptable carrier (excipient) to form a pharmacological composition. Pharmaceutically acceptable carriers can contain one or more physiologically acceptable compound(s) that act, e.g., to stabilize the composition, increase or decrease the absorption of the SMC or immunostimulatory agent, or improve penetration of the blood brain barrier (where appropriate). Physiologically acceptable compounds may include, e.g., carbohydrates (e.g., glucose, sucrose, or dextrans), antioxidants (e.g. ascorbic acid or glutathione), chelating agents, low molecular weight proteins, protection and uptake enhancers (e.g., lipids), compositions that reduce the clearance or hydrolysis of the active agents, or excipients or other stabilizers and/or buffers. Other physiologically acceptable compounds, particularly of use in the preparation of tablets, capsules, gel caps, and the like include, but are not limited to, binders, diluents/fillers, disintegrants, lubricants, suspending agents, and the like. In certain embodiments, a pharmaceutical formulation may enhance delivery or efficacy of an SMC or immunostimulatory agent.

In various embodiments, an SMC or immunostimulatory agent of the present invention may be prepared for parenteral, topical, oral, nasal (or otherwise inhaled), rectal, or local administration. Administration may occur, for example, transdermally, prophylactically, or by aerosol.

A pharmaceutical composition of the present invention may be administered in a variety of unit dosage forms depending upon the method of administration. Suitable unit dosage forms, include, but are not limited to, powders, tablets, pills, capsules, lozenges, suppositories, patches, nasal sprays, injectibles, implantable sustained-release formulations, and lipid complexes.

In certain embodiments, an excipient (e.g., lactose, sucrose, starch, mannitol, etc.), an optional disintegrator (e.g. calcium carbonate, carboxymethylcellulose calcium, sodium starch glycollate, crospovidone, etc.), a binder (e.g. alpha-starch, gum arabic, microcrystalline cellulose, carboxymethylcellulose, polyvinylpyrrolidone, hydroxypropylcellulose, cyclodextrin, etc.), or an optional lubricant (e.g., talc, magnesium stearate, polyethylene glycol 6000, etc.) may be added to an SMC or immunostimulatory agent and the resulting composition may be compressed to manufacture an oral dosage form (e.g., a tablet). In particular embodiments, a compressed product may be coated, e.g., to mask the taste of the compressed product, to promote enteric dissolution of the compressed product, or to promote sustained release of the SMC or immunostimulatory agent. Suitable coating materials include, but are not limited to, ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds that may be included in a pharmaceutical composition including an SMC or immunostimulatory agent may include wetting agents, emulsifying agents, dispersing agents or preservatives that are particularly useful for preventing the growth or action of microorganisms. Various preservatives are well known and include, for example, phenol and ascorbic acid. The choice of pharmaceutically acceptable carrier(s), including a physiologically acceptable compound, depends, e.g., on the route of administration of the SMC or immunostimulatory agent and on the particular physio-chemical characteristics of the SMC or immunostimulatory agent.

In certain embodiments, one or more excipients for use in a pharmaceutical composition including an SMC or immunostimulatory agent may be sterile and/or substantially free of undesirable matter. Such compositions may be sterilized by conventional techniques known in the art. For various oral dosage form excipients, such as tablets and capsules, sterility is not required. Standards are known in the art, e.g., the USP/NF standard.

An SMC or immunostimulatory agent pharmaceutical composition of the present invention may be administered in a single or in multiple administrations depending on the dosage, the required frequency of administration, and the known or anticipated tolerance of the subject for the pharmaceutical composition with respect to dosages and frequency of administration. In various embodiments, the composition may provide a sufficient quantity of an SMC or immunostimulatory agent of the present invention to effectively treat cancer.

The amount and/or concentration of an SMC or immunostimulatory agent to be administered to a subject may vary widely, and will typically be selected primarily based on activity of the SMC or immunostimulatory agent and the characteristics of the subject, e.g., species and body weight, as well as the particular mode of administration and the needs of the subject, e.g., with respect to a type of cancer. Dosages may be varied to optimize a therapeutic and/or prophylactic regimen in a particular subject or group of subjects.

In certain embodiments, an SMC or immunostimulatory agent of the present invention is administered to the oral cavity, e.g., by the use of a lozenge, aersol spray, mouthwash, coated swab, or other mechanism known in the art.

In certain embodiments, an SMC or immunostimulatory agent of the present invention may be administered systemically (e.g., orally or as an injectable) in accordance with standard methods known in the art. In certain embodiments, the SMC or immunostimulatory agent may be delivered through the skin using a transdermal drug delivery systems, i.e., transdermal "patches," wherein the SMCs or immunostimulatory agents are typically contained within a laminated structure that serves as a drug delivery device to be affixed to the skin. In such a structure, the drug composition is typically contained in a layer or reservoir underlying an upper backing layer. The reservoir of a transdermal patch includes a quantity of an SMC or immunostimulatory agent that is ultimately available for delivery to the surface of the skin. Thus, the reservoir may include, e.g., an SMC or immunostimulatory agent of the present invention in an adhesive on a backing layer of the patch or in any of a variety of different matrix formulations known in the art. The patch may contain a single reservoir or multiple reservoirs.

In particular transdermal patch embodiments, a reservoir may comprise a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, and polyurethanes. Alternatively, the SMC and/or immunostimulatory agent-containing reservoir and skin contact adhesive are present as separate and distinct layers, with the adhesive underlying the reservoir which, in this case, may be either a polymeric matrix as described above, a liquid or hydrogel reservoir, or another form of reservoir known in the art. The backing layer in these laminates, which serves as the upper surface of the device, preferably functions as a primary structural element of the patch and provides the device with a substantial portion of flexibility. The material selected for the backing layer is preferably substantially impermeable to the SMC and/or immunostimulatory agent and to any other materials that are present.

Additional formulations for topical delivery include, but are not limited to, ointments, gels, sprays, fluids, and creams. Ointments are semisolid preparations that are typically based on petrolatum or other petroleum derivatives. Creams including an SMC or immunostimulatory agent are typically viscous liquids or semisolid emulsions, e.g. oil-in-water or water-in-oil emulsions. Cream bases are typically water-washable and include an oil phase, an emulsifier, and an aqueous phase. The oil phase, also sometimes called the "internal" phase, of a cream base is generally comprised of petrolatum and a fatty alcohol, e.g., cetyl alcohol or stearyl alcohol; the aqueous phase usually, although not necessarily, exceeds the oil phase in volume, and generally contains a humectant. The emulsifier in a cream formulation is generally a nonionic, anionic, cationic, or amphoteric surfactant. The specific ointment or cream base to be used may be selected to provide for optimum drug delivery according to the art. As with other carriers or vehicles, an ointment base may be inert, stable, non-irritating, and non-sensitizing.

Various buccal and sublingual formulations are also contemplated.

In certain embodiments, administration of an SMC or immunostimulatory agent of the present invention may be parenteral. Parenteral administration may include intraspinal, epidural, intrathecal, subcutaneous, or intravenous administration. Means of parenteral administration are known in the art. In particular embodiments, parenteral administration may include a subcutaneously implanted device.

In certain embodiments, it may be desirable to deliver an SMC or immunostimulatory agent to the brain. In embodiments including system administration, this could require that the SMC or immunostimulatory agent cross the blood brain barrier. In various embodiments this may be facilitated by co-administering an SMC or immunostimulatory agent with carrier molecules, such as cationic dendrimers or arginine-rich peptides, which may carry an SMC or immunostimulatory agent over the blood brain barrier.

In certain embodiments, an SMC or immunostimulatory agent may be delivered directly to the brain by administration through the implantation of a biocompatible release system (e.g., a reservoir), by direct administration through an implanted cannula, by administration through an implanted or partially implanted drug pump, or mechanisms of similar function known the art. In certain embodiments, an SMC or immunostimulatory agent may be systemically administered (e.g., injected into a vein). In certain embodiments, it is expected that the SMC or immunostimulatory agent will be transported across the blood brain barrier without the use of additional compounds included in a pharmaceutical composition to enhance transport across the blood brain barrier.

In certain embodiments, one or more an SMCs or immunostimulatory agents of the present invention may be provided as a concentrate, e.g., in a storage container or soluble capsule ready for dilution or addition to a volume of water, alcohol, hydrogen peroxide, or other diluent. A concentrate of the present invention may be provided in a particular amount of an SMC or immunostimulatory agent and/or a particular total volume. The concentrate may be formulated for dilution in a particular volume of diluents prior to administration.

An SMC or immunostimulatory agent may be administered orally in the form of tablets, capsules, elixirs or syrups, or rectally in the form of suppositories. The compound may also be administered topically in the form of foams, lotions, drops, creams, ointments, emollients, or gels. Parenteral administration of a compound is suitably performed, for example, in the form of saline solutions or with the compound incorporated into liposomes. In cases where the compound in itself is not sufficiently soluble to be dissolved, a solubilizer, such as ethanol, can be applied. Other suitable formulations and modes of administration are known or may be derived from the art.

An SMC or immunostimulatory agent of the present invention may be administered to a mammal in need thereof, such as a mammal diagnosed as having cancer. An SMC or immunostimulatory agent of the present invention may be administered to potentiate apoptosis and/or treat cancer.

A therapeutically effective dose of a pharmaceutical composition of the present invention may depend upon the age of the subject, the gender of the subject, the species of the subject, the particular pathology, the severity of the symptoms, and the general state of the subject's health.

The present invention includes compositions and methods for the treatment of a human subject, such as a human subject having been diagnosed with cancer. In addition, a pharmaceutical composition of the present invention may be suitable for administration to an animal, e.g., for veterinary use. Certain embodiments of the present invention may include administration of a pharmaceutical composition of the present invention to non-human organisms, e.g., a non-human primates, canine, equine, feline, porcine, ungulate, or lagomorphs organism or other vertebrate species.

Therapy according to the invention may be performed alone or in conjunction with another therapy, e.g., another cancer therapy, and may be provided at home, the doctor's office, a clinic, a hospital's outpatient department, or a hospital. Treatment optionally begins at a hospital so that the doctor can observe the therapy's effects closely and make any adjustments that are needed or it may begin on an outpatient basis. The duration of the therapy depends on the type of disease or disorder being treated, the age and condition of the subject, the stage and type of the subject's disease, and how the patient responds to the treatment.

In certain embodiments, the combination of therapy of the present invention further includes treatment with a recombinant interferon, such as IFN-$\alpha$, IFN-$\beta$, IFN-$\gamma$, pegylated IFN, or liposomal interferon. In some embodiments, the combination of therapy of the present invention further includes treatment with recombinant TNF-$\alpha$, e.g., for isolated-limb perfusion. In particular embodiments, the combination therapy of the present invention further includes treatment with one or more of a TNF-$\alpha$ or IFN-inducing compound, such as DMXAA, Ribavirin, or the like. Additional cancer immunotherapies that may be used in combination with present invention include antibodies, e.g., monoclonal antibodies, targeting CTLA-4, PD-1, PD-L1, PD-L2, or other checkpoint inhibitors.

Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration.

In any of the above embodiments, the route of administration may be optimized based on the characteristics of the SMC or immunostimulatory agent. In some instances, the SMC or immunostimulatory agent is a small molecule or compound. In other instances, the SMC or immunostimulatory agent is a nucleic acid. In still other instances, the immunostimulatory agent may be a cell or virus. In any of these or other embodiments, appropriate formulations and routes of administration will be selected in accordance with the art.

In the embodiments of the present invention, an SMC and an immunostimulatory agent are administered to a subject in need thereof, e.g., a subject having cancer. In some instances, the SMC and immunostimulatory agent will be administered simultaneously. In some embodiments, the SMC and immunostimulatory agent may be present in a single therapeutic dosage form. In other embodiments, the SMC and immunostimulatory agent may be administered separately to the subject in need thereof. When administered separately, the SMC and immunostimulatory agent may be administered simultaneously or at different times. In some instances, a subject will receive a single dosage of an SMC and a single dosage of an immunostimulatory agent. In certain embodiments, one or more of the SMC and immunostimulatory agent will be administered to a subject in two or more doses. In certain embodiments, the frequency of administration of an SMC and the frequency of administration of an immunostimulatory agent are non-identical, i.e., the SMC is administered at a first frequence and the immunostimulatory agent is administered at a second frequency.

In some embodiments, an SMC is administered within one week of the administration of an immunostimulatory agent. In particular embodiments, an SMC is administered within 3 days (72 hours) of the administration of an immunostimulatory agent. In still more particular embodiments, an SMC is administered within 1 day (24 hours) of the administration of an immunostimulatory agent.

In particular embodiments of any of the methods of the present invention, the SMC and immunostimulatory agent are administered within 28 days of each other or less, e.g., within 14 days of each other. In certain embodiments of any of the methods of the present invention, the SMC and immunostimulatory agent are administered, e.g., simultaneously or within 1 minute, 5 minutes, 10 minutes, 15 minutes, 30 minutes, 1 hour, 2 hours, 4 hours, 6 hours, 12 hours, 18 hours, 24 hours, 36 hours, 2 days, 4 days, 8 days, 10 days, 12 days, 16 days, 20 days, 24 days, or 28 days of each other. In any of these embodiments, the first administration of an SMC of the present invention may precede the first administration of an immunostimulatory agent of the present invention. Alternatively, in any of these embodiments, the first administration of an SMC of the present invention may follow the first administration of an immunostimulatory agent of the present invention. Because an SMC and/or immunostimulatory agent of the present invention may be administered to a subject in two more doses, and because, in such instances, doses of the SMC and immunostimulatory agent of the present invention may be administered at different frequencies, it is not required that the period of time between the administration of an SMC and the administration of an immunostimulatory agent remain constant within a given course of treatment or for a given subject.

One or both of the SMC and the immunostimulatory agent may be administered in a low dosage or in a high dosage. In embodiments in which the SMC and immunostimulatory agent are formulated separately, the pharmacokinetic profiles for each agent can be suitably matched to the formulation, dosage, and route of administration, etc. In some instances, the SMC is administered at a standard or high dosage and the immunostimulatory agent is administered at a low dosage. In some instances, the SMC is administered at a low dosage and the immunostimulatory agent is administered at a standard or high dosage. In some instances, both of the SMC and the immunostimulatory agent are administered at a standard or high dosage. In some instances, both of the SMC and the immunostimulatory agent are administered at a low dosage.

The dosage and frequency of administration of each component of the combination can be controlled independently. For example, one component may be administered three times per day, while the second component may be administered once per day or one component may be administered once per week, while the second component may be administered once per two weeks. Combination therapy may be given in on-and-off cycles that include rest periods so that the subject's body has a chance to recover from effects of treatment.

Kits

In general, kits of the invention contain one or more SMCs and one or more immunostimulatory agents. These can be provided in the kit as separate compositions, or combined into a single composition as described above. The kits of the invention can also contain instructions for the administration of one or more SMCs and one or more immunostimulatory agents.

Kits of the invention can also contain instructions for administering an additional pharmacologically acceptable substance, such as an agent known to treat cancer that is not an SMC or immunostimulatory agent of the present invention.

The individually or separately formulated agents can be packaged together as a kit. Non-limiting examples include kits that contain, e.g., two pills, a pill and a powder, a suppository and a liquid in a vial, two topical creams, ointments, foams etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dosage regimen or in which the individual compounds may vary in potency as therapy progresses); or the kit may contain multiple doses suitable for administration to multiple subjects ("bulk packaging"). The kit components may be assembled in cartons, blister packs, bottles, tubes, and the like.

The dosage of each compound of the claimed combinations depends on several factors, including: the administration method, the disease (e.g., a type of cancer) to be treated, the severity of the disease, and the age, weight, and health of the person to be treated. Additionally, pharmacogenomic (the effect of genotype on the pharmacokinetic, pharmacodynamic or efficacy profile of a therapeutic) information about a particular subject may affect the dosage regimen or other aspects of administration.

EXAMPLES

Example 1

Smac Mimetics Prime Tumors for Destruction by the Innate Immune System

Smac mimetic compounds are a class of apoptosis sensitizing drugs that have proven safe in cancer patient Phase I trials. Stimulating an innate anti-pathogen response may generate a potent yet safe inflammatory "cytokine storm" that would trigger death of tumors treated with Smac mimetics. The present example demonstrates that activation of innate immune responses via oncolytic viruses and adjuvants, such as poly(I:C) and CpG, induces bystander death of cancer cells treated with Smac mimetics in a manner mediated by IFNβ, TNFα or TRAIL. This therapeutic strategy may lead to durable cures, e.g., in several aggressive mouse models of cancer. With these and other innate immune stimulants having demonstrated safety in human clinical trials, the data provided herein points strongly towards their combined use with Smac mimetics for treating cancer.

The present example examines whether stimulating the innate immune system using pathogen mimetics would be a safe and effective strategy to generate a cytokine milieu necessary to initiate apoptosis in tumors treated with an SMC. We report here that non-pathogenic oncolytic viruses, as well as mimetics of microbial RNA or DNA, such as poly (I:C) and CpG, induce bystander killing of cancer cells treated with an SMC that is dependent either upon IFNβ, TNFα, or TRAIL production. Importantly, this therapeutic strategy was tolerable in vivo and led to durable cures in several aggressive mouse models of cancer.

Figure 1:
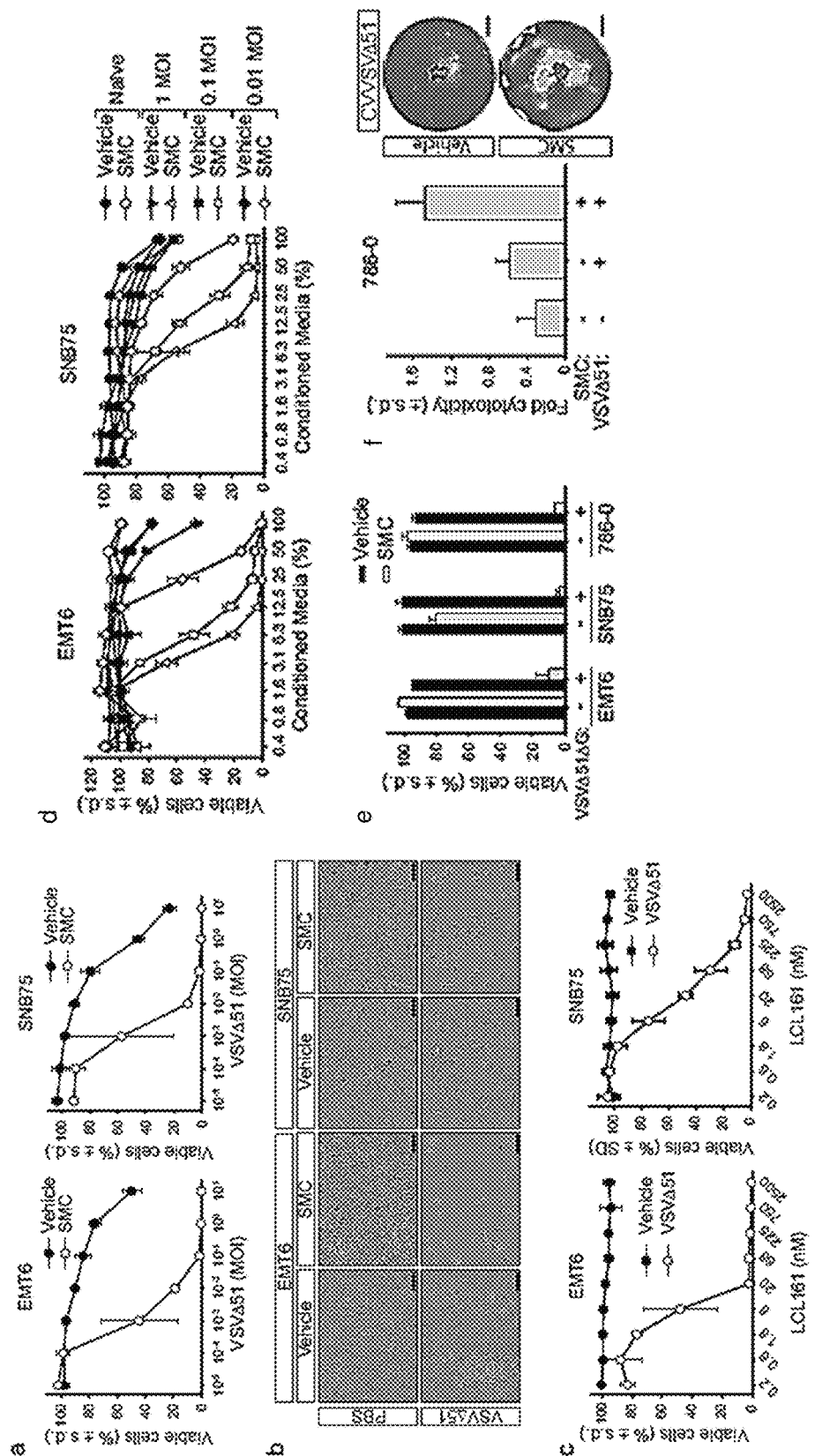
FIGS. 1a-1f are a set of graphs and images showing that SMC synergizes with oncolytic rhabdoviruses to induce cancer cell death. All panels of FIG. 1 are representative of data from at least three independent experiments using biological replicates (n=3).
Figure 6:
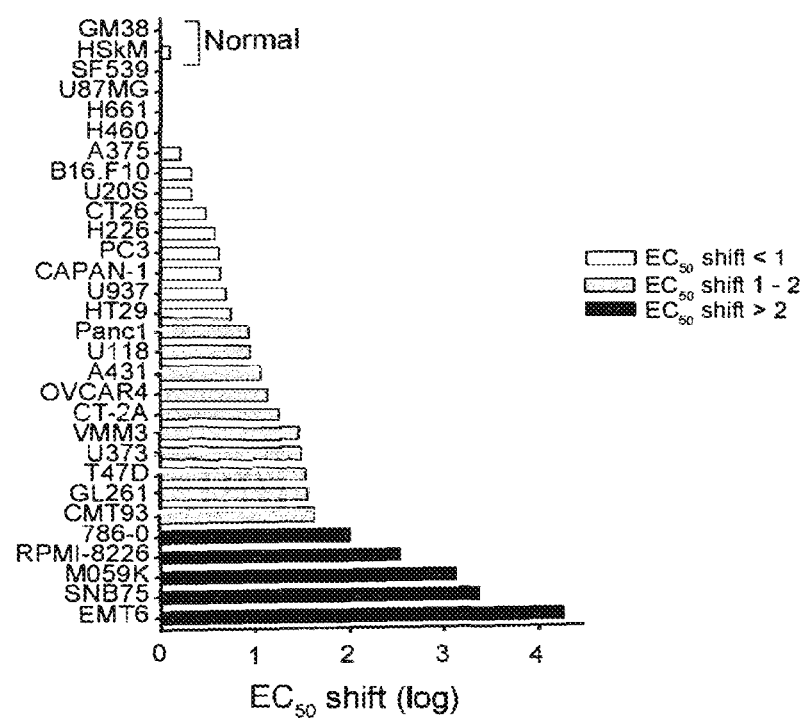
FIG. 6 is a graph showing the responsiveness of a panel of cancer and normal cells to the combinatorial treatment of SMC and OV. The indicated cancer cell lines (n=28) and non-cancer human cells (primary human skeletal muscle (HSkM) and human fibroblasts (GM38)) were treated with LCL161 and increasing VSVΔ51 for 48 hours. The dose required to yield 50% viable cells in the presence in SMC versus vehicle was determined using nonlinear regression and plotted as a log EC50 shift toward increasing sensitivity. Representative data from at least two independent experiments using biological replicates (n=3) are shown.
Figure 7:
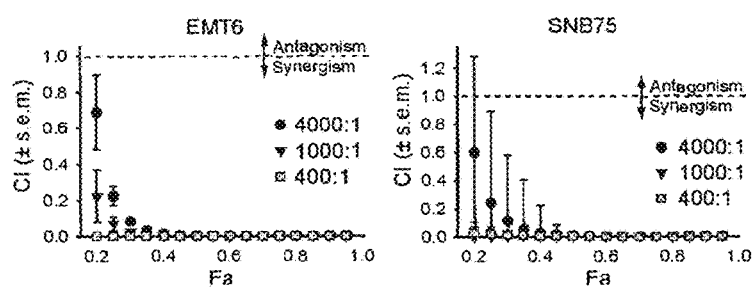
FIG. 7 is pair of graphs showing that SMC and OV co-treatment is highly synergistic in cancer cells. The graphs show Alamar blue viability of cells treated with serial dilutions of a fixed ratio combination mixture of VSVΔ51 and LCL161 (PFU: μM LCL161). Combination indexes (CI) were calculated using Calcusyn. Plots represent the algebraic estimate of the CI in function of the fraction of cells affected (Fa). Error bars, mean±s.e.m. Representative data from three independent experiments using biological replicates (n=3) is shown.
Figure 8:
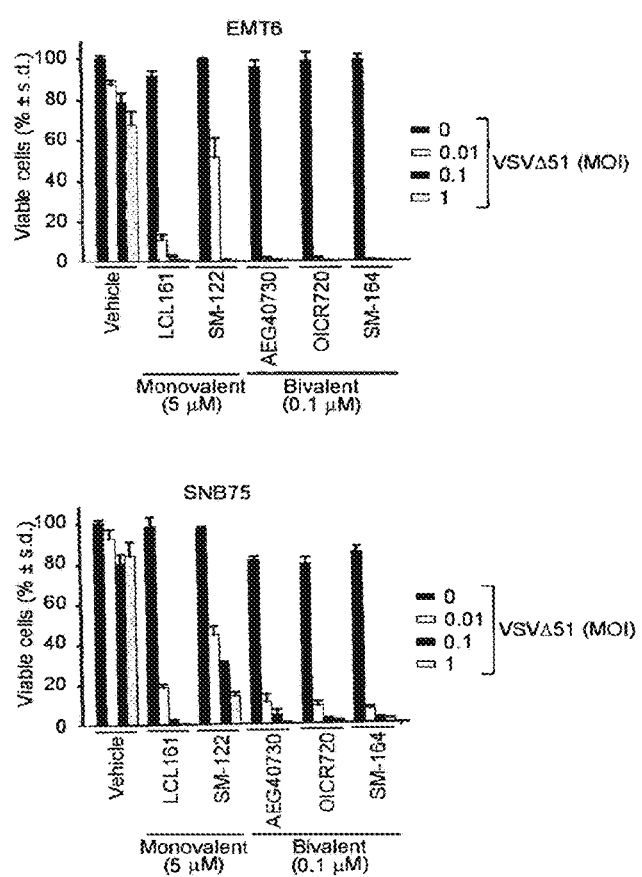
FIG. 8 is a pair of graphs showing that monovalent and bivalent SMCs synergize with OVs to cause cancer cell death. The graphs show the result of Alamar blue viability assay of cells treated with 5 μM monovalent SMCs (LCL161, SM-122) or 0.1 μM bivalent SMCs (AEG40730, OICR720, SM-164) and VSVΔ51 at differing MOIs. Error bars, mean±s.d. Representative data from three independent experiments using biological replicates (n=3) is shown.
Figure 9:
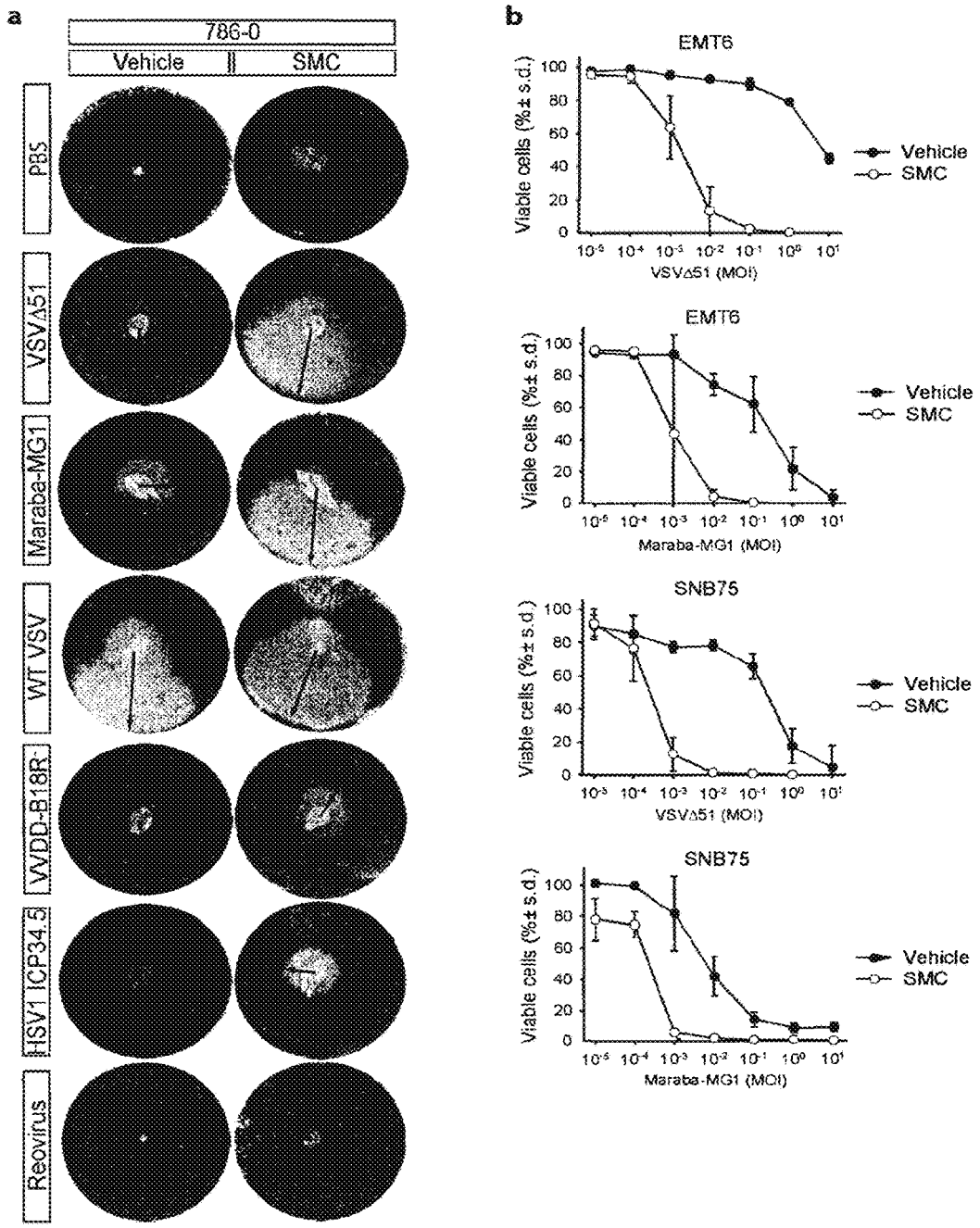
FIGS. 9a and 9b are a set of images and graphs showing that SMC-mediated cancer cell death is potentiated by oncolytic viruses.
Figure 10:
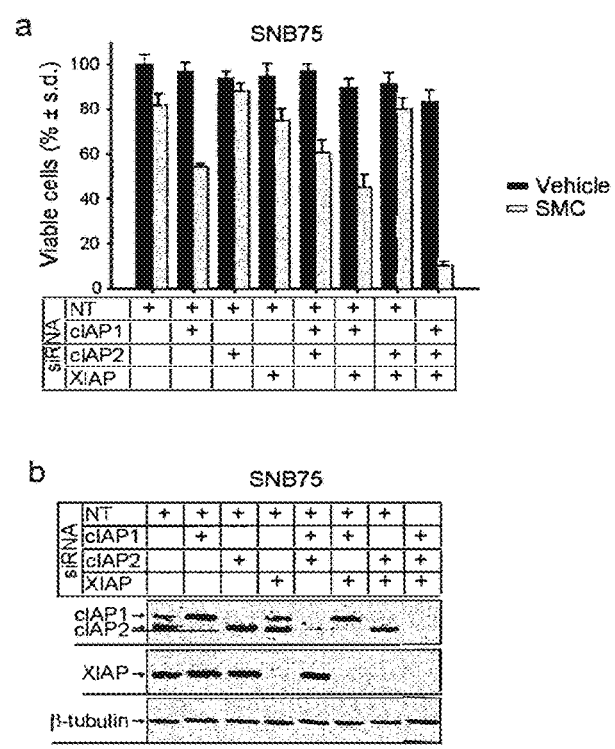
FIGS. 10a and 10b are a set of graphs and images showing that cIAP1, cIAP2 and XIAP cooperatively protect cancer cells from OV-induced cell death.
Figure 24:
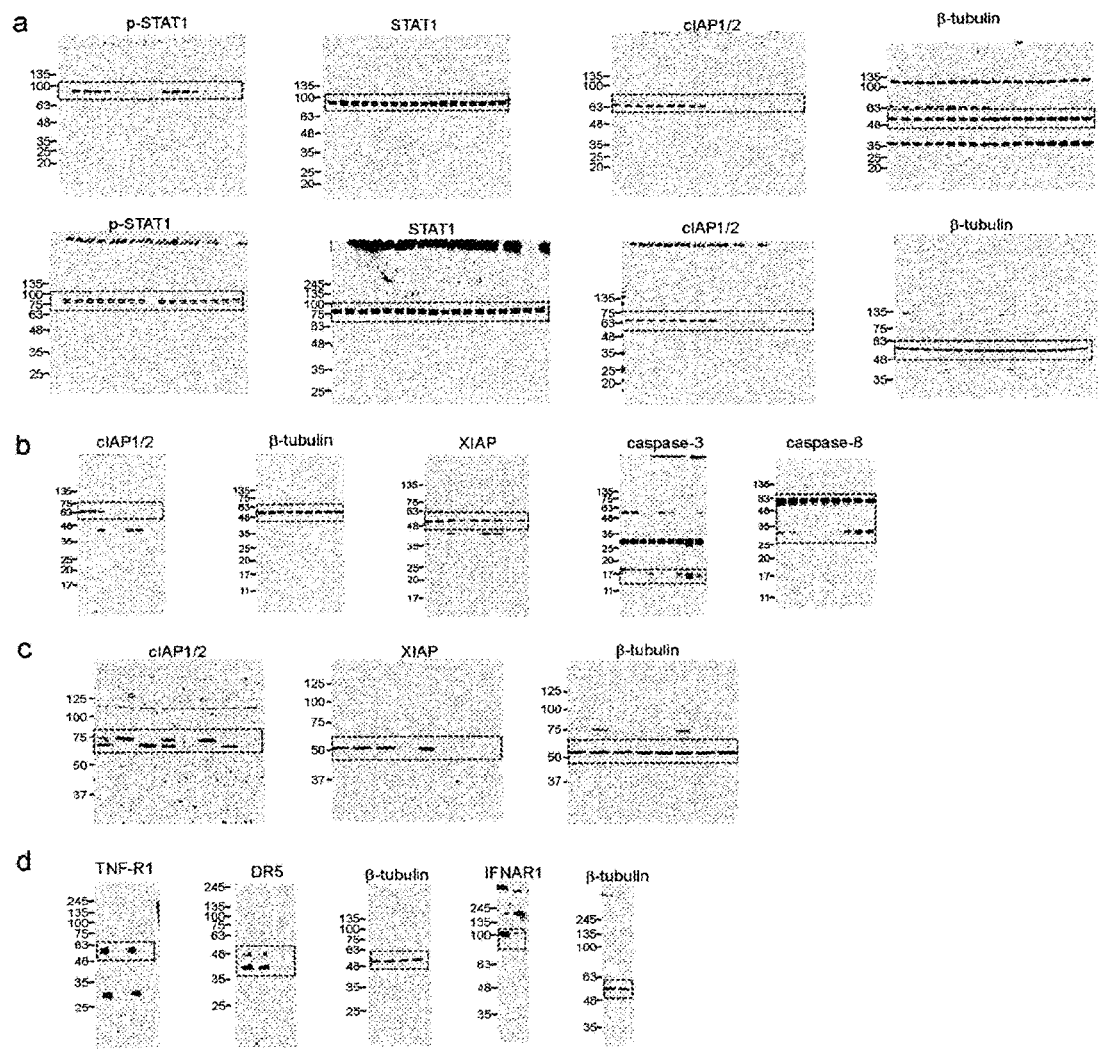
Figure 24:

SMC Therapy Sensitizes Cancer Cells to Bystander Cell Death During Oncolytic Virus Infection Oncolytic viruses (OVs) are emerging biotherapies for cancer currently in phase I-III clinical evaluation. One barrier to OV therapy may be the induction of type I IFN- and NFκB-responsive cytokines by the host, which orchestrate an antiviral state in tumors. It was examined whether we could harness those innate immune cytokines to induce apoptosis in cancer cells pretreated with an SMC. To begin, a small panel of tumor-derived and normal cell lines (n=30) was screened for responsiveness to the SMC LCL161 and the oncolytic rhabdovirus VSVΔ51. We chose LCL161 because this compound is the most clinically advanced drug in the SMC class, and VSVΔ51 because it is known to induce a robust antiviral cytokine response. In 15 of the 28 cancer cell lines tested (54%), SMC treatment enhanced sensitivity the EC50 of VSVΔ51 by 10-10,000 fold (FIG. 6, and representative examples in FIGS. 1a and 1b). Similarly, low dose of VSVΔ51 reduced the EC50 of SMC therapy from undetermined levels (>2500 nM) to 4.5 and 21.9 nM in two representative cell lines: the mouse mammary carcinoma EMT6 and the human glioblastoma SNB75 cells, respectively (FIG. 1c). Combination index analyses determined that the interaction between SMC therapy and VSVΔ51 was synergistic (FIG. 7). Experiments using four other SMCs and five other oncolytic viruses showed that a spectrum of monovalent and bivalent SMCs synergize with VSVΔ51 (FIG. 8). We find that the oncolytic rhabdoviruses, VSVΔ51 and Maraba-MG1, are superior in eliciting bystander killing in synergizing with SMCs, compared to HSV, reovirus, vaccinia and wild-type VSV platforms, all of which have elaborate mechanisms to disarm aspects of innate immune signalling (FIGS. 9a and 9b). Genetic experiments using RNAi-mediated silencing demonstrated that both XIAP and the cIAPs must be inhibited to obtain synergy with VSVΔ51 (FIGS. 10a, 10b, and 24c). In stark contrast to the results in tumor-derived cell lines, non-cancer GM38 primary human skin fibroblasts and HSkM human skeletal myoblasts were unaffected by VSVΔ51 and SMC combination therapy (FIG. 6). Taken together, these data indicate that oncolytic VSV synergizes with SMC therapy in a tumor-selective fashion.

Figure 11:
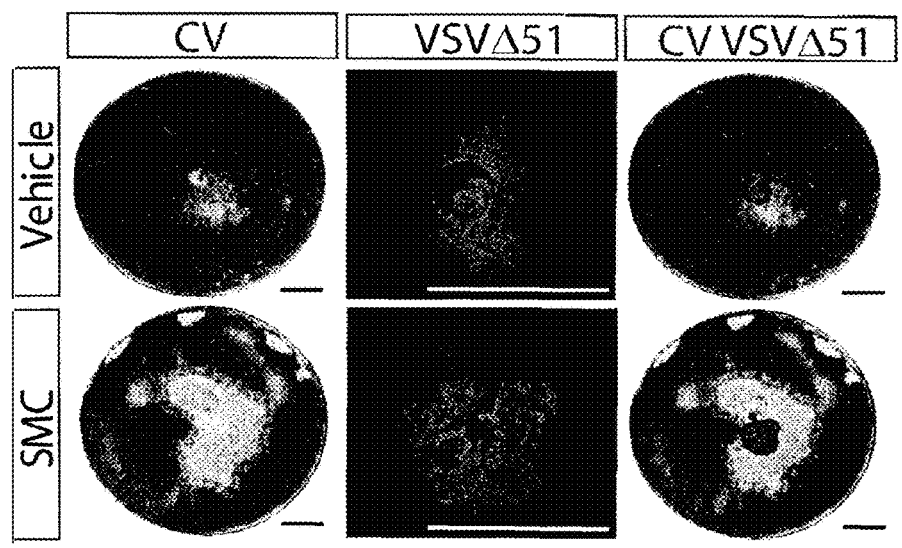
FIG. 11 is a set of images used for superimposed images depicted in FIG. 1g. Cells were overlaid with agarose media containing LCL161, inoculated with VSVΔ51-GFP in the middle of the well, and infectivity measured by fluorescence and cytotoxicity was denoted by crystal violet (CV) staining. Note: the bars represent the same size.

To determine if VSVΔ51 elicits bystander cell death in IAP-depleted neighbouring cells not infected by the virus, cells were treated with SMCs prior to infection with a low dose of VSVΔ51 (MOI=0.01 infectious particles per cell). We assessed whether conditioned media derived from cells infected with VSVΔ51 (which was subsequently inactivated by UV light) could induce death when transferred to a plate of virus naïve cancer cells treated with an SMC. The conditioned media induced cell death only when the cells were co-treated with an SMC (FIG. 1d). We also found that a low-dose of a pseudo-typed G-less strain of VSVΔ51 (MOI=0.1), containing a deletion of the gene encoding for its glycoprotein (VSVΔ51ΔG) that limits the virus to a single round of infection, was toxic to an entire plate of cancer cells treated with an SMC (FIG. 1e). Finally, we performed a cytotoxicity assay in cells overlaid with agarose, used to retard the spread of VSVΔ51 expressing a fluorescent tag, and observed dramatic cell death in SMC treated cells outside of the zone of virus infection (FIGS. 1f and 11). Overall, these results indicate that VSVΔ51 infection leads to the release of at least one soluble factor that can potently induce bystander cell death in neighboring, uninfected, cancer cells treated with SMCs.

Figure 2:
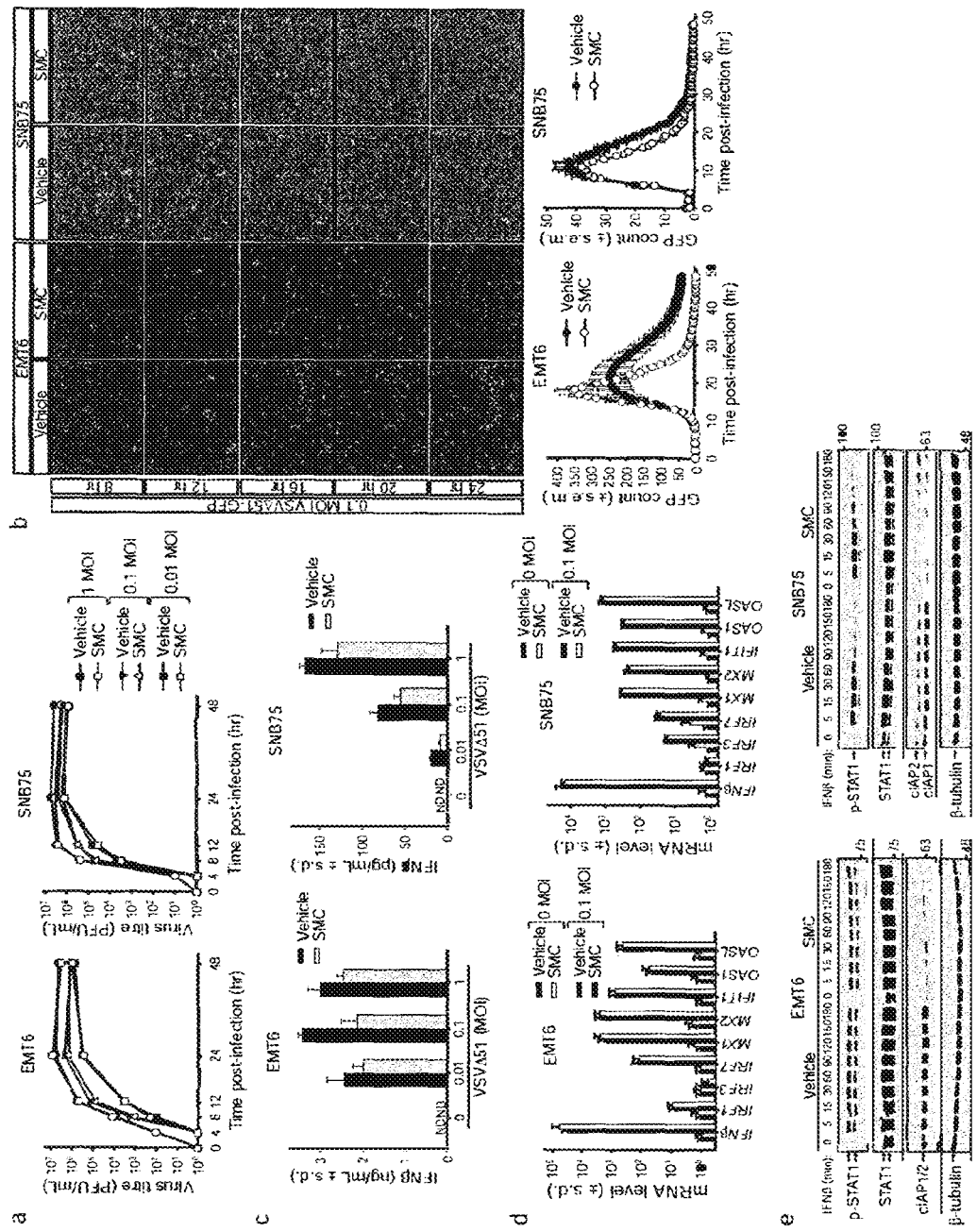
FIGS. 2a-2e are a set of graphs and images showing that SMC treatment does not alter the cancer cell response to oncolytic virus (OV) infection. All panels of FIG. 2 are representative of data from at least three independent experiments using biological replicates.
Figure 12:
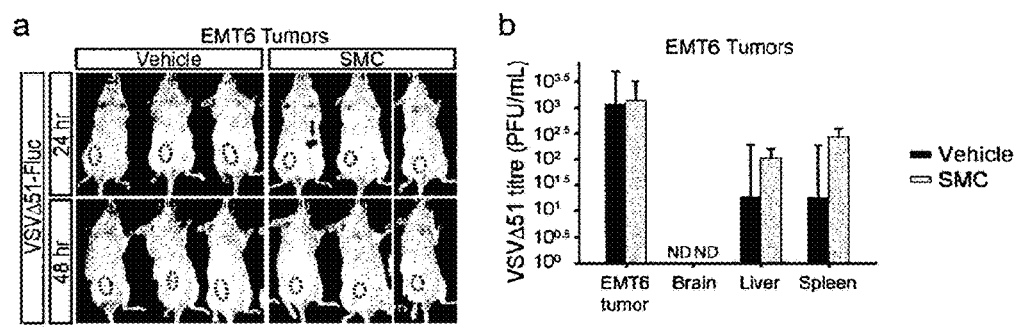
FIGS. 12a and 12b are a set of images and a graph showing that SMC treatment does not affect OV distribution or replication in vivo.

SMC Therapy does not Impair the Cellular Innate Immune Response to Oncolytic VSV The cellular innate immune response to an RNA virus infection in mammalian tumor cells can be initiated by members of a family of cytosolic (RIG-I-like receptors, RLRs) and endosomal (toll-like receptors, TLRs) viral RNA sensors. Once triggered, these receptors can seed parallel IFN-response factor (IRF) 3/7 and nuclear-factor kappa B (NF-κB) cell signalling cascades. These signals can culminate in the production of IFNs and their responsive genes as well as an array of inflammatory chemokines and cytokines. This prompts neighboring cells to preemptively express an armament of antiviral genes and also aids in the recruitment and activation of cells within the innate and adaptive immune systems to ultimately clear the virus infection. The cIAP proteins have recently been implicated in numerous signalling pathways downstream of pathogen recognition, including those emanating from RLRs and TLRs. Accordingly, it was examined whether SMC therapy alters the antiviral response to oncolytic VSV infection in tumor cells and in mice. To begin, the effect of SMC therapy on VSVΔ51 productivity and spread was evaluated. Single-step and multi-step growth curves of VSVΔ51 productivity revealed that SMC treatment does not affect the growth kinetics of VSVΔ51 in EMT6 or SNB75 cells in vitro (FIG. 2a). Moreover, analysis through time-lapse microscopy demonstrates that SMC treatment does not alter VSVΔ51 infectivity in or spread through tumor cells (FIG. 2b). Furthermore, viral replication and spread in vivo were analyzed by determining tumor load using IVIS imaging and tissue virus titration. No differences in viral kinetics were found upon SMC treatment in EMT6 tumor-bearing mice (FIGS. 12a and 12b). As EMT6 and SNB75 cells both have functional type I IFN responses that regulate the VSV life cycle, these data provide strong, albeit indirect, evidence that SMC therapy does not affect the antiviral signalling cascades in cancer cells.

To probe deeper, IFNβ production was measured in EMT6 and SNB75 cells treated with VSVΔ51 and SMCs. This experiment revealed that the SMC treated cancer cells respond to VSVΔ51 by secreting IFNβ (FIG. 2c), although at slightly lower levels as compared to VSVΔ51 alone. It was asked whether the dampened IFNβ secretion from SMC treated cells had any bearing on the induction of downstream IFN stimulated genes (ISGs). Quantitative RT-PCR analyses of a small panel of ISGs in cells treated with VSVΔ51 and SMC revealed that IAP inhibition had no bearing on ISG gene expression in response to an oncolytic VSV infection (FIG. 2d). Consistent with this finding, western blot analyses indicated that SMCs do not alter the activation of Jak/Stat signalling downstream of IFNβ (FIGS. 2e and 24a). Collectively, these data suggest that SMCs do not impede the ability of tumor cells to sense and respond to an infection from VSVΔ51.

IFNβ Orchestrates Bystander Cell Death During SMC and Oncolytic VSV Co-therapy

SMCs sensitize a number of cancer cell lines towards caspase 8-dependant apoptosis induced by TNFα, TRAIL, and IL-1β. As RNA viruses can trigger the production of these cytokines as part of the cellular antiviral response, the involvement of cytokine signaling in SMC and OV induced cell death was investigated. To start, the TNF receptor (TNF-R1) and/or the TRAIL receptor (DR5) were silenced and synergy between SMC and VSVΔ51 was assayed. This experiment revealed that TNFα and TRAIL are not only involved, but collectively are indispensable for bystander cell death (FIGS. 3a-3h, 13a, and 24d). Consistent with this finding, western blot and immunofluorescence experiments revealed strong activation of the extrinsic apoptosis pathway, and RNAi knockdown experiments demonstrated a requirement for both caspase-8 and Rip1 in the synergy response (FIGS. 14a-14g, 24e, and 24f). Moreover, engineering TNFα into VSVΔ51 improved synergy with SMC therapy by an order of magnitude (FIGS. 15a and 15b).

Figure 3:
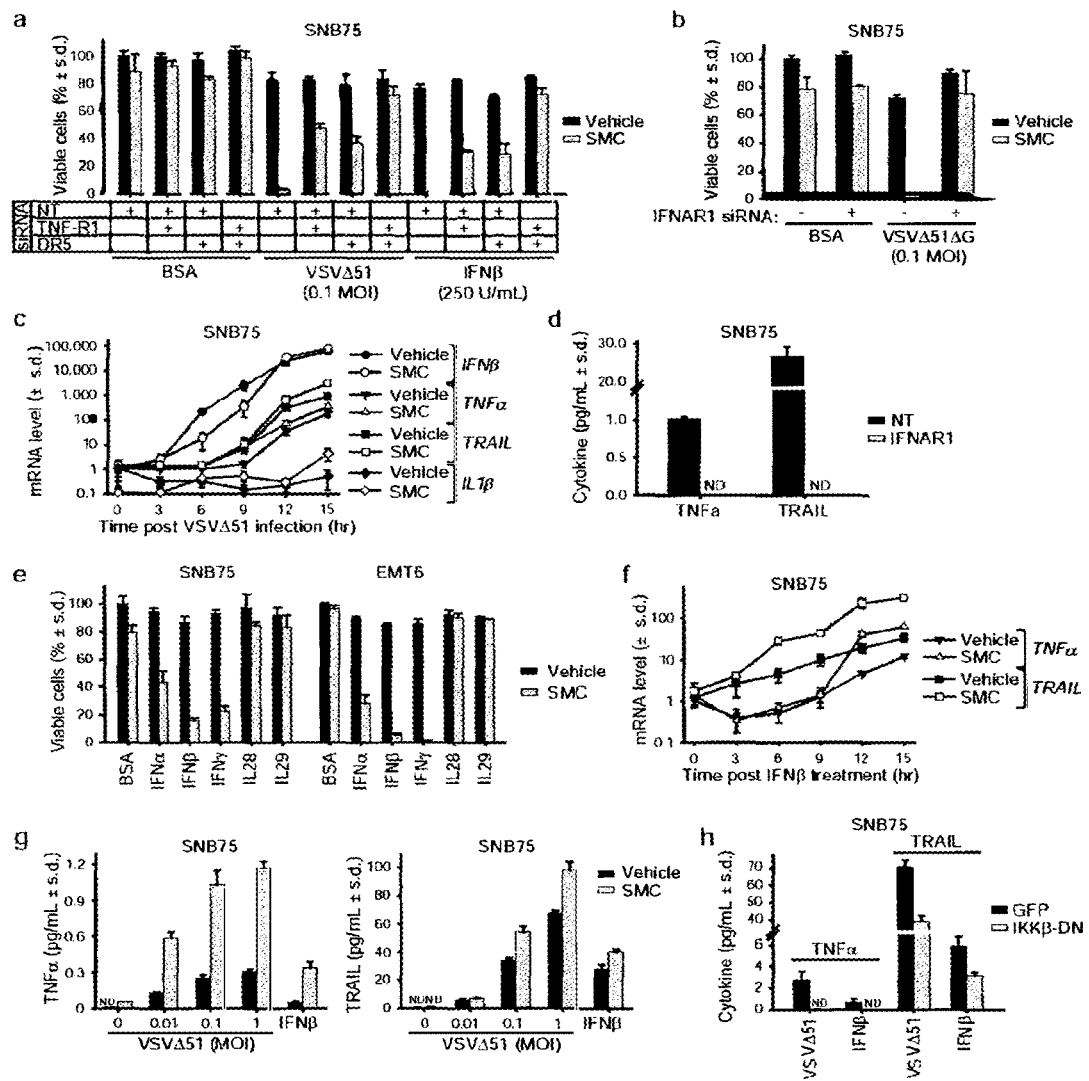
FIGS. 3a-3h are a set of graphs showing that SMC treatment of OV-infected cancer cells leads to type 1 interferons (type 1 IFN) and nuclear-factor kappa B (NF-κb)-dependent production of proinflammatory cytokines. All panels of FIG. 3 are representative of data from at least three independent experiments using biological replicates (n=3).

Next, the type I IFN receptor (IFNAR1) was silenced and it was found, unexpectedly, that IFNAR1 knockdown prevented the synergy between SMC therapy and oncolytic VSV (FIGS. 3b, 13b, and 24d). It was predicted that IFNAR1 knockdown would dampen but not completely suppress bystander killing, as TRAIL is a well-established ISG that is responsive to type I IFN28. TNFα and IL-1β are considered to be independent of IFN signaling, but they are nevertheless responsive to NF-κB signaling downstream of virus detection. This result suggests the possibility of a non-canonical type I IFN-dependant pathway for the production of TNFα and/or IL-1β. Indeed, when the mRNA expression of IFN3, TRAIL, TNFα, and IL-1β were probed during an oncolytic VSV infection, a significant temporal lag was found between the induction of IFNβ and that of both TRAIL and TNFα (FIG. 3c). This data also suggests that TNFα—like TRAIL—may be induced secondary to IFNβ. To prove this concept, IFNAR1 was silenced before treating cells with VSVΔ51. IFNAR1 knockdown completely abrogated the induction of both TRAIL and TNFα by oncolytic VSV (FIG. 3d). Moreover, synergy with SMC was recapitulated using recombinant type I IFNs (IFNα/β) and type II IFN (IFNγ), but not type III IFNs (IL28/29) (FIG. 3e). Taken together, these data indicate that type I IFN is required for the induction of TNFα and TRAIL during a VSVΔ51 infection of tumor cells. Moreover, the production of these cytokines is responsible for bystander killing of neighboring, uninfected SMC-treated cells.

Figure 16:
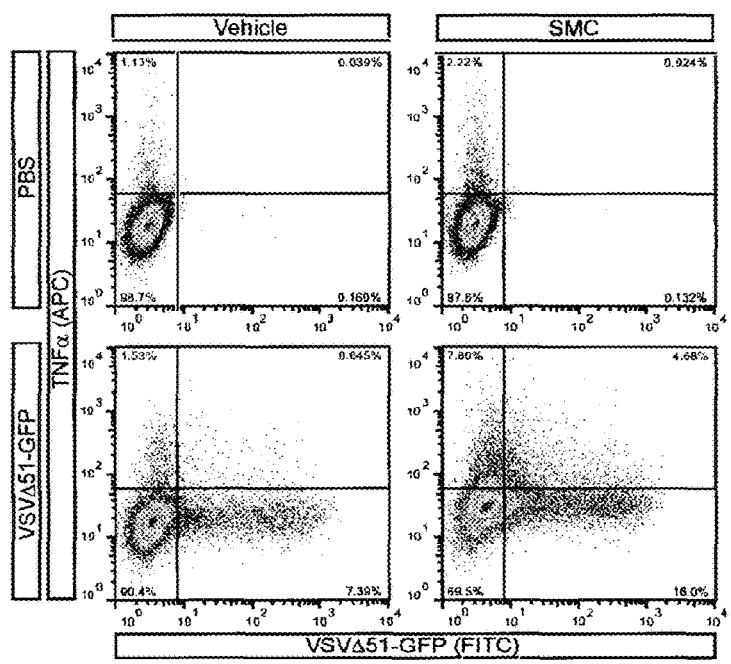
FIG. 16 is a set of images showing that oncolytic virus infection leads to enhanced TNFα expression upon SMC treatment. EMT6 cells were co-treated with 5 μM SMC and 0.1 MOI VSVΔ51-GFP for 24 hours, and cells were processed for the presence of intracellular TNFα via flow cytometry. Images show representative data from four independent experiments.
Figure 18:
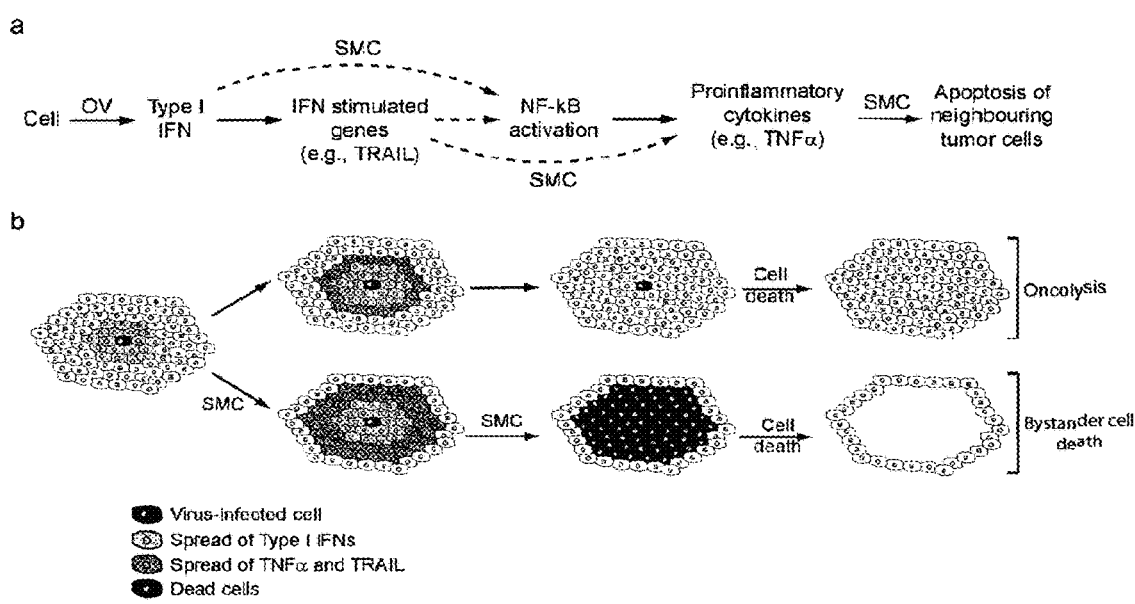
FIGS. 18a and 18b are a schematic of OV-induced type I IFN and SMC synergy in bystander cancer cell death.

To explore the non-canonical induction of TNFα further, the mRNA expression levels of TRAIL and TNFα in SNB75 cells treated with recombinant IFNβ were measured. Both cytokines were induced by IFNβ treatment (FIG. 3f), and ELISA experiments confirmed the production of their respective protein products in the cell culture media (FIG. 3g). Interestingly, there was a significant time lag between the induction of TRAIL and that of TNFα. As TRAIL is a bona fide ISG and TNFα is not, this result raised the possibility that TNFα is not induced by IFNβ directly, but responds to a downstream ISG up-regulated by IFNβ. Thus, quantitative RT-PCR was performed on 176 cytokines in SNB75 cells and 70 that were significantly up-regulated by IFNβ were identified (Table 4). The role of these ISGs in the induction of TNFα by IFNβ is currently being investigated. It is also intriguing that SMC treatment potentiated the induction of both TRAIL and TNFα by IFNβ in SNB75 cells (FIGS. 3f and 3g). Furthermore, using a dominant-negative construct of IKK, it was found that the production of these inflammatory cytokines downstream of IFNβ was dependent, at least in part, on classical NF-κB signalling (FIG. 3h). In EMT6 cells, SMC treatment was found to enhance cellular production of TNFα (5- to 7-fold percentage increase) upon VSV infection (FIG. 16). Finally, it was also demonstrated that blocking TNF-R1 signalling (with antibodies or siRNA) prevents EMT6 cell death in the presence of SMC and VSVΔ51 or IFNβ (FIGS. 17a-17c and 24h). The relationship between type I IFN and TNFα is complex, having either complimentary or inhibitory effects depending on the biological context. However, without limiting the present invention to any particular mechanism of action, a simple working model can be proposed as follows: Tumor cells infected by an oncolytic RNA virus up-regulate type I IFN, and this process is not affected by SMC antagonism of the IAP proteins. Those IFNs in turn signal to neighboring, uninfected cancer cells to express and secrete TNFα and TRAIL, a process that is enhanced by SMC treatment, which consequently induces autocrine and paracrine programmed cell death in uninfected tumor cells exposed to SMC (FIGS. 18a and 18b).

TABLE 4

| VSV | IFNβ | Gene Name | Gene Identification |
|---|---|---|---|
| 25465.4 | 1017.8 | CCL8 | Chemokine (C-C motif) ligand 8 |
| 13388.9 | 44.9 | IL29 | Interleukin 29 (interferon, lambda 1) |
| 5629.3 | 24.3 | IFNB1 | Interferon, beta 1, fibroblast |
| 1526.8 | 16.2 | TNFSF15 | Tumor necrosis factor (ligand) superfamily, member 15 |
| 847 | 24.6 | CCL5 | Chemokine (C-C motif) ligand 5 |
| 747.7 | 17.2 | CCL3 | Chemokine (C-C motif) ligand 3 |
| 650.9 | 60.6 | TNFSF10 | Tumor necrosis factor (ligand) superfamily, member 10 |
| 421.3 | 296.1 | IL12A | Interleukin 12A |
| 289.3 | 10.7 | TNFSF18 | Tumor necrosis factor (ligand) superfamily, member 18 |
| 255.3 | 18.8 | CCL7 | Chemokine (C-C motif) ligand 7 |
| 154.2 | 19.2 | IL6 | Interleukin 6 (interferon, beta 2) |
| 150.8 | 12.9 | IL1RN | Interleukin 1 receptor antagonist |
| 108.1 | 25.5 | CCL20 | Chemokine (C-C motif) ligand 20 |
| 78.6 | 6.2 | CXCL1 | Chemokine (C—X—C motif) ligand 1 |
| 64.7 | 14.8 | CCL2 | Chemokine (C-C motif) ligand 2 |
| 62.5 | 14.5 | CCL4 | Chemokine (C-C motif) ligand 4 |
| 55.6 | 1.2 | CXCL3 | Chemokine (C—X—C motif) ligand 3 |
| 55.2 | 4.3 | TNF | Tumor necrosis factor (TNF superfamily, member 2) |
| 48.8 | 4.3 | IGF1 | Insulin-like growth factor 1 (somatomedin C) |
| 48.4 | 2.8 | CXCL2 | Chemokine (C—X—C motif) ligand 2 |
| 38.5 | 3.8 | CCL11 | Chemokine (C-C motif) ligand 11 |
| 37.5 | 3.8 | HGF | Hepatocyte growth factor |
| 36.5 | 75.1 | NGFB | Nerve growth factor, beta polypeptide |
| 32.9 | 4 | FGF14 | Fibroblast growth factor 14 |
| 24.7 | 25.6 | FGF20 | Fibroblast growth factor 20 |
| 21.5 | 16.4 | IL1B | Interleukin 1, beta |
| 20 | 36.3 | CSF2 | Colony stimulating factor 2 (granulocyte-macrophage) |
| 18.3 | 2.6 | GDF3 | Growth differentiation factor 3 |
| 17.2 | 2 | CCL28 | Chemokine (C-C motif) ligand 28 |
| 12 | 2.1 | CCL22 | Chemokine (C-C motif) ligand 22 |

TABLE 4-continued

| VSV | IFNβ | Gene Name | Gene Identification |
|---|---|---|---|
| 11.3 | 2.5 | CCL17 | Chemokine (C-C motif) ligand 17 |
| 10.5 | 2 | CCL13 | Chemokine (C-C motif) ligand 13 |
| 10.5 | 15.3 | IL20 | Interleukin 20 |
| 9.7 | 22.8 | FGF16 | Fibroblast growth factor 16 |
| 8.8 | 3.6 | TNFSF14 | Tumor necrosis factor (ligand) superfamily, member 14 |
| 8.2 | 2.7 | FGF2 | Fibroblast growth factor 2 (basic) |
| 7.1 | 8.1 | BDNF | Brain-derived neurotrophic factor |
| 7.1 | 9.7 | IL1A | Interleukin 1, alpha |
| 7.1 | 10.9 | ANGPT4 | Angiopoietin 4 |
| 7 | 1.5 | TGFB3 | Transforming growth factor, beta 3 |
| 7 | 5.8 | IL22 | Interleukin 22 |
| 6.9 | 9.7 | IL1F5 | Interleukin 1 family, member 5 (delta) |
| 6.7 | 2.4 | IFNW1 | Interferon, omega 1 |
| 6.6 | 12.6 | IL11 | Interleukin 11 |
| 6.6 | 25.1 | IL1F8 | Interleukin 1 family, member 8 (eta) |
| 6.3 | −1.3 | EDA | Ectodysplasin A |
| 5.9 | 8 | FGF5 | Fibroblast growth factor 5 |
| 5.8 | 5 | VEGFC | Vascular endothelial growth factor C |
| 5.2 | 4.9 | LIF | Leukemia inhibitory factor |
| 5 | 1.3 | CCL25 | Chemokine (C-C motif) ligand 25 |
| 4.9 | 8.3 | BMP3 | Bone morphogenetic protein 3 |
| 4.9 | 1.6 | IL17C | Interleukin 17C |
| 4.8 | −2.3 | TNFSF7 | CD70 molecule |
| 4.3 | 2.5 | TNFSF8 | Tumor necrosis factor (ligand) superfamily, member 8 |
| 4.3 | 2.5 | FASLG | Fas ligand (TNF superfamily, member 6) |
| 4.2 | 2.7 | BMP8B | Bone morphogenetic protein 8b |
| 4.2 | 6 | IL7 | Interleukin 7 |
| 4.1 | 5.2 | CCL24 | Chemokine (C-C motif) ligand 24 |
| 4 | −2.2 | INHBE | Inhibin, beta E |
| 4 | 5.8 | IL23A | Interleukin 23, alpha subunit p19 |
| 3.8 | −1.1 | IL17F | Interleukin 17F |
| 3.7 | 2.9 | CCL21 | Chemokine (C-C motif) ligand 21 |
| 3.5 | 8.5 | CSF1 | Colony stimulating factor 1 (macrophage) |
| 3.5 | 3 | IL15 | Interleukin 15 |
| 3.4 | 5.7 | NRG2 | Neuregulin 2 |
| 3.3 | N/A | INHBB | Inhibin, beta B |
| 3.3 | N/A | LTB | Lymphotoxin beta (TNF superfamily, member 3) |
| 3.3 | N/A | BMP7 | Bone morphogenetic protein 7 |
| 3 | −3.8 | IL1F9 | Interleukin 1 family, member 9 |
| 2.9 | 6.1 | IL12B | Interleukin 12B |
| 2.8 | 6.2 | FLT3LG | Fms-related tyrosine kinase 3 ligand |
| 2.7 | 3 | FGF1 | Fibroblast growth factor 1 (acidic) |
| 2.5 | −2 | CXCL13 | Chemokine (C—X—C motif) ligand 13 |
| 2.4 | 2.2 | IL17B | Interleukin 17B |
| 2.3 | 7.8 | GDNF | Glial cell derived neurotrophic factor |
| 2.3 | −1.7 | GDF7 | Growth differentiation factor 7 |
| 2.3 | −2.4 | LTA | Lymphotoxin alpha (TNF superfamily, member 1) |
| 2.2 | 1.7 | LEFTY2 | Left-right determination factor 2 |
| 2.1 | 5 | FGF19 | Fibroblast growth factor 19 |
| 2.1 | 9.8 | FGF23 | Fibroblast growth factor 23 |
| 2.1 | 4.8 | CLC | Cardiotrophin-like cytokine factor 1 |
| 2.1 | 3 | ANGPT1 | Angiopoietin 1 |
| 2 | 10.6 | TPO | Thyroid peroxidase |
| 2 | 2.1 | EFNA5 | Ephrin-A5 |
| 1.9 | 6.4 | IL1F10 | Interleukin 1 family, member 10 (theta) |
| 1.9 | 7.6 | LEP | Leptin (obesity homolog, mouse) |
| 1.8 | 3 | IL5 | Interleukin 5 (colony-stimulating factor, eosinophil) |
| 1.8 | 5.7 | IFNE1 | Interferon epsilon 1 |
| 1.8 | 2.7 | EGF | Epidermal growth factor (beta-urogastrone) |
| 1.7 | 3.4 | CTF1 | Cardiotrophin 1 |
| 1.7 | −1.9 | BMP2 | Bone morphogenetic protein 2 |
| 1.7 | 3 | EFNB2 | Ephrin-B2 |
| 1.6 | 1 | FGF8 | Fibroblast growth factor 8 (androgen-induced) |
| 1.6 | −2 | TGFB2 | Transforming growth factor, beta 2 |
| 1.5 | −1.6 | BMP8A | Bone morphogenetic protein 8a |
| 1.5 | 3.3 | NTF5 | Neurotrophin 5 (neurotrophin 4/5) |
| 1.5 | 1 | GDF10 | Growth differentiation factor 10 |
| 1.5 | 1.5 | TNFSF13B | Tumor necrosis factor (ligand) superfamily, member 13b |
| 1.5 | 2.5 | IFNA1 | Interferon, alpha 1 |
| 1.4 | −1.3 | INHBC | Inhibin, beta C |
| 1.4 | 2.8 | FGF7 | Galactokinase 2 |
| 1.4 | 3.3 | IL24 | Interleukin 24 |
| 1.4 | −1.1 | CCL27 | Chemokine (C-C motif) ligand 27 |
| 1.3 | 1.9 | FGF13 | Fibroblast growth factor 13 |
| 1.3 | 1.4 | IFNK | Interferon, kappa |
| 1.3 | 2 | ANGPT2 | Angiopoietin 2 |
| 1.3 | 7.6 | IL18 | Interleukin 18 (interferon-gamma-inducing factor) |
| 1.3 | 7 | NRG1 | Neuregulin 1 |

TABLE 4-continued

| VSV | IFNβ | Gene Name | Gene Identification |
|---|---|---|---|
| 1.3 | 4.9 | NTF3 | Neurotrophin 3 |
| 1.2 | 15 | FGF10 | Fibroblast growth factor 10 |
| 1.2 | 1.9 | KITLG | KIT ligand |
| 1.2 | −1.3 | IL17D | Interleukin 17D |
| 1.2 | 1.1 | TNFSF4 | Tumor necrosis factor (ligand) superfamily, member 4 |
| 1.2 | 1.3 | VEGFA | Vascular endothelial growth factor |
| 1.1 | 2.4 | FGF11 | Fibroblast growth factor 11 |
| 1.1 | −1.4 | IL17E | Interleukin 17E |
| 1.1 | −2.1 | TGFB1 | Transforming growth factor, beta 1 |
| 1 | 3.1 | GH1 | Growth hormone 1 |
| −1 | 6.1 | IL9 | Interleukin 9 |
| −1 | −2.5 | EFNB3 | Ephrin-B3 |
| −1 | 1.8 | VEGFB | Vascular endothelial growth factor B |
| −1 | −1.2 | IL1F7 | Interleukin 1 family, member 7 (zeta) |
| −1 | −2.1 | GDF11 | Growth differentiation factor 11 |
| −1.1 | 1.3 | ZFP91 | Zinc finger protein 91 homolog (mouse) |
| −1.2 | −1.1 | BMP6 | Bone morphogenetic protein 6 |
| −1.2 | −1.2 | AMH | Anti-Mullerian hormone |
| −1.3 | −1 | LEFTY1 | Left-right determination factor 1 |
| −1.3 | 2.4 | EFNA3 | Ephrin-A3 |
| −1.3 | −1.3 | LASS1 | LAG1 longevity assurance homolog 1 |
| −1.5 | 1 | EFNA4 | Ephrin-A4 |
| −1.8 | 1.3 | PDGFD | DNA-damage inducible protein 1 |
| −1.8 | 1.8 | IL10 | Interleukin 10 |
| −1.9 | 1.6 | GDF5 | Growth differentiation factor 5 |
| −1.9 | 1.3 | EFNA2 | Ephrin-A2 |
| −1.9 | −1.5 | EFNB1 | Ephrin-B1 |
| −1.9 | −1.4 | GDF8 | Growth differentiation factor 8 |
| −1.9 | 1.6 | PDGFC | Platelet derived growth factor C |
| −2.2 | 2.4 | TSLP | Thymic stromal lymphopoietin |
| −2.3 | −1.5 | BMP10 | Bone morphogenetic protein 10 |
| −2.4 | −4.6 | CXCL12 | Chemokine (C—X—C motif) ligand 12 |
| −2.5 | 4 | IFNG | Interferon, gamma |
| −2.6 | 1.2 | EPO | Erythropoietin |
| −2.7 | −2.1 | GAS6 | Growth arrest-specific 6 |
| −2.9 | 2.9 | PRL | Prolactin |
| −2.9 | −2.1 | BMP4 | Bone morphogenetic protein 4 |
| −2.9 | −5.7 | INHA | Inhibin, alpha |
| −3 | −1.3 | GDF9 | Growth differentiation factor 9 |
| −3.1 | −1.5 | FGF18 | Fibroblast growth factor 18 |
| −3.2 | N/A | IL17 | Interleukin 17 |
| −3.2 | −1.1 | IL26 | Interleukin 26 |
| −3.4 | 1.2 | EFNA1 | Ephrin-A1 |
| −3.8 | −1.1 | FGF12 | Fibroblast growth factor 12 |
| −4 | −2.3 | FGF9 | Fibroblast growth factor 9 (glia-activating factor) |
| −4.5 | 1.4 | CCL26 | Chemokine (C-C motif) ligand 26 |
| −8 | 9.7 | CCL19 | Chemokine (C-C motif) ligand 19 |
| N/A | N/A | BMP15 | Bone morphogenetic protein 15 |
| N/A | N/A | CCL15 | Chemokine (C-C motif) ligand 14 |
| N/A | N/A | CCL16 | Chemokine (C-C motif) ligand 16 |
| N/A | N/A | CCL18 | Chemokine (C-C motif) ligand 18 |
| N/A | N/A | CCL23 | Chemokine (C-C motif) ligand 23 |
| N/A | N/A | CD40LG | CD40 ligand (TNF superfamily) |
| N/A | N/A | CSF3 | Colony stimulating factor 3 (granulocyte) |
| N/A | N/A | CXCL5 | Chemokine (C—X—C motif) ligand 5 |
| N/A | N/A | FGF4 | Fibroblast growth factor 4 |
| N/A | N/A | FGF6 | Fibroblast growth factor 6 |
| N/A | N/A | GH2 | Growth hormone 2 |
| N/A | N/A | IL2 | Interleukin 2 |
| N/A | N/A | IL21 | Interleukin 21 |
| N/A | N/A | IL28A | Interleukin 28A (interferon, lambda 2) |
| N/A | N/A | INHBA | Inhibin, beta A |
| N/A | N/A | NRG3 | Neuregulin 3 |
| N/A | N/A | TNFSF11 | Tumor necrosis factor (ligand) superfamily, member 11 |
| N/A | N/A | TNFSF13 | Tumor necrosis factor (ligand) superfamily, member 13 |
| N/A | 6.5 | NRG4 | Neuregulin 4 |
| N/A | 6.1 | IL3 | Interleukin 3 (colony-stimulating factor, multiple) |
| N/A | 1.8 | TNFSF9 | Tumor necrosis factor (ligand) superfamily, member 9 |

Oncolytic VSV Potentiates SMC Therapy in Preclinical Animal Models of Cancer

Figure 20:
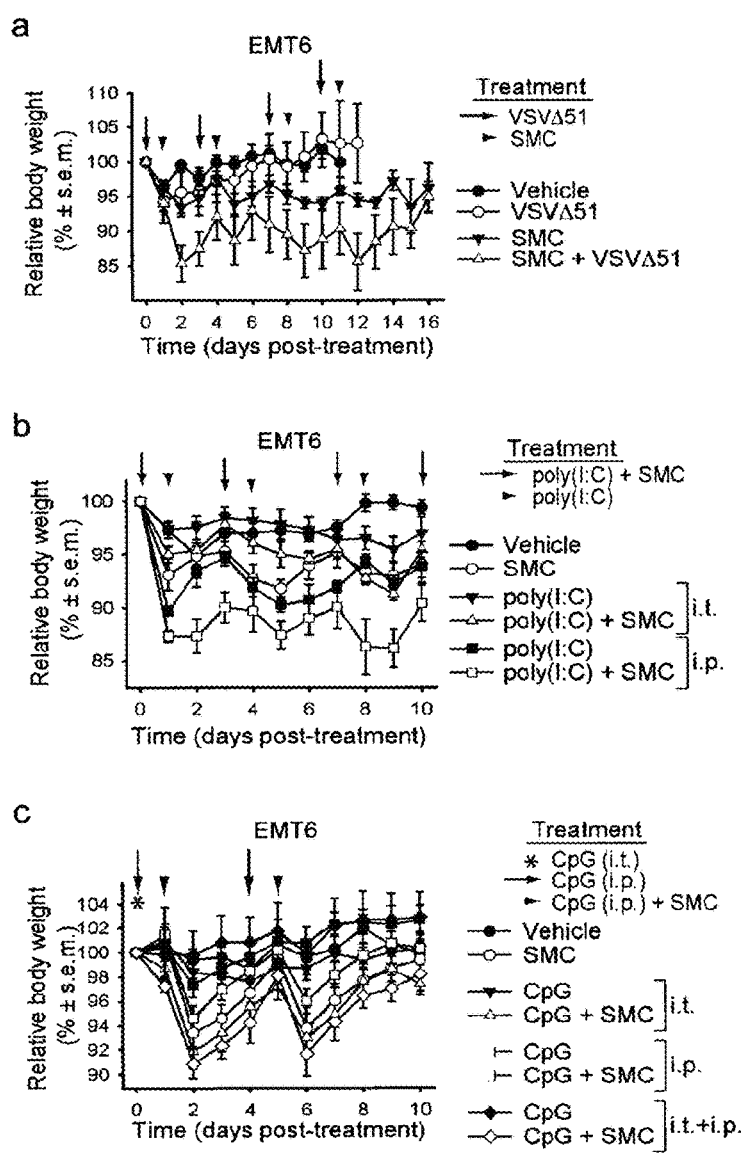
FIGS. 20a-20c are a set of graphs showing that SMC treatment induces transient weight loss in a syngeneic mouse model of cancer.

To evaluate SMC and oncolytic VSV co-therapy in vivo, the EMT6 mammary carcinoma was used as a syngeneic, orthotopic model. Preliminary safety and pharmacodynamic experiments revealed that a dose of 50 mg/kg LCL161 delivered by oral gavage was well tolerated and induced cIAP1/2 knockdown in tumors for at least 24 hrs, and up to 48-72 hours in some cases (FIGS. 19a, 19b, and 24g). When tumors reached ~100 mm$^3$, we began treating mice twice weekly with SMC and VSVΔ51, delivered systemically. As single agents, SMC therapy led to a decrease in the rate of tumor growth and a modest extension in survival, while VSVΔ51 treatments had no bearing on tumor size or survival (FIGS. 4a and 4b). In stark contrast, combined SMC and VSVΔ51 treatment induced dramatic tumor regressions and led to durable cures in 40% of the treated mice. Consistent with the bystander killing mechanism elucidated in vitro, immunofluorescence analyses revealed that the infectivity of VSVΔ51 was transient and limited to small foci within the tumor (FIG. 4c), whereas caspase-3 activation was widespread in the SMC and VSVΔ51 co-treated tumors (FIG. 4d). Furthermore, immunoblots with tumor lysates demonstrated activation of caspase-8 and -3 in doubly-treated tumors (FIGS. 4e, 24b, and 24g). While the animals in the combination treatment cohort experienced weight loss, the mice fully recovered following the last treatment (FIG. 20a).

To confirm these in vivo data in another model system, the human HT-29 colorectal adenocarcinoma xenograft model was tested in nude (athymic) mice. HT-29 is a cell line that is highly responsive to bystander killing by SMC and VSVΔ51 co-treatment in vitro (FIGS. 21a and 21b). Similar to our findings in the EMT6 model system, combination therapy with SMC and VSVΔ51 induced tumor regression and a significant extension of mouse survival (FIG. 21c). In contrast, neither monotherapy had any effect on HT-29 tumors. Furthermore, there was no additional weight loss in the double treated mice compared to SMC treated mice (FIG. 21d). These results indicate that the synergy is highly efficacious in a refractory xenograft model and that the adaptive immune response does not have a major role initially in the efficacy of SMC and OV co-therapy.

Role of the Innate Antiviral Responses and Immune Effectors in Co-treatment Synergy It was next determined whether oncolytic VSV infection coupled with SMC treatment leads to TNFα- or IFNβ-mediated cell death in vivo. It was investigated whether blocking TNFα signalling via neutralizing antibodies would affect SMC and VSVΔ51 synergy in the EMT6 tumor model. Compared to isotype matched antibody controls, the application of TNFα neutralizing antibodies reverted the tumor regression and decreased the survival rate to values close to the control and single treatment groups (FIGS. 4f and 4g). This demonstrates that TNFα is required in vivo for the anti-tumor combination efficacy of SMC and oncolytic VSV.

To investigate the role of IFNβ signaling in the SMC and OV combination paradigm, Balb/c mice bearing EMT6 tumors were treated with IFNAR1 blocking antibodies. Mice treated with the IFNAR1 blocking antibody succumbed to viremia within 24-48 hours post infection. Prior to death, tumors were collected at 18-20 hours after virus infection, and the tumors were analyzed for caspase activity. Even though these animals with defective type I IFN signaling were ill due to a large viral burden, the excised tumors did not demonstrate signs of caspase-8 activity and only showed minimal signs of caspase-3 activity (FIG. 22) in contrast to the control group, which showed the expected activation of caspases within the tumor (FIG. 22). These results support the hypothesis that intact type I IFN signaling is required to mediate the anti-tumor effects of the combination approach.

To assess the contribution of innate immune cells or other immune mediators to the efficacy of OV/SMC combination therapy, treating EMT6 tumors was first attempted in immunodeficient NOD-scid or NSG (NOD-scid-IL2Rgamma$^{null}$) mice. However, similar to the IFNAR1 depletion signaling studies, these mice also died rapidly due to viremia. Therefore, the contribution of innate immune cells was addressed by employing an ex vivo splenocyte culture system as a surrogate model. Innate immune populations that have the capacity to produce TNFα were positively selected and further sorted from naïve splenocytes. Macrophages (CD11b+F4/80+), neutrophils (CD11b+Gr1+), NK cells (CD11b−CD49b+) and myeloid-negative (lymphoid) population (CD11b−CD49−) were stimulated with VSVΔ51, and the conditioned medium was transferred to EMT6 cells to measure cytotoxicity in the presence of SMC. These results show that VSVΔ51-stimulated macrophages and neutrophils, but not NK cells, are capable of producing factors that lead to cancer cell death in the presence of SMCs (FIG. 23a). Primary macrophages from bone marrow were also isolated and these macrophages also responded to oncolytic VSV infection in a dose-dependent manner to produce factors which kill EMT6 cells (FIG. 23b). Altogether, these findings demonstrate that multiple innate immune cell populations can respond to mediate the observed anti-tumor effects, and that macrophages are the most likely effectors of this response.

Immune Adjuvants Poly(I:C) and CpG Potentiate SMC Therapy In Vivo

It was next investigated whether synthetic TLR agonists, which are known to induce an innate proinflammatory response, would synergize with SMC therapy. EMT6 cells were co-cultured with mouse splenocytes in a transwell insert system, and the splenocytes were treated with SMC and agonists of TLR 3, 4, 7 or 9. All of the tested TLR agonists were found to induce the bystander death of SMC treated EMT6 cells (FIG. 5a). The TLR4, 7, and 9 agonists LPS, imiquimod, and CpG, respectively, required splenocytes to induce bystander killing of EMT6 cells, presumably because their target TLR receptors are not expressed in EMT6 cells. However, the TLR3 agonist poly(I:C) led to EMT6 cell death directly in the presence of SMCs. Poly(I:C) and CpG were next tested in combination with SMC therapy in vivo. These agonists were chosen as they have proven to be safe in humans and are currently in numerous mid to late stage clinical trials for cancer. EMT6 tumors were established and treated as described above. While poly(I:C) treatment had no bearing on tumor growth as a single agent, combination with SMCs induced substantial tumor regression and, when delivered intraperitoneally, led to durable cures in 60% of the treated mice (FIGS. 5b and 5c). Similarly, CpG monotherapy had no bearing on tumor size or survival, but when combined with SMC therapy led to tumor regressions and durable cures in 88% of the treated mice (FIGS. 5d and 5e). Importantly, these combination therapies were well tolerated by the mice, and their body weight returned to pre-treatment levels shortly after the cessation of therapy (FIGS. 20b and 20c). Taken together with the oncolytic VSV results, the data demonstrate that a series of clinically advanced innate immune adjuvants strongly and safely synergize with SMC therapy in vivo, inducing tumor regression and durable cures in several treatment refractory, aggressive mouse models of cancer.

Example 2

Inactivated Viral Particles, Cancer Vaccines, and Stimulatory Cytokines Synergize with SMCs to Kill Tumors The use of current cancer immunotherapies, such as BCG (Bacillus Calmette-Guerin), recombinant interferon (e.g. IFNα), and recombinant Tumor Necrosis Factor (e.g. TNFα used in isolated limb perfusion for example), and the recent clinical use of biologics (e.g. blocking antibodies) to immune checkpoint inhibitors that overcome tumor-mediated suppression of the immune system (such as anti- CTLA-4 and anti-PD-1 or PDL-1 monoclonal antibodies) highlight the potential of 'cancer immunotherapy' as an effective treatment modality. As shown in Example 1, we have demonstrated the robust potential of non-viral immune stimulants to synergize with SMCs (FIG. 5). To expand on these studies, we also examined for the potential of SMCs to synergize with non-replicating rhabdovirus-derived particles (called NRRPs), which are UV-irradiated VSV particles that retain their infectious and immunostimulatory properties without the ability to replicate and spread. To assess if NRRPs directly synergize with SMCs, we co-treated various cancer cell lines, EMT6, DBT, and CT-2A, with SMCs and differing levels of NRRPs, and assessed cell viability by Alamar blue. We observed that NRRPs synergize with SMCs in these cancer cell lines (FIG. 25a). To assess if NRRPs can induce a potent proinflammatory response, we treated fractionated mouse splenocytes with NRRPs (or synthetic CpG ODN 2216 as a positive control), transferred the cell culture supernatants to EMT6 cells in culture in a dose-response fashion, and treated the cells with vehicle or SMC. We observed that the immunogenicity of NRRPs is at a similar level of CpG, as there was a considerable proinflammatory response, which led to a high degree of EMT6 cell death in the presence of SMCs (FIG. 25b). As the treatment of CpG and SMC in the EMT6 tumor model resulted in a 88% cure rate (FIG. 5d), these findings suggest that the combination of SMCs and NRRPs can be highly synergistic in vivo.

Our success in finding synergy between SMCs and live or inactivated single-stranded RNA oncolytic rhabdoviruses (e.g., VSVΔ51, Maraba-MG1, and NRRPs) suggested that a clinic approved attenuated vaccine may be able to synergize with SMCs. To test this possibility, we assessed the ability to synergize with SMCs of the cancer biologic, the vaccine for tuberculosis mycobacterium, BCG, which is typically used to treat bladder cancer in situ due to the high local production of TNFα. Indeed, the combination of SMC and BCG potently synergises to kill EMT6 cells in vitro (FIG. 26a). These findings were similarly extended in vivo; we observed significant tumor regression with combined treatment of an oral SMC and BCG administered locally or systemically (i.e., either given intratumorally or intraperitoneally, respectively) (FIG. 26b). These findings attest to the applicability of approved vaccines for combination cancer immunotherapies with SMCs.

Type I IFN Synergizes with SMCs in vivo

Figure 27:
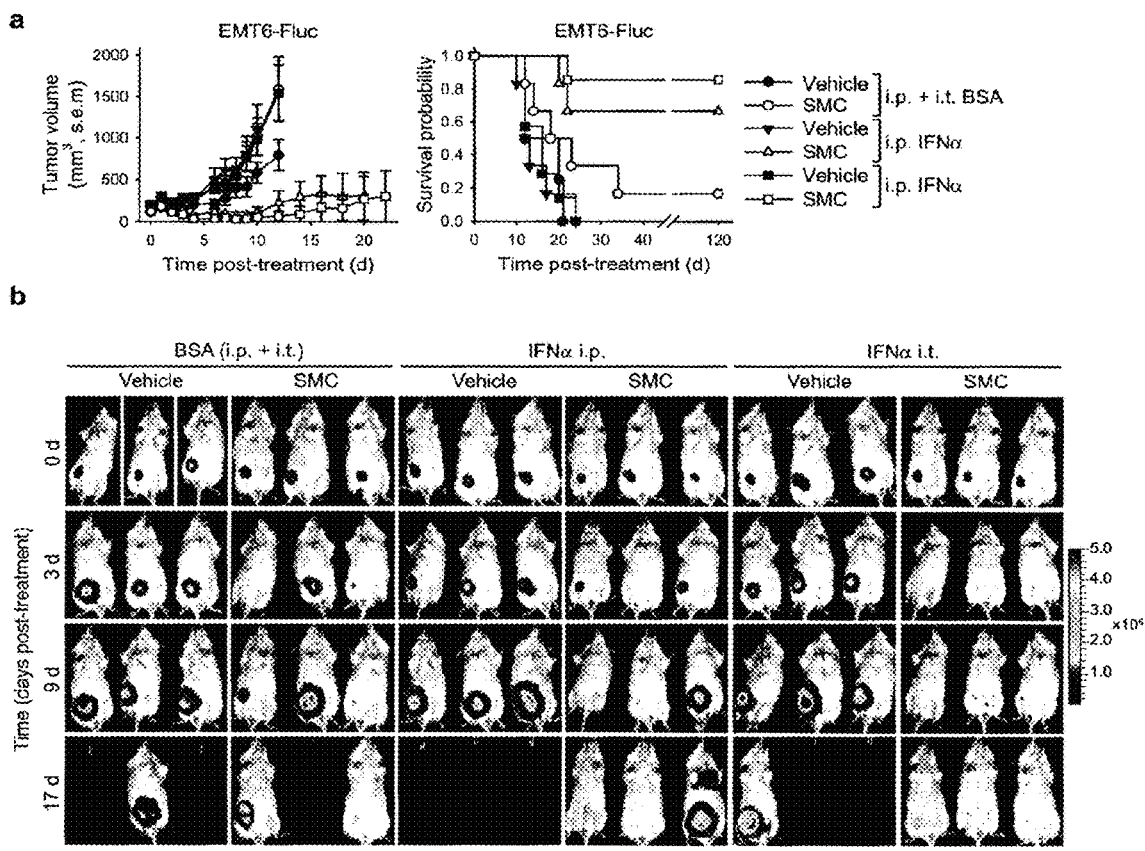

The effects of viruses, and likely other TLR agonists and vaccines, appear to be mediated, in part, by type I IFN production, which is controlled by various signaling mechanism, including mRNA translation. Our findings raised the distinct possibility of combining SMC treatment with existing immunotherapies, such as recombinant IFN, as an effective approach to treat cancer. To explore the potential of this combination, we conducted two treatment regimens of SMC and either intraperitoneal or intratumoral injections of recombinant IFNα in the syngeneic orthotopic EMT6 mammary carcinoma model. While treatment of IFNα had no effect on EMT6 tumor growth or overall survival, SMC treatment slightly extended mouse survival and had a cure rate of 17% (FIG. 27). However, the combined treatment of SMC and intraperitoneal or intratumoral injections of IFNα significantly delayed tumor growth and extended survival of tumor-bearing mice, resulting in cure rates of 57% and 86%, respectively (FIG. 27) These results support the hypothesis that direct stimulation with type I IFN can synergize with SMCs to eradicate tumors in vivo.

Assessment of Additional Oncolytic Rhabdoviruses for the Potential of Synergy with SMCs While VSVΔ51 is a preclinical candidate, the oncolytic rhabdoviruses VSV-IFNβ and Maraba-MG1 are currently undergoing clinical testing in cancer patients. As shown in Example 1, we have demonstrated that Maraba-MG1 synergizes with SMCs in vitro (FIG. 9). We also confirmed that SMCs synergized with the clinical candidates, VSV-IFNβ and VSV-NIS-IFNβ (i.e. carrying the imaging gene, NIS, sodium iodide symporter), in EMT6 cells (FIG. 28). To assess whether these viruses can induce a proinflammatory state in vivo, we treated infected mice i.v. with $5 \times 10^8$ PFU of VSVΔ51, VSV-IFNβ, and Maraba-MG1 and measured the level of TNFα from the serum of infected mice. In all cases, there was a transient, but robust increase of TNFα from oncolytic virus infection at 12 hrs post-infection, which was barely detectable by 24 hr (FIG. 29). This makes sense as these infections are self-limiting in immunocompetent hosts. These results suggest that the clinical candidate oncolytic rhabdoviruses have the potential to synergize with SMCs in a fashion similar to VSVΔ51.

Figure 15:
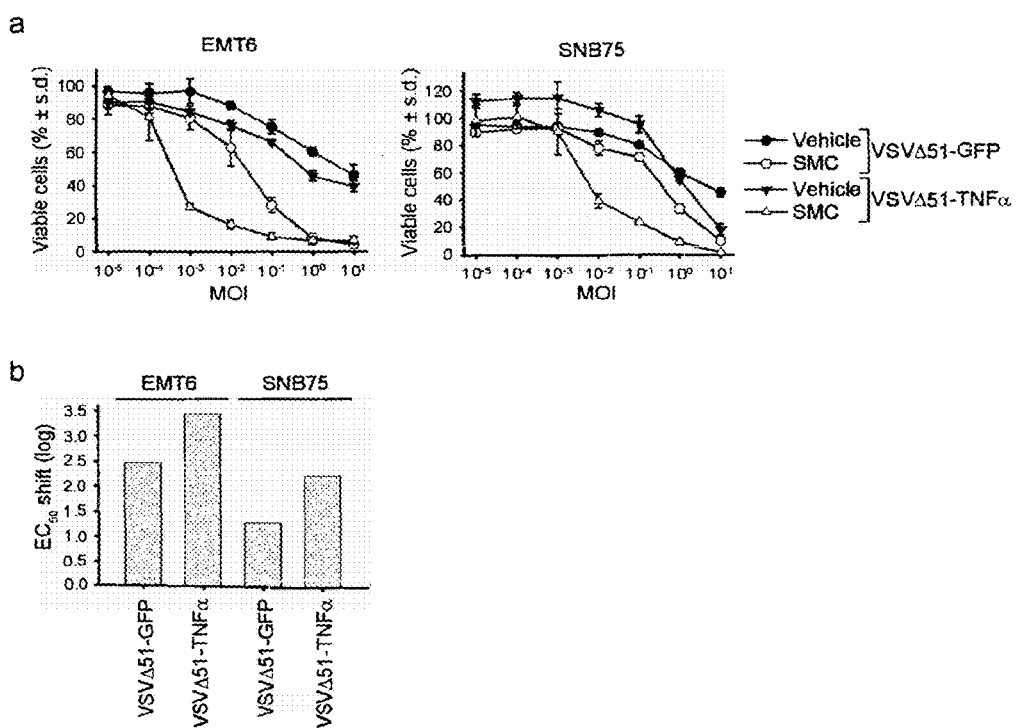
FIGS. 15a and 15b are a set of graphs showing that expression of TNFα transgene from OVs potentiates SMC-mediated cancer cell death further.

As shown in Example 1, we documented that a form of VSVΔ51 that was engineered to express full-length TNFα can enhance oncolytic virus induced death in the presence of SMC (FIG. 15). To expand on these findings, we also engineered VSVΔ51 to express a form of TNFα that had its intracellular and transmembrane components replaced with the secretory signal from human serum albumin (VSVΔ51-solTNFα). Compared to full-length TNFα (memTNFα), solTNFα is constitutively secreted from host cells, while the memTNFα form may be anchored on plasma membrane (and still capable of inducing cell death in a juxtacrine manner) or is released due to endogenous processing by metalloproteases (such as ADAM17) to kill cells in a paracrine fashion. We assessed whether either forms of TNFα from oncolytic VSV infected cells will synergize with SMC in the orthotopic syngeneic mammary cancer model, EMT6. As expected, treatment with SMC slightly delayed EMT6 tumor growth rates and slightly extended the survival of tumor bearing mice, and the combination of vehicle with either VSVΔ51-memTNFα or VSVΔ51-solTNFα had no impact on overall survival or tumor growth rates (FIGS. 30a, b). On the other hand, virally expressed TNFα significantly slowed tumor growth rates and led to increases in the survival rates of 30% and 70%, respectively. Notably, the 40% tumor cure rate from combined SMC and VSVΔ51 (FIG. 4a) required four treatments and a dose of $5 \times 10^8$ PFU of VSVΔ51. However, the combination of TNFα-expressing oncolytic VSV and SMC resulted in a higher cure rate and was accomplished with two treatment regimens at a virus dose of $1 \times 10^8$ PFU. To assess whether this treatment strategy can be applied to other refractory syngeneic models, we assessed whether VSVΔ51-solTNFα synergizes with SMCs in a subcutaneous model of the mouse colon carcinoma cell line, CT-26. As expected, we did not observe an impact of tumor growth rates or survival with VSVΔ51-solTNFα and observed a modest decrease of the tumor growth rate and a slight extension of survival (FIG. 30c). However, we were able to further delay tumor growth and extend survival of these tumor bearing mice with the combined treatment of SMC and VSVΔ51-solTNFα. Hence, the inclusion of a TNFα transgene within oncolytic viruses is a significant advantage for the combination of SMC. One could easily envisage the inclusion of other death ligand transgenes, such as TRAIL, FasL, or lymphotoxin, into viruses to synergize with SMCs.

Exploring the Potential of SMCs to Eradicate Brain Tumors

The combination of SMCs with immune stimulatory agents is applicable to many different types of cancer, including brain malignancies for which effective therapies are lacking and for which immunotherapies hold promise. As a first step, we determined whether SMCs can cross the blood-brain-barrier (BBB) in a mouse model of brain tumors, as the BBB is a significant barrier to drug entry into the brain. We observed the SMC-induced degradation of cIAP1/2 proteins in intracranial CT-2A tumors several hours after drug administration, indicative that SMCs are capable of crossing the BBB to antagonize cIAP1/2 and potentially XIAP within brain tumors (FIG. 31a). We also demonstrated that the direct injection of SMC (10 µL of a 100 µM solution) intracranially can result in the potent down-regulation of both cIAP1/2 and XIAP proteins (FIG. 31b), which is a direct consequence of SMC-induced autoubiquitination of the IAPs or the result of tumor cell death induction in the case of XIAP loss. As a second step, we wished to determine whether systemic stimulation of immune stimulants can led to a proinflammatory response in the brain of naïve mice. Indeed, we observed marked up-regulation of TNFα levels from the brain from mice that were intraperitoneally injected with the viral mimic, poly(I:C), a TLR3 agonist (FIG. 32a). We followed up this finding by extracting crude protein lysates from the brains of mice that were treated with poly(I:C) or with the clinical candidate oncolytic rhabdoviruses VSVΔ51, VSV-IFNβ, or Maraba-MG1, and then applied these lysates onto CT-2A or K1580 glioblastoma cells in the presence of SMCs. We observed that the stimulation of an innate immune response with these non-viral synthetic or biologic viral agents resulted in enhanced cell death in the presence of SMCs with these two glioblastoma cell lines (FIG. 32b). As a third step, we also confirmed that poly(I:C) could be directly administered intracranially without overt toxicities, which may provide an even increased cytokine induction at the site of tumors (FIG. 32c). Finally, we assessed whether the direct immune stimulation within the brain or systemic stimulation would lead to durable cures in SMC-treated mouse models of brain cancer. The combination of SMCs orally and poly(I:C) intracranially or VSVΔ51 i.v. results in the near complete survival of CT-2A bearing mouse gliomas (FIG. 32d,e), with an expected survival rate of 86 and 100%, respectively. As a follow-up to the observed synergy between SMC and intracranial treatment of poly(I:C), we also assessed the potential for treatment of CT-2A gliomas with direct, simultaneous intracranial injections of SMC and recombinant human IFNα (B/D). Indeed, we observed a marked positive impact of mouse survival with the combined treatment, with a cure rate of 50% (FIG. 33). Importantly, the single or combined SMC or IFNα treatment did not result in any overt neurotoxicity in these tumor bearing mice. Overall, these results reveal that multiple modes of SMC treatment can synergize with a multitude of locally or systemically administered innate immunostimulants to kill cancer cell in vitro and to eradicate tumors in animal models of cancer.

Methods

Reagents

Novartis provided LCL161 (Houghton, P. J. et al. Initial testing (stage 1) of LCL161, a SMAC mimetic, by the Pediatric Preclinical Testing Program. *Pediatr Blood Cancer* 58: 636-639 (2012); Chen, K. F. et al. Inhibition of Bcl-2 improves effect of LCL161, a SMAC mimetic, in hepatocellular carcinoma cells. *Biochemical Pharmacology* 84: 268-277 (2012)). SM-122 and SM-164 were provided by Dr. Shaomeng Wang (University of Michigan, USA) (Sun, H. et al. Design, synthesis, and characterization of a potent, nonpeptide, cellpermeable, bivalent Smac mimetic that concurrently targets both the BIR2 and BIR3 domains in XIAP. *J Am Chem Soc* 129: 15279-15294 (2007)). AEG40730 (Bertrand, M. J. et al. cIAP1 and cIAP2 facilitate cancer cell survival by functioning as E3 ligases that promote RIP1 ubiquitination. *Mol Cell* 30: 689-700 (2008)) was synthesized by Vibrant Pharma Inc (Brantford, Canada). OICR720 was synthesized by the Ontario Institute for Cancer Research (Toronto, Canada) (Enwere, E. K. et al. TWEAK and cIAP1 regulate myoblast fusion through the noncanonical NF-kappaB signalling pathway. *Sci Signal* 5: ra75 (2013)). IFNα, IFNβ, IL28 and IL29 were obtained from PBL Interferonsource (Piscataway, USA). All siRNAs were obtained from Dharmacon (Ottawa, Canada; ON TARGETplus SMARTpool). CpG-ODN 2216 was synthesized by IDT (5'-gggGGACGATCGTCggggggg-3' (SEQ ID NO: 1), lowercase indicates phosphorothioate linkages between these nucleotides, while italics identify three CpG motifs with phosphodiester linkages). Imiquimod was purchased from BioVision Inc. (Milpitas, USA). poly(I:C) was obtained from InvivoGen (San Diego, USA). LPS was from Sigma (Oakville, Canada).

Cell Culture

Cells were maintained at 37° C. and 5% CO2 in DMEM media supplemented with 10% heat inactivated fetal calf serum, penicillin, streptomycin, and 1% non-essential amino acids (Invitrogen, Burlington, USA). All of the cell lines were obtained from ATCC, with the following exceptions: SNB75 (Dr. D. Stojdl, Children's Hospital of Eastern Ontario Research Institute) and SF539 (UCSF Brain Tumor Bank). Cell lines were regularly tested for mycoplasma contamination. For siRNA transfections, cells were reverse transfected with Lipofectamine RNAiMAX (Invitrogen) or DharmaFECT I (Dharmacon) for 48 hours as per the manufacturer's protocol.

Viruses

The Indiana serotype of VSVΔ51 (Stojdl, D. F. et al. VSV strains with defects in their ability to shutdown innate immunity are potent systemic anti-cancer agents. Cancer Cell 4(4), 263-275 (2003)) was used in this study and was propagated in Vero cells. VSVΔ51-GFP is a recombinant derivative of VSVΔ51 expressing jellyfish green fluorescent protein. VSVΔ51-Fluc expresses firefly luciferase. VSVΔ51 with the deletion of the gene encoding for glycoprotein (VSVΔ51ΔG) was propagated in HEK293T cells that were transfected with pMD2-G using Lipofectamine2000 (Invitrogen). To generate the VSVΔ51-TNFα construct, full-length human TNFα gene was inserted between the G and L viral genes. All VSVΔ51 viruses were purified on a sucrose cushion. Maraba-MG1, VVDD-B18R-, Reovirus and HSV1 ICP34.5 were generated as previously described (Brun, J. et al. Identification of genetically modified Maraba virus as an oncolytic rhabdovirus. *Mol Ther* 18, 1440-1449 (2010); Le Boeuf, F. et al. Synergistic interaction between oncolytic viruses augments tumor killing. *Mol Ther* 18, 888-895 (2011); Lun, X. et al. Efficacy and safety/toxicity study of recombinant vaccinia virus JX-594 in two immunocompetent animal models of glioma. *Mol Ther* 18, 1927-1936 (2010)). Generation of adenoviral vectors expressing GFP or co-expressing GFP and dominant negative IKKβ was as previously described 16.

In vitro Viability Assay

Cell lines were seeded in 96-well plates and incubated overnight. Cells were treated with vehicle (0.05% DMSO) or 5 µM LCL161 and infected with the indicated MOI of OV or treated with 250 U/mL IFNβ, 500 U/mL IFNα, 500 U/mL IFNγ, 10 ng/mL IL28, or 10 ng/mL IL29 for 48 hours. Cell viability was determined by Alamar blue (Resazurin sodium salt (Sigma)) and data was normalized to vehicle treatment. The chosen sample size is consistent with previous reports that used similar analyses for viability assays. For combination indices, cells were seeded overnight, treated with serial dilutions of a fixed combination mixture of VSVΔ51 and LCL161 (5000:1, 1000:1 and 400:1 ratios of PFU VSVΔ51: μM LCL161) for 48 hours and cell viability was assessed by Alamar blue. Combination indices (CI) were calculated according to the method of Chou and Talalay using Calcusyn (Chou, T. C. & Talaly, P. A simple generalized equation for the analysis of multiple inhibitions of Michaelis-Menten kinetic systems. *J Biol Chem* 252, 6438-6442 (1977)). An n=3 of biological replicates was used to determine statistical measures (mean with standard deviation or standard error).

Spreading Assay

A confluent monolayer of 786-0 cells was overlaid with 0.7% agarose in complete media. A small hole was made with a pipette in the agarose overlay in the middle of the well where 5×103 PFU of VSVΔ51-GFP was administered. Media containing vehicle or 5 μM LCL161 was added on top of the overlay, cells were incubated for 4 days, fluorescent images were acquired, and cells were stained with crystal violet.

Splenocyte Co-culture

EMT6 cells were cultured in multiwell plates and overlaid with cell culture inserts containing unfractionated splenocytes. Briefly, single-cell suspensions were obtained by passing mouse spleens through 70 μm nylon mesh and red blood cells were lysed with ACK lysis buffer. Splenocytes were treated for 24 hr with either 0.1 MOI of VSVΔ51ΔG, 1 μg/mL poly(I:C), 1 μg/mL LPS, 2 μM imiquimod, or 0.25 μM CpG prior in the presence of 1 μM LCL161. EMT6 cell viability was determined by crystal violet staining. An n=3 of biological replicates was used to determine statistical measures (mean, standard deviation).

Cytokine Responsiveness Bioassay

Cells were infected with the indicated MOI of VSVΔ51 for 24 hours and the cell culture supernatant was exposed to UV light for 1 hour to inactive VSVΔ51 particles. Subsequently, the UV-inactivated supernatant was applied to naive cells in the presence of 5 μM LCL161 for 48 hours. Cell viability was assessed by Alamar blue. An n=3 of biological replicates was used to determine statistical measures (mean, standard deviation).

Microscopy

To measure caspase-3/7 activation, 5 μM LCL161, the indicated MOI of VSVΔ51, and 5 μM CellPlayer Apoptosis Caspase-3/7 reagent (Essen Bioscience, Ann Arbor, USA) were added to the cells. Cells were placed in an incubator outfitted with an IncuCyte Zoom microscope with a 10× objective and phase-contrast and fluorescence images were acquired over a span of 48 hours. Alternatively, cells were treated with 5 μM LCL161 and 0.1 MOI of VSVΔ51-GFP and SMC for 36 hours and labeled with the Magic Red Caspase-3/7 Assay Kit (ImmunoChemsitry Technologies, Bloomington, USA). To measure the proportion of apoptotic cells, 1 μg/mL Annexin V-CF594 (Biotium, Hayward, USA) and 0.2 μM YOYO-1 (Invitrogen) was added to SMC and VSVΔ51 treated cells. Images were acquired 24 hours post-treatment using the IncuCyte Zoom. Enumeration of fluorescence signals was processed using the integrated object counting algorithm within the IncuCyte Zoom software. An n=12 (caspase-3/7) or n=9 (Annexin V, YOYO-1) of biological replicates was used to determine statistical measures (mean, standard deviation).

Multiple Step Growth Curves

Cells were treated with vehicle or 5 μM LCL161 for 2 hours and subsequently infected at the indicated MOI of VSVΔ51 for 1 hour. Cells were washed with PBS, and cells were replenished with vehicle or 5 μM LCL161 and incubated at 37° C. Aliquots were obtained at the indicated times and viral titers assessed by a standard plaque assay using African green monkey VERO cells.

Western Immunoblotting

Cells were scraped, collected by centrifugation and lysed in RIPA lysis buffer containing a protease inhibitor cocktail (Roche, Laval, Canada). Equal amounts of soluble protein were separated on polyacrylamide gels followed by transfer to nitrocellulose membranes. Individual proteins were detected by western immunoblotting using the following antibodies: pSTAT1 (9171), caspase-3 (9661), caspase-8 (9746), caspase-9 (9508), DR5 (3696), TNF-R1 (3736), cFLIP (3210), and PARP (9541) from Cell Signalling Technology (Danvers, USA); caspase-8 (1612) from Enzo Life Sciences (Farmingdale, USA); IFNAR1 (EP899) and TNF-R1 (19139) from Abcam (Cambridge, USA); caspase-8 (AHZ0502) from Invitrogen; cFLIP (clone NF6) from Alexis Biochemicals (Lausen, Switzerland); RIP1 (clone 38) from BD Biosciences (Franklin Lakes, USA); and E7 from Developmental Studies Hybridoma Bank (Iowa City, USA). Our rabbit anti-rat IAP1 and IAP3 polyclonal antibodies were used to detect human and mouse cIAP1/2 and XIAP, respectively. AlexaFluor680 (Invitrogen) or IRDye800 (Li-Cor, Lincoln, USA) were used to detect the primary antibodies, and infrared fluorescent signals were detected using the Odyssey Infrared Imaging System (Li-Cor).

RT-qPCR

Total RNA was isolated from cells using the RNAEasy Mini Plus kit (Qiagen, Toronto, Canada). Two-step RT-qPCR was performed using Superscript III (Invitrogen) and SsoAdvanced SYBR Green supermix (BioRad, Mississauga, Canada) on a Mastercycler ep realplex (Eppendorf, Mississauga, Canada). All primers were obtained from real-timeprimers.com. An n=3 of biological replicates was used to determine statistical measures (mean, standard deviation).

ELISA

Cells were infected with virus at the indicated MOI or treated with IFNβ for 24 hours and clarified cell culture supernatants were concentrated using Amicon Ultra filtration units. Cytokines were measured with the TNFα Quantikine high sensitivity, TNFα DuoSet, TRAIL DuoSet (R&D Systems, Minneapolis, USA) and VeriKine IFNβ (PBL Interferonsource) assay kits. An n=3 of biological replicates was used to determine statistical analysis.

EMT6 Mammary Tumor Model

Mammary tumors were established by injecting 1×105 wild-type EMT6 or firefly luciferase-tagged EMT6 (EMT6-Fluc) cells in the mammary fat pad of 6-week old female BALB/c mice. Mice with palpable tumors (~100 mm$^3$) were co-treated with either vehicle (30% 0.1 M HCl, 70% 0.1 M NaOAc pH 4.63) or 50 mg/kg LCL161 per os and either i.v. injections of either PBS or 5×108 PFU of VSVΔ51 twice weekly for two weeks. For poly(I:C) 25 and SMC treatments, animals were treated with LCL161 twice a week and either BSA (i.t.), 20 ug poly(I:C) i.t. or 2.5 mg/kg poly(I:C) i.p. four times a week. The SMC and CpG group was injected with 2 mg/kg CpG (i.p.) and the next day was followed with CpG and SMC treatments. The CpG and SMC treatments were repeated 4 days later. Treatment groups were assigned by cages and each group had min n=4-8 for statistical measures (mean, standard error; Kaplan-Meier with log rank analysis). The sample size is consistent with previous reports that examined tumor growth and mouse survival following cancer treatment. Blinding was not possible. Animals were euthanized when tumors metastasized intraperitoneally or when the tumor burden exceeded 2000 mm³. Tumor volume was calculated using $(\pi)(W)^2(L)/4$ where W=tumor width and L=tumor length. Tumor bioluminescence imaging was captured with a Xenogen2000 IVIS CCD-camera system (Caliper Life Sciences Massachusetts, USA) following i.p. injection of 4 mg luciferin (Gold Biotechnology, St. Louis, USA).

HT-29 Subcutaneous Tumor Model

Subcutaneous tumors were established by injecting 3×106 HT-29 cells in the right flank of 6-week old female CD-1 nude mice. Palpable tumors (~200 mm3) were treated with five intratumoral injections (i.t.) of PBS or 1×108 PFU of VSVΔ51. Four hours later, mice were administered vehicle or 50 mg/kg LCL161 per os. Treatment groups were assigned by cages and each group had min n=5-7 for statistical measures (mean, standard error; Kaplan-Meier with log rank analysis). The sample size is consistent with previous reports that examined tumor growth and mouse survival following cancer treatment. Blinding was not possible. Animals were euthanized when tumor burden exceeded 2000 mm³. Tumor volume was calculated using $(\pi)(W)^2(L)/4$ where W=tumor width and L=tumor length.

All animal experiments were conducted with the approval of the University of Ottawa Animal Care and Veterinary Service in concordance with guidelines established by the Canadian Council on Animal Care.

Antibody-mediated Cytokine Neutralization

For neutralizing TNFα signaling in vitro, 25 µg/mL of α-TNFα(XT3.11) or isotype control (HRPN) was added to EMT6 cells for 1 hour prior to LCL161 and VSVΔ51 or IFNβ co-treatment for 48 hours. Viability was assessed by Alamar blue. For neutralizing TNFα in the EMT6-Fluc tumor model, 0.5 mg of α-TNFα or α-HRPN was administered 8, 10 and 12 days post-implantation. Mice were treated with 50 mg/kg LCL161 (p.o.) on 8, 10 and 12 days post-implantation and were infected with 5×108 PFU VSVΔ51 i.v. on days 9, 11 and 13. For neutralization of type I IFN signalling, 2.5 mg of α-IFNAR1 (MAR1-5A3) or isotype control (MOPC-21) were injected into EMT6-tumor bearing mice and treated with 50 mg/kg LCL161 (p.o.) for 20 hours. Mice were infected with 5×108 PFU VSVΔ51 (i.v.) for 18-20 hours and tumors were processed for Western blotting. All antibodies were from BioXCell (West Lebanon, USA).

Flow Cytometry and Sorting

EMT6 cells were co-treated with 0.1 MOI of VSVΔ51-GFP and 5 µM LCL161 for 20 hours. Cells were trypsinized, permeabilized with the CytoFix/CytoPerm kit (BD Biosciences) and stained with APC-TNFα (MP6-XT22) (BD Biosciences). Cells were analyzed on a Cyan ADP 9 flow cytometer (Beckman Coulter, Mississauga, Canada) and data was analyzed with FlowJo (Tree Star, Ashland, USA).

Splenocytes were enriched for CD11b using the EasySep CD11b positive selection kit (StemCell Technologies, Vancouver, Canada). CD49+ cells were enriched using the EasySep CD49b positive selection kit (StemCell Technologies) from the CD11b– fraction. CD11b+ cells were stained with F4/80-PE-Cy5 (BM8, eBioscience) and Gr1-FITC (RB6-8C5, BD Biosciences) and further sorted with MoFlo Astrios (Beckman Coulter). Flow cytometry data was analyzed using Kaluza (Beckman Coulter). Isolated cells were infected with VSVΔ51 for 24 hours and clarified cell culture supernatants were applied to EMT6 cells for 24 hours in the presence of 5 µM LCL161.

Bone Marrow Derived Macrophages

Mouse femurs and radius were removed and flushed to remove bone marrow. Cells were cultured in RPMI with 8% FBS and 5 ng/ml of M-CSF for 7 days. Flow cytometry was used to confirm the purity of macrophages (F4/80+ CD11b+).

Immunohistochemistry

Excised tumors were fixed in 4% PFA, embedded in a 1:1 mixture of OCT compound and 30% sucrose, and sectioned on a cryostat at 12 µm. Sections were permeablized with 0.1% Triton X-100 in blocking solution (50 mM Tris-HCl pH 7.4, 100 mM L-lysine, 145 mM NaCl and 1% BSA, 10% goat serum). α-cleaved caspase 3 (C92-605, BD Pharmingen, Mississauga, Canada) and polyclonal antiserum VSV (Dr. Earl Brown, University of Ottawa, Canada) were incubated overnight followed by secondary incubation with AlexaFluor-coupled secondary antibodies (Invitrogen).

Statistical Analysis

Comparison of Kaplan-Meier survival plots was conducted by log-rank analysis and subsequent pairwise multiple comparisons were performed using the Holm-Sidak method (SigmaPlot, San Jose, USA). Calculation of $EC_{50}$ values was performed in GraphPad Prism using normalized nonlinear regression analysis. The $EC_{50}$ shift was calculated by subtracting the $\log_{10} EC_{50}$ of SMC-treated and VSVΔ51-infected cells from $\log_{10} EC_{50}$ of vehicle treated cells infected by VSVΔ51. To normalize the degree of SMC synergy, the $EC_{50}$ value was normalized to 100% to compensate for cell death induced by SMC treatment alone.

Other Embodiments

All publications, patent applications, and patents mentioned in this specification are herein incorporated by reference.

While the invention has been described in connection with the specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A composition comprising LCL161 or a pharmaceutically acceptable salt thereof and a vesicular stomatitis virus (VSV) Δ51.

2. A pharmaceutical composition comprising the composition of claim 1 and a pharmaceutically acceptable carrier.

3. A kit comprising LCL161 or a pharmaceutically acceptable salt thereof and a VSVΔ51.

4. The kit of claim 3, wherein the LCL161 and the VSVΔ51 are formulated as separate compositions.

5. The kit of claim 4, wherein the LCL161 and the VSVΔ51 are formulated as a single composition.

6. The kit of claim 3, further comprising instructions for administration.

* * * * *